United States Patent [19]
Brzezinski et al.

[11] Patent Number: 5,871,730
[45] Date of Patent: Feb. 16, 1999

[54] THERMOSTABLE XYLANASE DNA, PROTEIN AND METHODS OF USE

[75] Inventors: Ryszard Brzezinski, Sherbrooke; Claude V. Déry, Fleurimont; Carole Beaulieu, Sherbrooke, all of Canada

[73] Assignee: Université de Sherbrooke, Sherbrooke, Canada

[21] Appl. No.: 282,197

[22] Filed: Jul. 29, 1994

[51] Int. Cl.$^6$ .......................... A61K 38/47; C12P 19/00; C12N 9/42; D21C 1/00
[52] U.S. Cl. .................... 424/94.61; 435/72; 435/209; 435/262; 435/277; 435/278; 530/412
[58] Field of Search .............................. 435/72, 209, 262, 435/277, 278; 530/412

[56] References Cited

U.S. PATENT DOCUMENTS

| | | | |
|---|---|---|---|
| 5,110,412 | 5/1992 | Fuentes et al. | 162/5 |
| 5,298,405 | 3/1994 | Nevalainen et al. | 435/209 |
| 5,308,449 | 5/1994 | Fuentes et al. | 162/72 |
| 5,658,765 | 8/1997 | Noguchi et al. | 435/99 |

FOREIGN PATENT DOCUMENTS

| | | |
|---|---|---|
| 0 262 040 A1 | 3/1988 | European Pat. Off. |
| 0 334 739 A1 | 9/1989 | European Pat. Off. |
| 0 351 655 A1 | 1/1990 | European Pat. Off. |
| 0 383 999 | 8/1990 | European Pat. Off. |
| 0 386 888 A2 | 9/1990 | European Pat. Off. |
| 0 395 792 A2 | 11/1990 | European Pat. Off. |
| 0 463 706 A1 | 1/1992 | European Pat. Off. |
| 0 473 545 A3 | 3/1992 | European Pat. Off. |
| 0 489 104 B1 | 6/1992 | European Pat. Off. |
| 40 00 558 A1 | 7/1990 | Germany. |
| WO 89/08738 | 9/1989 | WIPO. |
| WO 91/02791 | 3/1991 | WIPO. |
| WO 91/02839 | 3/1991 | WIPO. |
| WO 91/05908 | 5/1991 | WIPO. |
| WO 93/25671 | 12/1993 | WIPO. |
| WO 93/25693 | 12/1993 | WIPO. |

OTHER PUBLICATIONS

Éthier, J–F. et al., "Cloning and Characterization of Two Xylanase Genes from Actinomadura sp. FC7, a newly isolated thermophilic actinomycete," Poster presentation at a conference on Gen. Mol. Biol. Indust. Micro. (GMBIM) held in Bloomington, Indiana (Oct. 10–15, 1992).
Bajpai, P. and Bajpai, P. K., "Biobleaching of Kraft Pulp," *Process Biochemistry* 27:319–325 (1992).
Biely, P., "Microbial xylanolytic systems," *Trends Biotechnol.* 3:286–290 (1985).
Boucher et al., "Complete nucleotide sequence of the xylanase gene from the yeast *Crpytococcus albidus*," *Nucleic Acids Res.* 16:9874 (1988).
Dekker, R.F.H., in Hignehi, T., ed., *Biosynthesis and biodegradation of wood components* (Academic Press Inc., Orlando), "Biodegradation of the Hemicelluloses" Chpt. 18, pp. 505–533 (1985).

Éthier, J.–F. et al., "Cloning and Characterization of Two Xylanase Genes from Actinomadura sp. FC7, a newly isolated thermophilic actinomycete," in: *Industrial Microorganisms: Basic and Applied Molecular Genetics*, R. Baltz et al., eds. 1993 (Proc. 5th ASM Conf. on Gen. Mol. Biol. Indust. Micro. (GMBIM) Abst. C25, Am. Soc. Microbiol., Wash. D.C. Oct. 11–15, 1992, Bloomington, Indiana, Poster Session of Oct. 14, 1992.
Éthier, J–F., et al., "Cloning of Two Xylanase Genes from the Newly Isolated Actinomycete Actinomadura sp. FC7 and Characterization of the Gene Products," *Can. J. Microbiol.* 40:362–368 (1994).
Éthier, J–F., *Isolement D'Actinomycetes Thermophiles et Clonage de Genes de Xylanases*. Master's thesis, University of Sherbrooke, Quebec, Canada, Jun., 1992.
Ghangas et al. "Cloning of a *Thermomonospora fusca* Xylanase Gene and its Expression in *Escherichia coli* and *Streptomyces lividans*," *J. of Bacteriol.* 171:2963–2969 (1989).
Gilkes et al., "Domains in Microbial β–1,4–Glycanases: Sequence Conservation, Function, and Enzyme Families," *Microbiol. Rev.* 55:303–315 (1991).
Grabski, A. and Jeffries, W., "Production, Purification, and Characterization of β–(1,4)–Endoxylanase of *Streptomyces roseiscleroticus*." *Appl. Environ. Microbiol.* 57:987–992 (1991).
Grant, R., "Biobleaching review of xylanase pretreatment," *Pulp and Paper Int.* 35:56–57 (1993).
Grépinet et al., "Nucleotide Sequence and Deletion Analysis of the Xylanase Gene (xynZ) of *Clostridium thermocellum*," *J. Bacteriol.* 170:4582–4588 (1988).
Hall et al., "Conserved serine–rich sequences in xylanase and cellulase from *Pseudomonas fluorescens* subspecies *cellulosa*: internal signal sequence and unusual protein processing," *Mol. Microbiol.* 3:1211–1219 (1989).
Hamamoto et al., "Nucleotide Sequence of the Xylanase A Gene of Alkalophilic Bacillus sp. Strain C–125," *Agric. Biol. Chem.* 51:953–955 (1987).
Harpin et al. "Cloning and Characterization of Xylanase Genes from the thermophilic Actinomycete Actinomadura sp. FC 7 and DNA Sequence of One Gene," Paster presentation, SIM/CSM Meeting, Aug. 1, 1993.

(List continued on next page.)

*Primary Examiner*—Robert A. Wax
*Assistant Examiner*—Lisa J. Hobbs
*Attorney, Agent, or Firm*—Sterne, Kessler, Goldstein & Fox, P.L.L.C.

[57] ABSTRACT

The present invention is for a method of chemically treating plant biomass with an enzyme system that retains function at low pH and high temperature. Enzyme preparations enriched in xylanase enzymes which retain activity in low pH and high temperature are described. Such preparations may be utilized in a crude unpurified form, and are especially useful in the production of pulp and paper.

38 Claims, 15 Drawing Sheets

OTHER PUBLICATIONS

Harpin, S., Clonage et Caracterisation de Genes de Xylanases de L'Actinomycete Actinomadura sp. FC 7, Master's thesis, University of Sherbrooke, Quebec, Canada, May, 1993 (This is a translation of the original French document).

Holtz, C. et al., "Production and properties of xylanases from thermophilic actinomycetes," *Antonie van Leeuwenhoek* 59:1–7 (1991).

Ito et al., "Cloning and Sequencing of the xynA Gene Encoding Xylanase A of *Aspergillus kawachii*," *Biosci. Biotec. Biochem.* 56:906–912 (1992).

Kantelinen et al., *1988 TAPPI International Pulp Bleaching Conference*, Tappi Proceedings (1988), pp. 1–9.

Kantelinen et al., "Enzymes in bleaching of kraft pulp," Dissertation for the degree of Doctor of Technology, Technical Research Centre of Finland, VTT Publications 114, Espoo, 1992.

Kellette et al., "Xylanase B and an arabinofuranosidase from *Pseudomonas fluorescens* subsp. *cellulosa* contain identical cellulose–binding domains and are encoded by adjacent genes," *Biochem. J.* 272:369–376 (1990).

Lin, L.–L., Thomson, J.A., "Cloning, sequencing and expression of a gene encoding a 73 kDa xylanase enzyme from the rumen anaerobe *Butyrivibrio fibrisolvens* H17c," *Mol. Gen. Genet.* 228:55–61 (1991).

Lüthi et al., "Cloning, Sequence Analysis, and Expression of Genes Encoding Xylan–Degrading Enzymes from the Thermophile *Caldocellum saccharolyticum*," *Appl. Environ. Microbiol.* 56:1017–1024 (1990).

Lüthi et al., "Xylanase from the Extremely Thermophilic Bacterium *Caldocellum saccharolyticum*:Overexpression of the Gene in *Escherichia coli* and Characterization of the Gene Product," *Appl. Environ. Microbiol.* 56:2677–2683 (1990).

Maat et al., in Visser, J. et al., eds., *Xylans and Xylanases International Symposium: Progress in Biotechnology* 7:349–360 (1992) (Elsevier Science, Amsterdam ISBN:0–444–89477–2).

Myburgh et al., "The Temperature and pH Properties of the Extracellular Hemicellulose–Degrading Enzymes of *Aureobasidium pullulans* NRRL Y 2311-1," *Proc. Biochem.* 26:343–348 (1991).

Onysko, A., "Biological Bleaching of Chemical Pulps: A Review," *Biotech. Adv.* 11:179–198 (1993).

Poutanen et al., "Accessory Enzymes Involved in the Hydrolysis of Xylans," *Enzymes in Biomass Conversion* 33:426–436 (1991).

Scheirlinck et al., "Cloning and expression of cellulase and xylanase genes in *Lactobacillus plantarum*," *Appl Microbiol Biotechnol.* 33:534–541 (1990).

Senior and Hamilton, J. Pulp & Paper., Sep. (1992).

Shareck et al., "Sequences of three genes specifying xylanases in *Streptomyces lividans*," *Gene* 107:75–82 (1991).

Tan et al., "Purification and characterization of a thermostable xylanase from a thermophilic fungus *Thermoascus aurantiacus*," *Can. J. Microbiol.* 33:689–692 (1987).

Vats–Mehta, S. et al., "Cloning of a second xylanase–encoding gene of *Streptomyces lividans* 66," *Gene*, 86:119–122 (1990).

Viikari et al., "Xylanases in bleaching: From an idea to the Industry," *FEMS Microbiology Reviews* 13:335–350 (1994).

Viikari et al., In: Saddler, J. N. (ed.) *Biotechnology in Agriculture* 9:131–182 (1993), Bioconversion of Forest and Agricultural Plant Residues, C–A–B International.

Waldron et al., "Isolation and characterization of a cellulolytic actinomycete *Microbispora bispora*," *Appl. Microbio. Biotech.* 24:477–486 (1986).

Whitehead, T. and Lee, D., "Cloning and Comparison of Xylanase Genes from Ruminal and Colonic Bacteroides Species," *Curr. Microbiol.* 23:15–19 (1991).

Wong et al., "Multiplicity of $\beta$–1,4–Xylanase in Microorganisms: Functions and Applications," *Microbiol. Rev.* 52:305–317 (1988).

Woodward, J., "Xylanases: Functions, Properties and Applications," *Top. Enzyme Ferment. Biotechnol.* 8:9–30 (1984).

World Patent Index, Dialog file 351, Abstract of DE 40 00 558, Kunnas, A. et al., "Paper–Making with Application of Pulp Suspension to a Sieve Wire—With Addition of Enzyme to Recirculation Water Passing Through Wire to Cleave Deleterious Dissolved Substances Such as Hemicellulose".

World Patent Index, Dialog file 351, Abstract of EP 262 040, Fuentes, J. L. et al., "Enzymatic Treatment of Paper Pulp—Using Cellulase and/or Hemicellulase Enzyme Preparation to Improve Draining".

World Patent Index, Dialog file 351, Abstract of EP 334 739, Fuentes, J. L. and Robert, M., "Paper or Cardboard Production—By Enzyme Treatment of Recycled Fibre Pulp to Improve Draining Characteristics".

Zhang et al., "A bifunctional xylanase encoded by the xynA gene of the rumen cellulolytic bacterium *Ruminococcus flavefaciens* 17 comprises two dissimilar domains linked by an asparagine/glutamine–rich sequence," *Mol. Microbiol.* 6:1013–1023 1992.

```
                 NruI
     TCGCGAGGTTGTAGACGTCCAGGGCCTTGCCGCTGTTGCGGTTGACCAGGACGTACCACT
  1  ---------+---------+---------+---------+---------+---------+  60

TGTTCACGTCCACTGTCGCGGCTAGGGCGGCCTGTGTGTTGATCACGGACAAGAGCACCG
 61  ---------+---------+---------+---------+---------+---------+ 120

ACAGCAGGAGCGATGCAATCACCGCCGCACCGGTCCTCAGCATGGACTTCTTCCCTTCGT
121  ---------+---------+---------+---------+---------+---------+ 180

GGGTGAATGTTACCGCTAACATTTCGAGCCGGGCAGAACCTCTTCTCCATCGGCGATTGG
181  ---------+---------+---------+---------+---------+---------+ 240

GGGGAGGTGGTGGTGCGCCGGAGTAAATACGAGGCCGCACGGCTCGTCAAGGGGCAATCT
241  ---------+---------+---------+---------+---------+---------+ 300

CGTCGAAACGTTTCGTATGCAGGTTGCCCTGCCAAACCGCGTGTTCACGCCGGTGATCGG
301  ---------+---------+---------+---------+---------+---------+ 360

-35                    -10
     GCATCTGCCATGAAATATTTTGAAACTATTGACGAACGTTCACGGCCTCACACAATGAGT
361  ---------+---------+---------+---------+---------+---------+ 420

CCTCGACGCCTTGGTGGTGGGCGTTCCGGTGAGGGAACGCGGCGTCTGCTGCACGGCTGT
421  ---------+---------+---------+---------+---------+---------+ 480

RBS           CIT
     GCCCGTGCCCCTTCTTCGCTTCACTCATGGAGGATCAGACGTGCCCATCAACGTCATGCC
481  ---------+---------+---------+---------+---------+---------+ 540
                                             M  P  I  N  V  M  P

CAGGCCCGGAGCCCGCAAGCGGGCTCTTCTCGCCGGCGCCGTCGGACTGCTCACGGCGGC
541  ---------+---------+---------+---------+---------+---------+ 600
      R  P  G  A  R  K  R  A  L  L  A  G  A  V  G  L  L  T  A  A

CGCCGCCCTGGTGGCGCCGTCCCCGGCCGTCGCCGCGGAGAGCACGCTGGGCGCCGCGGC
601  ---------+---------+---------+---------+---------+---------+ 660
      A  A  L  V  A  P  S  P  A  V  A  A  E  S  T  L  G  A  A  A

CGCGCAGAGCGGCCGCTACTTCGGCACCGCCATCGCCTCGGGCCGGCTCAACGACTCGAC
661  ---------+---------+---------+---------+---------+---------+ 720
      A  Q  S  G  R  Y  F  G  T  A  I  A  S  G  R  L  N  D  S  T

GTACACCACGATCGCGAACCGCGAGTTCAACATGGTGACCGCCGAGAACGAGATGAAGAT
721  ---------+---------+---------+---------+---------+---------+ 780
      Y  T  T  I  A  N  R  E  F  N  M  V  T  A  E  N  E  M  K  I
```

FIG. 6

```
     CGACGCCACCGAGCCCAACCGCGGCCAGTTCAACTTCAGCTCCGCCGACCGCATCTACAA
781  ---------+---------+---------+---------+---------+---------+  840
      D  A  T  E  P  N  R  G  Q  F  N  F  S  S  A  D  R  I  Y  N

CTGGGCGGTCCAGAACGGCAAGCAGGTACGCGGCCACACCCTGGCCTGGCACTCCCAGCA
841  ---------+---------+---------+---------+---------+---------+  900
      W  A  V  Q  N  G  K  Q  V  R  G  H  T  L  A  W  H  S  Q  Q

GCCCGGCTGGATGCAGAGCCTCAGCGGCAGCAGCCTGCGCCAGGCGATGATCGACCACAT
901  ---------+---------+---------+---------+---------+---------+  960
      P  G  W  M  Q  S  L  S  G  S  S  L  R  Q  A  M  I  D  H  I

CAACGGCGTCATGGCCCACTACAAGGGCAAGATCGTCCAGTGGGACGTCGTGAACGAGGC
961  ---------+---------+---------+---------+---------+---------+  1020
      N  G  V  M  A  H  Y  K  G  K  I  V  Q  W  D  V  V  N  E  A
```

FIG.6A

| # | Name | Sequence |
|---|---|---|
| 1. | dag | AAGAAGGAGAACGAUCGUG |
| 2. | rep | AAGGGGCGGGAACAUG |
| 3. | XP55 | GUGGGGGAGACAUG |
| 4. | amlV | CAGGAGGAAUCAUG |
| 5. | aml | CAGGAGGCACCACAUG |
| 6. | amySG | CAGGAGGCACCACAUG |
| 7. | ssi | CGGAAGGAUGCACACAAUG |
| 8. | cho | UGAAAGGGCAUACAUG |
| 9. | ermSF | UGAGAGGUGGUCCUCAGUG |
| 10. | amy | GACGAAGGAGCCACAAGAUG |
| 11. | gylR | ACGGAGGCAGUACGUCGAUG |
| 12. | est | UGAAAGGGCACAGCCAUG |
| 13. | korA | UCGAAGGAGUCGUCAUG |
| 14. | aphD | UUGAAGGGUGUGUAAUG |
| 15. | galE | CGAGAGGUAGCGAGUUCAUG |
| 16. | gyl | AAGGAGUCGCGGGUG |
| 17. | cefD | CGGGAGAUGCGUUGACAUG |
| 18. | glnA | UAGGAGGAGCUGGAUG |
| 19. | orfI | AAGGAGUUGAUCGAUG |
| 20. | bla | CAGGAGGUCCGGACAUG |
| 21. | galU | GAGGAGUGCGGCAGUG |
| 22. | afsR | AGGGGGACGGCAUG |
| 23. | orfI590 | CGAGGGGUGGCGCAUG |
| 24. | hyg | AUAGAGGUCCGCUGUG |
| 25. | actIII | AGGGAGGGGAACACAUG |
| 26. | dac | CGGGAGAAGAAUCAGAUG |
| 27. | sapA | AUCGAGGUGCCAUG |
| 28. | tsr | CCGGUAGGACGACCAUG |
| 29. | pAC | AAGGAGACCUUCCAUG |
| 30. | sph | CCCGAGGAAUUCGAUAUG |
| 31. | nshA | GAGGAGGAGGACCCGUG |
| 32. | pIJ101A | CAGGGGGCUCACAUG |
| 33. | tra | CUCGACGACCAUG |
| 34. | aacC7 | CGCGACGCUGAUG |
| 35. | drrAB | CUGGGGGCGUUAGGUG |
| 36. | brpA | GAGGGGGCCGUG |
| 37. | strB | AUGGAGGAGAGUCAUG |
| 38. | Bgal | CGGAAGGCCACGGUCAUG |
| 39. | orfP(erm) | ACGGACACUCGCAUG |
| 40. | npr | CCGCAGAAAGCAUG |
| consensus: | | GGAGGA.....AUG |
| | XlnpJF6 | UGGAGGAUCAGACGUG |

FIG.7

1  MPINVMPRPGARKRALLAGAVGLLTAAAALVAPSPAVAAESTLGAAA  47

FIG.8

| PROMOTERS | REGIONS | |
| --- | --- | --- |
| | -35 | -10 |
| SEP3 | CTCTTGACAACCGCGTAACAGGAGTCATCATATCGCCTAT | |
| redD-prl | GAGTGGTGTAAGCCGTGCACATTGTCATCATGGGCTGCGG | |
| vph-pA1 | CACTGGAATGCCCCTACCACGGTTGGTTGTTCGAAACGGG | |
| xln-pJK6 | CTATTGACGAACGTTCACGGCCTCACACAATGAGTCCTCG | |

FIG.9

```
Psexyna     NgW.......  ...gWedqrs  ciaRstcaaq  pap.fgiVgs  gsstpvssss
Psexynbc    gAWttwQtat  idVdlVqGnn  ivqlsattae  glpnidslSv  vGGtvRagnc
xlnpjf6     ..........  ..........  .....mpinV  MPrpGArk..  Rallag.AvG
Stmxlna     ..........  ..........  .....mgsya  LPrsGvrrSi  RvllaaLvvG
Cficex      ..........  ..........  .MpRttpapg  hParGArtal  RttrrRaAtl
Cloxylz     sdlqalkrhl  lglspltGEa  ILradvnrsg  kvdstdysvl  krylIRiite
Bacxynaa    ..........  ..........  .MitlfRkpf  vagLaisllv  gGGlgnvAaa
Pclotcxl    ..........  ..........  .MNkflnkkw  sl......llt mGGlflMAtl
Cdcxynab    ..........  ..........  ..........  ..........  ..........
Teoendxyla  kAtvkatsdk  dnyiqVndfa  NvNkgeWtel  kgsFtlpVad  ysGlsiyves
Cdccelb     ..........  ......mkr   NLfRivsrvv  LiaFiAsISI  vGamsYFpve
Butxynb     ..........  ..........  ..........  ..........  ..........
Rumlxyna    NqnnwnQnnn  qqnaWngwDn  NnNWnqWggq  nndWnnqqqn  ndwnqWnnqG
Consensus   NAW---Q---  ----WV-G--  NMNR--W--V  LP-FGA--S-  RGGl-R-A-G Psexyna     sslsssSvVs  siRssssSss  ssvAtgNgla  SLAD.Fpigv  aVaAsggnad
Psexynbc    gsvsss...s  svqssssSs   ssAAsAkkfi  ..........  ........gn
xlnpjf6     lltaaaaLVA  pspAvaAEST  lgAAaAqsgR  yFgtAiasg.  .........R
Stmxlna     vlGtataLIA  ppgAhaAEST  lgAAaAqsgR  yFgtAiasg.  .........R
Cficex      vvGatvvLpA  q.....AatT  lkeAadgagR  dFgfALdpn.  .........R
Cloxylz     fpGqgDvqtp  npsvtptqtp  iptisgNaIR  dYAERargiki  gtcvnypfYn
Bacxynaa    QgGppkSgV.  ..Fgenekr.  NdqpfAwqVa  SLsErYqEqF  dlGAAVEPYq
Pclotcxl    ......SLl.  ..FAtGkkaf  NdqtsAedlp  SLAEAFrDYF  plGAAIEPgy
Cdcxynab    ....mrcLI.  ..vcenlEml  N........l  SLAktYKDYF  KIGAAVtakd
Teoendxyla  QnptlEfyld  dfsviGeiSn  NqitiqNdlp  dLysvFKDYF  plGvAVDPsR
Cdccelb     ..........  ..........  tqAApdwslp  SLcEsYKDdF  mlGvAlpaRc
Butxynb     ..........  ..........  .........m  nLktAYepYF  KIGAAIsrWn
Rumlxyna    QqqnnDwnnq  nnWnqGqqnn  NnsAgssd..  SLkgAFskYF  KIGtsVsPhe
Consensus   Q-G--DSLIA  --FA-GAEST  N-AA-AN-IR  SLAEA-KDYF  KIGAAVEPYR

**  *
Psexyna     iftSsarqnl  vraeFNqITA  ENiMKm....  ........sy  mysgSN.FsF
Psexynbc    ittSGavrsd  FtryWNqITp  ENEsKw....  ........gs  vegTrNvYNW
xlnpjf6     LnD.sTYttl  anreFNMVTA  ENEMK.....  ...iDAtePn  rG....QFNF
Stmxlna     LSD.sTYtsl  agreFNMVTA  ENEMK.....  ...iDAtePq  rG....QFNF
Cficex      LSE.aqYkal  adseFNLVvA  ENaMK.....  ...wDAtePs  qn....sFsF
Cloxylz     nSD.pTYnsl  LqreFsMVvc  ENEMK.....  ...fDALQPr  qn....vFdF
Bacxynaa    Le..Grqaql  LKhHYNslvA  ENaMKP....  ....EsLQPr  EG....eWNW
Pclotcxl    tt..Gqiael  YKKHvNMlvA  ENaMKP....  ....asLQPt  EG....nFqW
Cdcxynab    Le..Gvhrdl  LIKHFNslTp  ENaMKf....  ....EnihPe  Eq....rYNF
Teoendxyla  LnDadphaql  taKHFNMlvA  ENaMKP....  ....EsLQPt  EG....nFtF
Cdccelb     LSn.dTdkrm  vIKHFNsITA  ENEMKP....  ....EsLlag  qtsTglsYrF
Butxynb     Lhtpa.htkl  LaeqFNsfTc  ENDMKPmyyL  DreankkdPe  kynlSpaLtF
Rumlxyna    Lnsqa...df  LKKHYNslTp  ENELKPesiL  Dq..gAcQqk  gnnvntQisL
Consensus   LSDSGTY--l  LKKHFNM-TA  ENEMKP---L  D----ALQP-  EG-TSNQFNF
                                              └──┘
```

FIG.10

```
                          *      *    *   *
    Psexyna    tNsDRIVsWA aQNGqtvhGH aLVWHpsyQl PnWa...... ..........
    Psexynbc   aplDRIyaYA rQNnipvkaH TFVW..gaQs PsWL...... ..........
    xlnpjf6    SsADRIynWA VQNGkqvRGH TLaWHs..Qq PgWM..qs.. ..........
    Stmxlna    SsADRVynWA VQNGkqvRGH TLaWHs..Qq PgWM..qs.. ..........
    Cficex     gagDRVasYA adtGkeLyGH TLVWHs..Ql PDWa...kn. ..........
    Cloxylz    SkgDqllaFA erNGMqMRGH TLIWHN..Qn PsWLtngn.. ..........
    Bacxynaa   egADkIVEFA rkhnMeLRfH TLVWHs..Qv PEWFFiDedG nrMVDETDPd
    Pclotcxl   adADRIVqFA keNGMeLRfH TLVWHN..QT PtgFsLDkeG kpMVEETDPq
    Cdcxynab   eevaRIkEFA IkNdMkLRGH TFVWHN..QT PgWvFLDknG e.........
    Teoendxyla dNADkIVDYA IahnMkMRGH TLIWHN..Qv PDWFFqDpsd .........p
    Cdccelb    StADafVDFA stNkigiRGH TLVWHN..QT PDWFFkDsnG qrL.......
    Butxynb    eNAipylEFA kdNkiaMRGH TLVWHN..QT PkWFFcEryn enF.......
    Rumlxyna   SrAaqtlkFc eQNGiaLRGH TFVWys..QT PDWFFrEnfs qn........
    Consensus  SNADRIVEFA -QNGM-LRGH TLVWHN--QT PDWFFLD--G --MV-ETDP-
                                 └─────────┘

Psexyna    .sD.SnanFr QdFarHldTV aaHF...... aGqVkSWDVV NEAIFdsadd
    Psexynbc   .nnISgpeva veiEqwIrdy carY...... Pdtami.DVV NEAv......
    xlnpjf6    ...ISgssLr QaMidHIngV MaHYK..... .GKIvqWDVV NEAF......
    Stmxlna    ...ISgrpLr QaMidHIngV MaHYK..... .GKIvqWDVV NEAF......
    Cficex     ...IngsaFe saMvNHVtkV adHFe..... .GKVaSWDVV NEAF......
    Cloxylz    ...wnrDsLL avMkNHItTV MtHYK..... .GKIveWDVa NEcM......
    Bacxynaa   KREankqLLL eRMENHIkTV verYK..... .ddVtSWDVV NEvi......
    Pclotcxl   KREenrkLLL QRLENyIraV vlrYK..... .ddIkSWDVV NEvi......
    Cdcxynab   ..EaSkELvi eRLreHIkTI cerYK..... .dvVyaWDVV NEAv......
    Teoendxyla sksaSrDLLL QRLktHItTV LdHFKTkYgs qnpIIigWDVV NEvL......
    Cdccelb    ....SkDaLL aRLkqyIydV vgrYK..... .GKVyaWDVV NEAi......
    Butxynb    .pmadrEtiL aRLEsyIhgV LdfvqTnY.. PGilyaWDVV NEiv......
    Rumlxyna   gayvSkDiMn QRLEsmIknt FaaLKsqYpn Id.VySYDVc NEIFL.....
    Consensus  KRE-S-DLLL QRLENHI-TV M-HYKT-Y-- PGK--SWDVV NEAF------
                                                    └──────┘
                          *     *                    *  **
    Psexyna    pdGrgsaNGy rqsvfYrQfg GpE.YIDeAF RRApr.ADPt AeLYYNDFNt
    Psexynbc   .pGhqpa.Gy aqRaf..... GNn.WIqrvF qIARq.ycPn siLiINDYNn
    xlnpjf6    ...aDGnsGG .RRdsnIQrt GND.WIEVAF RtARn.ADPn AKLCYNDYNi
    Stmxlna    ...aDGssGa .RRdsnIQrs GND.WIEVAF RtARa.ADPs AKLCYNDYNv
    Cficex     ...aDGDgpp .qdSaFqQkl GNg.YIEtAF RaARa.ADPt AKLCiNDYNv
    Cloxylz    ...DDsgNGl .RsSiWrnVl GqD.YIDyAF RYARE.ADPD AILFYNDYNi
    Bacxynaa   ...D..DgGG LReSeWyQIt GtD.YIkVAF etARkYggeE AKLYiNDYNt
    Pclotcxl   ...EpnDpGG MRnSpWyQIt GtE.YIEVAF RatREaggsD iKLYiNDYNt
    Cdcxynab   ...EDktekl LReSnWrkII GdD.YIkIAF eiAREYAg.D AKLFYNDYNn
    Teoendxyla ...D..DNGn LRnSkWIQII GpD.YIEkAF eYAhE.ADPs mKLFiNDYNi
    Cdccelb    ...DEnqpds yRRStWyeIc GpE.YIEkAF iWAhE.ADPn AKLFYNDYNt
    Butxynb    ...D...eGa FRkSiWtetV GeD.FfikAF eFARkYAaPE vsLFYNDYet
    Rumlxyna   ..nngGgmrG adnSnWvkly GdDsFVinAF kYARqYApag cKLYINDYN.
    Consensus  --GDDGDNGG LRRS-W-QII GND-YIEVAF RYAREYADPD AKLFYNDYN-
                                                                 └─
```

FIG.10A

```
              *   *  *
Psexyna    Eeng.AKTtA  LvNLVqrLIn  nGVPIDGVGF  QmHvMndY..  .....PslaNi
Psexynbc   irWq.hn...  ..eFlalaKa  qGnyIDaVGL  QaHeLkgmta  aqvktaIdNi
xInpjf6    EnWnWAKTqg  vYNMVrDFKq  RGVPIDcVGF  QSH....FNs  G..sPYnSNf
Stmxlna    EnWtWAKTqA  MYNMVrDFKq  RGVPIDcVGF  QSH....FNs  G..sPYnSNf
Cficex     Egin.AKsns  LYdIVKDFKa  RGVPIDcVGF  QSH....LiV  G...qvpgdf
Cloxylz    Edlg.pKsnA  vFNMIKsMKE  RGVPIDGVGF  QcH....Fin  GmsPeYlasi
Bacxynaa   E.vPs.KrDd  LYNLVKDLIE  qGVPIDGVGh  QSH....iql  G.WPs.ledt
Pclotcxl   D.dPv.KrDi  LYeLVKnLIE  kGVPIDGVGh  QtH....idI  y.nPP.Veri
Cdcxynab   E.mPY.KIEk  tYkvIKELIE  RGtPIDGIGi  QaH....WNI  w.dknIVSNI
Teoendxyla Enngv.KTqA  MYdLVKkLKs  eGVPIDGIGM  QmH....iNI  ...nsnIdNi
Cdccelb    E.isk.KrDf  iYNMVKnLKs  kGIPIhGIGM  QcH....iNV  n.WPs.VSei
Butxynb    a.qPW.KrDf  iLekVIgpli  dkkIIDGmGM  QSH....LIm  d.hPd.ISey
Rumlxyna   .eYipAKTnd  iYNMamkLKq  IGy.IDGIGM  QSHIatnY..  .....Pdanty
Consensus  E-WPWAKTDA  LYN-VKDLKE  RGVPIDGVGF  QSH----FNI  G-WPPYISN-
           ⌐        ⌐           ⌐          ⌐
                          *
Psexyna    RqaMqKivaL  SptIkIkITE  LDVrLnNpyD  gnssndYtnr  ndcaVscagL
Psexynbc   WnqvgKpiyi  S.eyDIgdTn  dqVqLqN...  ..........  ..........
xInpjf6    RTtLqnFAaL  ..GvDValTE  LDIq......  ..........  ..........
Stmxlna    RTtLqnFAaL  ..GvDValTE  LDIq......  ..........  ..........
Cficex     RqnLqrFAdL  ..GvDVrITE  LDIrM.....  .....rtps.  ....d.atkL
Cloxylz    dqnikrYAei  ..GviVsfTE  iDIri.....  .....pqsE.  .....nPataF
Bacxynaa   RasFeKFtSL  ..GIDnqVTE  LDmSLYgWpp  tgaYtsYDD.  .....IPaELL
Pclotcxl   iesikKFAgL  ..GIDniITE  LDmSiYsWnD  rsdYg..Ds.  .....IPdyiL
Cdcxynab   kkaievYASL  ..GIEIhITE  LDISvFeFeD  krt.dIFEp.  ....tPe.ML
Teoendxyla kasieKLASL  ..GvEIqVTE  LDmnMng...  .........n  ....IsnEaL
Cdccelb    ensikIFsSi  .pGiEIhITE  LDmSLYNYgs  senYs...t.  .....pPqDLL
Butxynb    RTaLemYgS.  .tGIqIhITE  LDmh......  .......naD.  ....pseEsM
Rumlxyna   eTaLkKF..L  StGIEVqITE  LDIt......  ..........  ..........
Consensus  RT-L-KFASL  S-G-DI-ITE  LDISLYNW-D  ---Y--YDD-  ----IP-ELL
                                  ⌐        ⌐
                                      *
Psexyna    drQkARYKEi  vqAYLeVvpp  grrg...gITv  WGIaDpdSWL  ythqnIpDW.
Psexynbc   ..........  FqAhFpVfyn  hphV..hgit  sGIcggqdl.  .......DR.
xInpjf6    gAspttYanv  vndCLAVSr.  ....clgITv  WGVrD.....  tdsWRsDq..
Stmxlna    gApAstYanv  tndCLAVSr.  ....clgITv  WGVrD.....  SdsWRsEq..
Cficex     atQAAdYKkv  vqACMqVtr.  ....cqgVTv  WGItDkYSWv  pdvFpgEg..
Cloxylz    QvQAnnYKEI  mkiCLAnpn.  ....cntfvM  WGftDkYtWi  pGtFpgyg..
Bacxynaa   QAQAdRYdql  FeIY....eE  laAdIssVTF  WGIaDnhtWL  dGraReynng
Pclotcxl   tIQAkRYqEI  FdAI....kE  nKdIVsaVvF  WGISDkYSWL  nGFpvKrtn.
Cdcxynab   eIQAkvYeDv  FavF....rE  yKdVITsVTL  WGISDrhtWk  dnFpvKgrkd
Teoendxyla IkQArIYKqI  FdIF....ka  eKqyITaVvF  WGVSDdvtWL  Sk........
Cdccelb    QkQsqkYKEi  FtmI....kk  yKnVVksVTF  WGIkDdYSWL  rsFYgKnDW.
Butxynb    hAIAtRYqEf  FqtYLdakks  gKanITsVTF  WnIIDenSWL  SGFRRetsY.
Rumlxyna   ctnsAeQaDI  YekiFklamq  nsAqIpaVTi  WGtqDtvSWr  Ss........
Consensus  QAQAARYKE-  F-ACLAVS-E  -KAVIT-VTF  WGISD-YSWL  SGF-RKEDW-
```

FIG.10B

```
Psexyna    .....PLLFn  dNLQPKPAYq  gVvEALsGr.  ..........  ..........
Psexynbc   .....rLrFD  pgqwhtapgn  dVvDX.....  ..........  ..........
xlnpjf6    ....tPLLFD  gNgnkKaAYs  AVlnALnGgg  TSEP......  PPasdAgtik
Stmxlna    ....tPLLFn  ndgskKaAYt  AVIDALnGgd  sSEP......  Pa..dggqik
Cficex     ....AaLvWD  asYakKPAYa  AVmEAFgasp  TptPttptpt  PtTPtptPts
Cloxylz    ....nPLiYD  sNYnPKPAYn  AlkEALmGyX  ..........  ..........
Bacxynaa   vgidAPFvFD  hNYrvKPAYW  rliDX.....  ..........  ..........
Pclotcxl   ....APLLFD  rNFmPKPAFW  AlvDpsrIre  X.........  ..........
Cdcxynab   w....PLLFD  vNgkPKeALY  rIlrfX....  ..........  ..........
Teoendxyla ..pnAPLLFD  skLQaKPAFW  AVvDpskaip  diqsakaleg  sPTigAnvds
Cdccelb    .....PLLFf  edYsaKPAYW  AViEAsgvtt  ..........s sPTPtptPtv
Butxynb    .....PLvFk  gkceaKeAYY  AVlkA.....  ..........  .....Avsdd
Rumlxyna   ...qnPLLFs  agYQPKPAYd  rVmalakX..  ..........  ..........
Consensus  ----APLLFD  -NYQPKPAYW  AV-DAL-G--  TSEP------  PPTP-A-P--
                ‾‾‾‾‾

Psexyna    ..........  ..........  ..........  ..........  ..........
Psexynbc   ..........  ..........  ..........  ..........  ..........
xlnpjf6    GVGSGRcL.D  VPnaSTsDGv  qlqlwdchgg  TNQQWTyTdS  qElrvYGNKc
Stmxlna    GVGSGRcL.D  VPDaSTsDGt  qlqlwdchsg  TNQQWaaTda  gElrvYGdKc
Cficex     GpagcqvLWg  VnqwnTgfta  nvTVKntssa  pvdgWTITfS  fpsgqqvtqa
Cloxylz    ..........  ..........  ..........  ..........  ..........
Bacxynaa   ..........  ..........  ..........  ..........  ..........
Pclotcxl   ..........  ..........  ..........  ..........  ..........
Cdcxynab   ..........  ..........  ..........  ..........  ..........
Teoendxyla swklvkpLYv  ntyvegtvGa  TaTVKsmwdt  kNlyllvqvS  dntpsnndgi
Cdccelb    tVtptptptp  tPtvtatptp  TpTpvstpat  ggQikvlyan  kEtnsttNti
Butxynb    sIdkwvpdYs  eeDyklqgmp  TpdIKrfren  iwQeneynye  asygfipNlf
Rumlxyna   ..........  ..........  ..........  ..........  ..........
Consensus  GVGSGR-LYD  VPD-ST-DG-  T-TVK-----  TNQQWT-T-S  -E---YGNK-
```

FIG.10C

```
Xln A:   1 MGSYALPRSGVRRSIRVLLAALVVGVLGTATALIAPPGAHAAESTLGAAA 50
           |.  .:||.|.|:   |.|||:  .||:|..|.||:||..|  |||||||||||
pJF6 :   1 MPINVMPRPGARK..RALLAG.AVGLLTAAAALVAPSPAVAAESTLGAAA 47

51 AQSGRYFGTAIASGRLSDSTYTSIAGREFNMVTAENEMKIDATEPQRGQF 100
           ||||||||||||||||.|||||.||.||||||||||||||||||.||||
        48 AQSGRYFGTAIASGRLNDSTYTTIANREFNMVTAENEMKIDATEPNRGQF 97

101 NFSSADRVYNWAVQNGKQVRGHTLAWHSQQPGWMQSLSGRPLRQAMIDHI 150
           |||||||:|||||||||||||||||||||||||||||..|||||||||
        98 NFSSADRIYNWAVQNGKQVRGHTLAWHSQQPGWMQSLSGSSLRQAMIDHI 147

151 NGVMAHYKGKIVQWDVVNEAFADGSSGARRDSNLQRSGNDWIEVAFRTAR 200
           |||||||||||||||||||||||||.||:|||||||||.|||||||||||||
       148 NGVMAHYKGKIVQWDVVNEAFADGNSGGRRDSNLQRTGNDWIEVAFRTAR 197

201 AADPSAKLCYNDYNVENWTWAKTQAMYNMVRDFKQRGVPIDCVGFQSHFN 250
           .|||.||||||||||:|||.|||||::||||||||||||||||||||||
       198 NADPNAKLCYNDYNIENWNWAKTQGVYNMVRDFKQRGVPIDCVGFQSHFN 247

251 SGSPYNSNFRTTLQNFAALGVDVAITELDIQGAPASTYANVTNDCLAVSR 300
           |||||||||||||||||||||||||||||||.:.||||.||||||||
       248 SGSPYNSNFRTTLQNFAALGVDVAITELDIQGASPTTYANVVNDCLAVSR 297

301 CLGITVWGVRDSDSWRSEQTPLLFNNDGSKKAAYTAVLDALNGGDSSEPP 350
           ||||||||||.|||||:|||||::.|.||||.|||:|||||:..||||
       298 CLGITVWGVRDTDSWRSDQTPLLFDGNGNKKAAYSAVLNALNGGGTSEPP 347

351 A..DGGQIKGVGSGRCLDVPDASTSDGTQLQLWDCHSGTNQQWAATDAGE 398
           :  |:| ||||||||||||:||||||.||||||:||||||. ||..|
       348 PASDAGTIKGVGSGRCLDVPNASTSDGVQLQLWDCHGGTNQQWTYTDSQE 397

399 LRVYGDKCLDAAGTSNGSKVQI 420
           |||||:|||||||:||.||||
       398 LRVYGNKCLDAAGTGNGTKVQI 419
```

FIG. 11

1538 GGCGGCGGCACCTCCGAGCCGCCGCCCGCCTCCGACGCCGGGACGATCAAGGGCGTCGG

CTCGGCCGCTGCCTGGACGTGCCCAACGCCAGCACCAGCGACGGCGT

CCAGCTCCAGCTGTGGGACTGCCACGGC 1672

FIG.12

```
          C  T TT  T                           S
          ↓  ↓ ↓↓  ↓                           ↓
Xln A:  1 MGSYALPRSGVRRSIRVLLAALVVGVLGTATALIAPPGAHAAESTLGAAA  50
pJF6 :  1 MPINVMPRPGARK..RALLAG.AVGLLTAAAALVAPSPAVAAESTLGAAA   47
            ↑ ↑↑↑ ↑                           ↑
            T TT  T                           S

TCC        T     C    TSC      SST    S T  C
           ↓↓↓        ↓     ↓    ↓↓↓      ↓↓↓    ↓ ↓  ↓
 51 AQSGRYFGTAIASGRLSDSTYTSIAGREFNMVTAENEMKIDATEPQRGQF 100
 48 AQSGRYFGTAIASGRLNDSTYTTIANREFNMVTAENEMKIDATEPNRGQF  97
    ↑↑↑             ↑ ↑↑↑   ↑↑↑            ↑ ↑  ↑ ↑
    TCC             T  TSC   C              S S T  S T C

C   TCC    TT   C      C        T T
        ↓   ↓↓↓    ↓↓   ↓      ↓        ↓ ↓
101 NFSSADRVYNWAVQNGKQVRGHTLAWHSQQPGWMQSLSGRPLRQAMIDHI 150
 98 NFSSADRIYNWAVQNGKQVRGHTLAWHSQQPGWMQSLSGSSLRQAMIDHI 147
        ↑   ↑↑↑    ↑↑   ↑      ↑        ↑
        C   TCC    TT   C      C        T

CT T   C   S C     TT    T   C S  CT  T
         ↓↓ ↓   ↓   ↓ ↓     ↓↓    ↓   ↓ ↓  ↓↓  ↓
151 NGVMAHYKGKIVQWDVVNEAFADGSSGARRDSNLQRSGNDWIEVAFRTAR 200
148 NGVMAHYKGKIVQWDVVNEAFADGNSGGRRDSNLQRTGNDWIEVAFRTAR 197
         ↑↑ ↑   ↑   ↑ ↑     ↑↑    ↑   ↑ ↑  ↑↑  ↑
         CT T   C   S C     TT    T   C S  CT  T

T C  C SCC T    C   T CT T       C  C
          ↓ ↓  ↓ ↓↓↓ ↓    ↓   ↓ ↓↓ ↓       ↓  ↓
201 AADPSAKLCYNDYNVENWTWAKTQAMYNMVRDFKQRGVPIDCVGFQSHFN 250
198 NADPNAKLCYNDYNIENWNWAKTQGVYNMVRDFKQRGVPIDCVGFQSHFN 247
          ↑ ↑  ↑ ↑↑↑ ↑    ↑   ↑ ↑↑↑         ↑  ↑
          T C  C SCC T    C   T CT T       C  C

T CT    C       S        C           T
       ↓ ↓↓    ↓       ↓        ↓           ↓
251 SGSPYNSNFRTTLQNFAALGVDVAITELDIQCAPASTYANVTNDCLAVSR 300
248 SGSPYNSNFRTTLQNFAALGVDVAITELDIQCASPTTYANVVNDCLAVSR 297
       ↑ ↑↑    ↑       ↑        ↑           ↑
       T CT    C       S        C           T
```

FIG.13

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
        ( A ) LENGTH: 1020 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 521..1020

( x i ) SEQUENCE DESCRIPTION: SEQ ID NO:1:

```
TCGCGAGGTT  GTAGACGTCC  AGGGCCTTGC  CGCTGTTGCG  GTTGACCAGG  ACGTACCACT      60

TGTTCACGTC  CACTGTCGCG  GCTAGGGCGG  CCTGTGTGTT  GATCACGGAC  AAGAGCACCG     120

ACAGCAGGAG  CGATGCAATC  ACCGCCGCAC  CGGTCCTCAG  CATGGACTTC  TTCCCTTCGT     180

GGGTGAATGT  TACCGCTAAC  ATTTCGAGCC  GGGCAGAACC  TCTTCTCCAT  CGGCGATTGG     240

GGGGAGGTGG  TGGTGCGCCG  GAGTAAATAC  GAGGCCGCAC  GGCTCGTCAA  GGGGCAATCT     300

CGTCGAAACG  TTTCGTATGC  AGGTTGCCCT  GCCAAACCGC  GTGTTCACGC  CGGTGATCGG     360

GCATCTGCCA  TGAAATATTT  TGAAACTATT  GACGAACGTT  CACGGCCTCA  CACAATGAGT     420

CCTCGACGCC  TTGGTGGTGG  GCGTTCCGGT  GAGGGAACGC  GGCGTCTGCT  GCACGGCTGT     480

GCCCGTGCCC  CTTCTTCGCT  TCACTCATGG  AGGATCAGAC  GTG  CCC  ATC  AAC  GTC     535
                                                Met  Pro  Ile  Asn  Val
                                                 1                    5

ATG  CCC  AGG  CCC  GGA  GCC  CGC  AAG  CGG  GCT  CTT  CTC  GCC  GGC  GCC  GTC     583
Met  Pro  Arg  Pro  Gly  Ala  Arg  Lys  Arg  Ala  Leu  Leu  Ala  Gly  Ala  Val
               10                        15                        20

GGA  CTG  CTC  ACG  GCG  GCC  GCC  GCC  CTG  GTG  GCG  CCG  TCC  CCG  GCC  GTC     631
Gly  Leu  Leu  Thr  Ala  Ala  Ala  Ala  Leu  Val  Ala  Pro  Ser  Pro  Ala  Val
                25                        30                        35

GCC  GCG  GAG  AGC  ACG  CTG  GGC  GCC  GCG  GCC  GCG  CAG  AGC  GGC  CGC  TAC     679
Ala  Ala  Glu  Ser  Thr  Leu  Gly  Ala  Ala  Ala  Ala  Gln  Ser  Gly  Arg  Tyr
           40                        45                        50

TTC  GGC  ACC  GCC  ATC  GCC  TCG  GGC  CGG  CTC  AAC  GAC  TCG  ACG  TAC  ACC     727
Phe  Gly  Thr  Ala  Ile  Ala  Ser  Gly  Arg  Leu  Asn  Asp  Ser  Thr  Tyr  Thr
      55                        60                        65

ACG  ATC  GCG  AAC  CGC  GAG  TTC  AAC  ATG  GTG  ACC  GCC  GAG  AAC  GAG  ATG     775
Thr  Ile  Ala  Asn  Arg  Glu  Phe  Asn  Met  Val  Thr  Ala  Glu  Asn  Glu  Met
 70                        75                        80                   85

AAG  ATC  GAC  GCC  ACC  GAG  CCC  AAC  CGC  GGC  CAG  TTC  AAC  TTC  AGC  TCC     823
Lys  Ile  Asp  Ala  Thr  Glu  Pro  Asn  Arg  Gly  Gln  Phe  Asn  Phe  Ser  Ser
                     90                        95                       100

GCC  GAC  CGC  ATC  TAC  AAC  TGG  GCG  GTC  CAG  AAC  GGC  AAG  CAG  GTA  CGC     871
Ala  Asp  Arg  Ile  Tyr  Asn  Trp  Ala  Val  Gln  Asn  Gly  Lys  Gln  Val  Arg
               105                       110                       115
```

```
GGC CAC ACC CTG GCC TGG CAC TCC CAG CAG CCC GGC TGG ATG CAG AGC      919
Gly His Thr Leu Ala Trp His Ser Gln Gln Pro Gly Trp Met Gln Ser
        120                     125                 130

CTC AGC GGC AGC AGC CTG CGC CAG GCG ATG ATC GAC CAC ATC AAC GGC      967
Leu Ser Gly Ser Ser Leu Arg Gln Ala Met Ile Asp His Ile Asn Gly
    135                     140                     145

GTC ATG GCC CAC TAC AAG GGC AAG ATC GTC CAG TGG GAC GTC GTG AAC     1015
Val Met Ala His Tyr Lys Gly Lys Ile Val Gln Trp Asp Val Val Asn
150                     155                 160                 165

GAG GC                                                              1020
Glu Ala
```

( 2 ) INFORMATION FOR SEQ ID NO:2:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Ile Asn Val Met Pro Arg Pro Gly Ala Arg Lys Arg Ala Leu
 1               5                  10                  15

Leu Ala Gly Ala Val Gly Leu Leu Thr Ala Ala Ala Leu Val Ala
                20              25                  30

Pro Ser Pro Ala Val Ala Ala Glu Ser Thr Leu Gly Ala Ala Ala Ala
            35                  40                  45

Gln Ser Gly Arg Tyr Phe Gly Thr Ala Ile Ala Ser Gly Arg Leu Asn
        50              55                  60

Asp Ser Thr Tyr Thr Thr Ile Ala Asn Arg Glu Phe Asn Met Val Thr
65                      70                  75                  80

Ala Glu Asn Glu Met Lys Ile Asp Ala Thr Glu Pro Asn Arg Gly Gln
                85                  90                  95

Phe Asn Phe Ser Ser Ala Asp Arg Ile Tyr Asn Trp Ala Val Gln Asn
            100                 105                 110

Gly Lys Gln Val Arg Gly His Thr Leu Ala Trp His Ser Gln Gln Pro
        115                 120                 125

Gly Trp Met Gln Ser Leu Ser Gly Ser Ser Leu Arg Gln Ala Met Ile
    130                 135                 140

Asp His Ile Asn Gly Val Met Ala His Tyr Lys Gly Lys Ile Val Gln
145                 150                 155                 160

Trp Asp Val Val Asn Glu Ala
                165
```

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: both
        ( D ) TOPOLOGY: both ( x i ) SEQUENCE DESCRIPTION: SEQ ID NO:3:

```
AAGAAGGAGA ACGAUCGUG                                                  19
```

( 2 ) INFORMATION FOR SEQ ID NO:4:

( i ) SEQUENCE CHARACTERISTICS:
        ( A ) LENGTH: 16 base pairs
        ( B ) TYPE: nucleic acid (C) STRANDEDNESS: both
(D) TOPOLOGY: both (xi) SEQUENCE DESCRIPTION: SEQ ID NO:4:

AAGGGGCGGG AACAUG   16

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: both
        (D) TOPOLOGY: both (xi) SEQUENCE DESCRIPTION: SEQ ID NO:5:

GUGGGGGAGA CAUG   14

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: both
        (D) TOPOLOGY: both (xi) SEQUENCE DESCRIPTION: SEQ ID NO:6:

CAGGAGGAAU CAUG   14

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: both
        (D) TOPOLOGY: both (xi) SEQUENCE DESCRIPTION: SEQ ID NO:7:

CAGGAGGCAC CACAUG   16

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: both
        (D) TOPOLOGY: both (xi) SEQUENCE DESCRIPTION: SEQ ID NO:8:

CAGGAGGCAC CACAUG   16

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: both
        (D) TOPOLOGY: both (xi) SEQUENCE DESCRIPTION: SEQ ID NO:9:

CGGAAGGAUG CACACAAUG   19

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: both
        (D) TOPOLOGY: both ( x i ) SEQUENCE DESCRIPTION: SEQ ID NO:10:

UGAAAGGGCA UACAUG 16

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: both
        ( D ) TOPOLOGY: both ( x i ) SEQUENCE DESCRIPTION: SEQ ID NO:11:

UGAGAGGUGG UCCUCAGUG 19

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: both ( x i ) SEQUENCE DESCRIPTION: SEQ ID NO:12:

GACGAAGGAG CCACAAGAUG 20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: both ( x i ) SEQUENCE DESCRIPTION: SEQ ID NO:13:

ACGGAGGCAG UACGUCGAUG 20

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: both ( x i ) SEQUENCE DESCRIPTION: SEQ ID NO:14:

UGAAAGGGCA CAGCCAUG 18

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:15:

UCGAAGGAGU CGUCAUG 17

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:16:

UUGAAGGGUG UGUAAUG                                                                      17

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: both ( x i ) SEQUENCE DESCRIPTION: SEQ ID NO:17:

CGAGAGGUAG CGAGUUCAUG                                                                   20

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: both ( x i ) SEQUENCE DESCRIPTION: SEQ ID NO:18:

AAGGAGUCGC GGGUG                                                                        15

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: both
        ( D ) TOPOLOGY: both ( x i ) SEQUENCE DESCRIPTION: SEQ ID NO:19:

CGGGAGAUGC GUUGACAUG                                                                    19

( 2 ) INFORMATION FOR SEQ ID NO:20:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: both ( x i ) SEQUENCE DESCRIPTION: SEQ ID NO:20:

UAGGAGGAGC UGGAUG                                                                       16

( 2 ) INFORMATION FOR SEQ ID NO:21:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: both ( x i ) SEQUENCE DESCRIPTION: SEQ ID NO:21:

AAGGAGUUGA UCGAUG                                                                       16

( 2 ) INFORMATION FOR SEQ ID NO:22:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:22:

CAGGAGGUCC GGACAUG                                                                      17

( 2 ) INFORMATION FOR SEQ ID NO:23:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: both ( x i ) SEQUENCE DESCRIPTION: SEQ ID NO:23:

GAGGAGUGCG GCAGUG    16

( 2 ) INFORMATION FOR SEQ ID NO:24:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: both ( x i ) SEQUENCE DESCRIPTION: SEQ ID NO:24:

AGGGGGACGG CAUG    14

( 2 ) INFORMATION FOR SEQ ID NO:25:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: both ( x i ) SEQUENCE DESCRIPTION: SEQ ID NO:25:

CGAGGGUGG CGCAUG    16

( 2 ) INFORMATION FOR SEQ ID NO:26:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: both ( x i ) SEQUENCE DESCRIPTION: SEQ ID NO:26:

AUAGAGGUCC GCUGUG    16

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:27:

AGGGAGGGGA ACACAUG    17

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: both ( x i ) SEQUENCE DESCRIPTION: SEQ ID NO:28:

CGGGAGAAGA AUCAGAUG    18

( 2 ) INFORMATION FOR SEQ ID NO:29:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: both ( x i ) SEQUENCE DESCRIPTION: SEQ ID NO:29:

AUCGAGGUGC CAUG              14

( 2 ) INFORMATION FOR SEQ ID NO:30:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:30:

CCGGUAGGAC GACCAUG          17

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: both ( x i ) SEQUENCE DESCRIPTION: SEQ ID NO:31:

AAGGAGACCU UCCAUG           16

( 2 ) INFORMATION FOR SEQ ID NO:32:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: both ( x i ) SEQUENCE DESCRIPTION: SEQ ID NO:32:

CCCGAGGAAU UCGAUAUG         18

( 2 ) INFORMATION FOR SEQ ID NO:33:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:33:

GAGGAGGAGG ACCCGUG          17

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: both ( x i ) SEQUENCE DESCRIPTION: SEQ ID NO:34:

CAGGGGCUC ACAUG            15

( 2 ) INFORMATION FOR SEQ ID NO:35:

( i ) SEQUENCE CHARACTERISTICS:
   ( A ) LENGTH: 13 base pairs
   ( B ) TYPE: nucleic acid
   ( C ) STRANDEDNESS: both
   ( D ) TOPOLOGY: both ( x i ) SEQUENCE DESCRIPTION: SEQ ID NO:35:

CUCGACGACC AUG  13

( 2 ) INFORMATION FOR SEQ ID NO:36:

( i ) SEQUENCE CHARACTERISTICS:
      ( A ) LENGTH: 13 base pairs
      ( B ) TYPE: nucleic acid
      ( C ) STRANDEDNESS: both
      ( D ) TOPOLOGY: both ( x i ) SEQUENCE DESCRIPTION: SEQ ID NO:36:

CGCGACGCUG AUG  13

( 2 ) INFORMATION FOR SEQ ID NO:37:

( i ) SEQUENCE CHARACTERISTICS:
      ( A ) LENGTH: 16 base pairs
      ( B ) TYPE: nucleic acid
      ( C ) STRANDEDNESS: both
      ( D ) TOPOLOGY: both ( x i ) SEQUENCE DESCRIPTION: SEQ ID NO:37:

CUGGGGGCGU UAGGUG  16

( 2 ) INFORMATION FOR SEQ ID NO:38:

( i ) SEQUENCE CHARACTERISTICS:
      ( A ) LENGTH: 12 base pairs
      ( B ) TYPE: nucleic acid
      ( C ) STRANDEDNESS: both
      ( D ) TOPOLOGY: both ( x i ) SEQUENCE DESCRIPTION: SEQ ID NO:38:

GAGGGGGCCG UG  12

( 2 ) INFORMATION FOR SEQ ID NO:39:

( i ) SEQUENCE CHARACTERISTICS:
      ( A ) LENGTH: 16 base pairs
      ( B ) TYPE: nucleic acid
      ( C ) STRANDEDNESS: both
      ( D ) TOPOLOGY: both ( x i ) SEQUENCE DESCRIPTION: SEQ ID NO:39:

AUGGAGGAGA GUCAUG  16

( 2 ) INFORMATION FOR SEQ ID NO:40:

( i ) SEQUENCE CHARACTERISTICS:
      ( A ) LENGTH: 18 base pairs
      ( B ) TYPE: nucleic acid
      ( C ) STRANDEDNESS: both
      ( D ) TOPOLOGY: both ( x i ) SEQUENCE DESCRIPTION: SEQ ID NO:40:

CGGAAGGCCA CGGUCAUG  18

( 2 ) INFORMATION FOR SEQ ID NO:41:

( i ) SEQUENCE CHARACTERISTICS:
      ( A ) LENGTH: 15 base pairs ( B ) TYPE: nucleic acid
        ( C ) STRANDEDNESS: both
        ( D ) TOPOLOGY: both ( x i ) SEQUENCE DESCRIPTION: SEQ ID NO:41:

ACGGACACUC GCAUG 15

( 2 ) INFORMATION FOR SEQ ID NO:42:

( i ) SEQUENCE CHARACTERISTICS:
        ( A ) LENGTH: 14 base pairs
        ( B ) TYPE: nucleic acid
        ( C ) STRANDEDNESS: both
        ( D ) TOPOLOGY: both ( x i ) SEQUENCE DESCRIPTION: SEQ ID NO:42:

CCGCAGAAAG CAUG 14

( 2 ) INFORMATION FOR SEQ ID NO:43:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: both ( x i ) SEQUENCE DESCRIPTION: SEQ ID NO:43:

UGGAGGAUCA GACGUG 16

( 2 ) INFORMATION FOR SEQ ID NO:44:

( i ) SEQUENCE CHARACTERISTICS:
        ( A ) LENGTH: 47 amino acids
        ( B ) TYPE: amino acid
        ( C ) STRANDEDNESS: both
        ( D ) TOPOLOGY: both ( x i ) SEQUENCE DESCRIPTION: SEQ ID NO:44:

Met Pro Ile Asn Val Met Pro Arg Pro Gly Ala Arg Lys Arg Ala Leu
        1               5                   10                  15

Leu Ala Gly Ala Val Gly Leu Leu Thr Ala Ala Ala Ala Leu Val Ala
                        20                  25                  30

Pro Ser Pro Ala Val Ala Ala Glu Ser Thr Leu Gly Ala Ala Ala
                    35                  40                  45

( 2 ) INFORMATION FOR SEQ ID NO:45:

( i ) SEQUENCE CHARACTERISTICS:
        ( A ) LENGTH: 40 base pairs
        ( B ) TYPE: nucleic acid
        ( C ) STRANDEDNESS: both
        ( D ) TOPOLOGY: both ( x i ) SEQUENCE DESCRIPTION: SEQ ID NO:45:

CTCTTGACAA CCGCGTAACA GGAGTCATCA TATCGCCTAT 40

( 2 ) INFORMATION FOR SEQ ID NO:46:

( i ) SEQUENCE CHARACTERISTICS:
        ( A ) LENGTH: 40 base pairs
        ( B ) TYPE: nucleic acid
        ( C ) STRANDEDNESS: both
        ( D ) TOPOLOGY: both ( x i ) SEQUENCE DESCRIPTION: SEQ ID NO:46:

GAGTGGTGTA AGCCGTGCAC ATTGTCATCA TGGGCTGCGG 40

(2) INFORMATION FOR SEQ ID NO:47:

(i) SEQUENCE CHARACTERISTICS:
(A) LENGTH: 40 base pairs
(B) TYPE: nucleic acid
(C) STRANDEDNESS: both
(D) TOPOLOGY: both (xi) SEQUENCE DESCRIPTION: SEQ ID NO:47:

CACTGGAATG CCCCTACCAC GGTTGGTTGT TCGAAACGGG 40

(2) INFORMATION FOR SEQ ID NO:48:

(i) SEQUENCE CHARACTERISTICS:
(A) LENGTH: 40 base pairs
(B) TYPE: nucleic acid
(C) STRANDEDNESS: both
(D) TOPOLOGY: both (xi) SEQUENCE DESCRIPTION: SEQ ID NO:48:

CTATTGACGA ACGTTCACGG CCTCACACAA TGAGTCCTCG 40

(2) INFORMATION FOR SEQ ID NO:49:

(i) SEQUENCE CHARACTERISTICS:
(A) LENGTH: 413 amino acids
(B) TYPE: amino acid
(C) STRANDEDNESS: both
(D) TOPOLOGY: both (xi) SEQUENCE DESCRIPTION: SEQ ID NO:49:

```
Asn Gly Trp Gly Trp Glu Asp Gln Arg Ser Cys Ile Ala Arg Ser Thr
 1               5                  10                  15

Cys Ala Ala Gln Pro Ala Pro Phe Gly Ile Val Gly Ser Gly Ser Ser
             20                  25                  30

Thr Pro Val Ser Ser Ser Ser Ser Leu Ser Ser Ser Ser Val Val
         35                  40                  45

Ser Ser Ile Arg Ser Ser Ser Ser Ser Ser Ser Ser Val Ala Thr
     50                  55                  60

Gly Asn Gly Leu Ala Ser Leu Ala Asp Phe Pro Ile Gly Val Ala Val
65                   70                  75                  80

Ala Ala Ser Gly Gly Asn Ala Asp Ile Phe Thr Ser Ser Ala Arg Gln
                 85                  90                  95

Asn Ile Val Arg Ala Glu Phe Asn Gln Ile Thr Ala Glu Asn Ile Met
            100                 105                 110

Lys Met Ser Tyr Met Tyr Ser Gly Ser Asn Phe Ser Phe Thr Asn Ser
            115                 120                 125

Asp Arg Leu Val Ser Trp Ala Ala Gln Asn Gly Gln Thr Val His Gly
        130                 135                 140

His Ala Leu Val Trp His Pro Ser Tyr Gln Leu Pro Asn Trp Ala Ser
145                 150                 155                 160

Asp Ser Asn Ala Asn Phe Arg Gln Asp Phe Ala Arg His Ile Asp Thr
                        165                 170                 175

Val Ala Ala His Phe Ala Gly Gln Val Lys Ser Trp Asp Val Val Asn
                180                 185                 190

Glu Ala Leu Phe Asp Ser Ala Asp Asp Pro Asp Gly Arg Gly Ser Ala
            195                 200                 205

Asn Gly Tyr Arg Gln Ser Val Phe Tyr Arg Gln Phe Gly Gly Pro Glu
        210                 215                 220

Tyr Ile Asp Glu Ala Phe Arg Arg Ala Pro Arg Ala Asp Pro Thr Ala
```

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |
| Glu | Leu | Tyr | Tyr | Asn | Asp | Phe | Asn | Thr | Glu | Asn | Gly | Ala | Lys | Thr |
|     |     |     |     | 245 |     |     |     |     | 250 |     |     |     |     | 255 |
| Thr | Ala | Leu | Val | Asn | Leu | Val | Gln | Arg | Leu | Leu | Asn | Asn | Gly | Val | Pro |
|     |     |     | 260 |     |     |     | 265 |     |     |     |     | 270 |     |     |
| Ile | Asp | Gly | Val | Gly | Phe | Gln | Met | His | Val | Met | Asn | Asp | Tyr | Pro | Ser |
|     |     | 275 |     |     |     |     | 280 |     |     |     |     | 285 |     |     |
| Ile | Ala | Asn | Ile | Arg | Gln | Ala | Met | Gln | Lys | Ile | Val | Ala | Leu | Ser | Pro |
|     | 290 |     |     |     |     | 295 |     |     |     |     | 300 |     |     |     |
| Thr | Leu | Lys | Ile | Lys | Ile | Thr | Glu | Leu | Asp | Val | Arg | Leu | Asn | Asn | Pro |
| 305 |     |     |     |     | 310 |     |     |     |     | 315 |     |     |     |     | 320 |
| Tyr | Asp | Gly | Asn | Ser | Ser | Asn | Asp | Tyr | Thr | Asn | Arg | Asn | Asp | Cys | Ala |
|     |     |     |     | 325 |     |     |     |     | 330 |     |     |     |     | 335 |
| Val | Ser | Cys | Ala | Gly | Leu | Asp | Arg | Gln | Lys | Ala | Arg | Tyr | Lys | Glu | Ile |
|     |     |     | 340 |     |     |     |     | 345 |     |     |     |     | 350 |     |
| Val | Gln | Ala | Tyr | Leu | Glu | Val | Val | Pro | Pro | Gly | Arg | Arg | Gly | Gly | Ile |
|     |     |     | 355 |     |     |     |     | 360 |     |     |     |     | 365 |     |
| Thr | Val | Trp | Gly | Ile | Ala | Asp | Pro | Asp | Ser | Trp | Leu | Tyr | Thr | His | Gln |
|     |     | 370 |     |     |     |     | 375 |     |     |     |     | 380 |     |     |
| Asn | Leu | Pro | Asp | Trp | Pro | Leu | Leu | Phe | Asn | Asp | Asn | Leu | Gln | Pro | Lys |
| 385 |     |     |     |     | 390 |     |     |     |     | 395 |     |     |     |     | 400 |
| Pro | Ala | Tyr | Gln | Gly | Val | Val | Glu | Ala | Leu | Ser | Gly | Arg |
|     |     |     |     | 405 |     |     |     |     | 410 |     |     |     |

( 2 ) INFORMATION FOR SEQ ID NO:50:

( i ) SEQUENCE CHARACTERISTICS:
        ( A ) LENGTH: 345 amino acids
        ( B ) TYPE: amino acid
        ( C ) STRANDEDNESS: both
        ( D ) TOPOLOGY: both ( x i ) SEQUENCE DESCRIPTION: SEQ ID NO:50:

| Gly | Ala | Trp | Thr | Thr | Trp | Gln | Thr | Ala | Thr | Ile | Asp | Val | Asp | Leu | Val |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gln | Gly | Asn | Asn | Ile | Val | Gln | Leu | Ser | Ala | Thr | Thr | Ala | Glu | Gly | Leu |
|     |     |     | 20  |     |     |     |     | 25  |     |     |     |     | 30  |     |
| Pro | Asn | Ile | Asp | Ser | Leu | Ser | Val | Val | Gly | Gly | Thr | Val | Arg | Ala | Gly |
|     |     | 35  |     |     |     |     | 40  |     |     |     |     | 45  |     |     |
| Asn | Cys | Gly | Ser | Val | Ser | Ser | Ser | Ser | Val | Gln | Ser | Ser | Ser | Ser |
|     | 50  |     |     |     |     | 55  |     |     |     |     | 60  |     |     |     |
| Ser | Ser | Ser | Ser | Ser | Ala | Ala | Ser | Ala | Lys | Lys | Phe | Ile | Gly | Asn | Ile |
| 65  |     |     |     |     | 70  |     |     |     |     | 75  |     |     |     |     | 80  |
| Thr | Thr | Ser | Gly | Ala | Val | Arg | Ser | Asp | Phe | Thr | Arg | Tyr | Trp | Asn | Gln |
|     |     |     |     | 85  |     |     |     |     | 90  |     |     |     |     | 95  |     |
| Ile | Thr | Pro | Glu | Asn | Glu | Ser | Lys | Trp | Gly | Ser | Val | Glu | Gly | Thr | Arg |
|     |     |     | 100 |     |     |     |     | 105 |     |     |     |     | 110 |     |
| Asn | Val | Tyr | Asn | Trp | Ala | Pro | Leu | Asp | Arg | Ile | Tyr | Ala | Tyr | Ala | Arg |
|     |     |     | 115 |     |     |     |     | 120 |     |     |     |     | 125 |     |
| Gln | Asn | Asn | Ile | Pro | Val | Lys | Ala | His | Thr | Phe | Val | Trp | Gly | Ala | Gln |
|     |     | 130 |     |     |     |     | 135 |     |     |     |     | 140 |     |     |
| Ser | Pro | Ser | Trp | Leu | Asn | Asn | Leu | Ser | Gly | Pro | Glu | Val | Ala | Val | Glu |
| 145 |     |     |     |     | 150 |     |     |     |     | 155 |     |     |     |     | 160 |
| Ile | Glu | Gln | Trp | Ile | Arg | Asp | Tyr | Cys | Ala | Arg | Tyr | Pro | Asp | Thr | Ala |
|     |     |     |     | 165 |     |     |     |     | 170 |     |     |     |     | 175 |     |
| Met | Ile | Asp | Val | Val | Asn | Glu | Ala | Val | Pro | Gly | His | Gln | Pro | Ala | Gly |

|   | 180 |   |   |   |   |   | 185 |   |   |   |   | 190 |   |   |
|---|---|---|---|---|---|---|---|---|---|---|---|---|---|---|
| Tyr | Ala | Gln | Arg | Ala | Phe | Gly | Asn | Asn | Trp | Ile | Gln | Arg | Val | Phe | Gln |
|   |   | 195 |   |   |   |   | 200 |   |   |   |   | 205 |   |   |   |
| Leu | Ala | Arg | Gln | Tyr | Cys | Pro | Asn | Ser | Ile | Leu | Ile | Leu | Asn | Asp | Tyr |
|   |   | 210 |   |   |   | 215 |   |   |   |   | 220 |   |   |   |   |
| Asn | Asn | Ile | Arg | Trp | Gln | His | Asn | Glu | Phe | Ile | Ala | Leu | Ala | Lys | Ala |
| 225 |   |   |   |   | 230 |   |   |   |   | 235 |   |   |   |   | 240 |
| Gln | Gly | Asn | Tyr | Ile | Asp | Ala | Val | Gly | Leu | Gln | Ala | His | Glu | Leu | Lys |
|   |   |   |   | 245 |   |   |   |   | 250 |   |   |   |   | 255 |   |
| Gly | Met | Thr | Ala | Ala | Gln | Val | Lys | Thr | Ala | Ile | Asp | Asn | Ile | Trp | Asn |
|   |   |   | 260 |   |   |   |   | 265 |   |   |   |   | 270 |   |   |
| Gln | Val | Gly | Lys | Pro | Ile | Tyr | Ile | Ser | Glu | Tyr | Asp | Ile | Gly | Asp | Thr |
|   |   | 275 |   |   |   |   | 280 |   |   |   |   | 285 |   |   |   |
| Asn | Asp | Gln | Val | Gln | Leu | Gln | Asn | Phe | Gln | Ala | His | Phe | Pro | Val | Phe |
| 290 |   |   |   |   | 295 |   |   |   |   | 300 |   |   |   |   |   |
| Tyr | Asn | His | Pro | His | Val | His | Gly | Ile | Thr | Ser | Gly | Ile | Cys | Gly | Gly |
| 305 |   |   |   |   | 310 |   |   |   |   | 315 |   |   |   |   | 320 |
| Gln | Asp | Leu | Asp | Arg | Arg | Leu | Arg | Phe | Asp | Pro | Gly | Gln | Trp | His | Thr |
|   |   |   |   | 325 |   |   |   |   | 330 |   |   |   |   | 335 |   |
| Ala | Pro | Gly | Asn | Asp | Val | Val | Asp | Xaa |   |   |   |   |   |   |   |
|   |   |   | 340 |   |   |   |   | 345 |   |   |   |   |   |   |   |

( 2 ) INFORMATION FOR SEQ ID NO:51:

( i ) SEQUENCE CHARACTERISTICS:
    ( A ) LENGTH: 405 amino acids
    ( B ) TYPE: amino acid
    ( C ) STRANDEDNESS: both
    ( D ) TOPOLOGY: both ( x i ) SEQUENCE DESCRIPTION: SEQ ID NO:51:

| Met | Pro | Ile | Asn | Val | Met | Pro | Arg | Pro | Gly | Ala | Arg | Lys | Arg | Ala | Leu |
| 1 |   |   |   | 5 |   |   |   |   | 10 |   |   |   |   | 15 |   |
| Leu | Ala | Gly | Ala | Val | Gly | Leu | Leu | Thr | Ala | Ala | Ala | Leu | Val | Ala |
|   |   |   | 20 |   |   |   |   | 25 |   |   |   |   | 30 |   |
| Pro | Ser | Pro | Ala | Val | Ala | Ala | Glu | Ser | Thr | Leu | Gly | Ala | Ala | Ala | Ala |
|   |   | 35 |   |   |   |   | 40 |   |   |   |   | 45 |   |   |   |
| Gln | Ser | Gly | Arg | Tyr | Phe | Gly | Thr | Ala | Ile | Ala | Ser | Gly | Arg | Leu | Asn |
|   | 50 |   |   |   |   | 55 |   |   |   |   | 60 |   |   |   |   |
| Asp | Ser | Thr | Tyr | Thr | Thr | Ile | Ala | Asn | Arg | Glu | Phe | Asn | Met | Val | Thr |
| 65 |   |   |   |   | 70 |   |   |   |   | 75 |   |   |   |   | 80 |
| Ala | Glu | Asn | Glu | Met | Lys | Ile | Asp | Ala | Thr | Glu | Pro | Asn | Arg | Gly | Gln |
|   |   |   |   | 85 |   |   |   |   | 90 |   |   |   |   | 95 |   |
| Phe | Asn | Phe | Ser | Ser | Ala | Asp | Arg | Ile | Tyr | Asn | Trp | Ala | Val | Gln | Asn |
|   |   |   | 100 |   |   |   |   | 105 |   |   |   |   | 110 |   |   |
| Gly | Lys | Gln | Val | Arg | Gly | His | Thr | Leu | Ala | Trp | His | Ser | Gln | Gln | Pro |
|   |   | 115 |   |   |   |   | 120 |   |   |   |   | 125 |   |   |   |
| Gly | Trp | Met | Gln | Ser | Leu | Ser | Gly | Ser | Ser | Leu | Arg | Gln | Ala | Met | Ile |
|   | 130 |   |   |   |   | 135 |   |   |   |   | 140 |   |   |   |   |
| Asp | His | Ile | Asn | Gly | Val | Met | Ala | His | Tyr | Lys | Gly | Lys | Ile | Val | Gln |
| 145 |   |   |   |   | 150 |   |   |   |   | 155 |   |   |   |   | 160 |
| Trp | Asp | Val | Val | Asn | Glu | Ala | Phe | Ala | Asp | Gly | Asn | Ser | Gly | Gly | Arg |
|   |   |   |   | 165 |   |   |   |   | 170 |   |   |   |   | 175 |   |
| Arg | Asp | Ser | Asn | Leu | Gln | Arg | Thr | Gly | Asn | Asp | Trp | Ile | Glu | Val | Ala |
|   |   |   | 180 |   |   |   |   | 185 |   |   |   |   | 190 |   |   |
| Phe | Arg | Thr | Ala | Arg | Asn | Ala | Asp | Pro | Asn | Ala | Lys | Leu | Cys | Tyr | Asn |

|   |   |   |   |   | 195 |   |   |   |   | 200 |   |   |   |   | 205 |   |   |
|---|---|---|---|---|---|---|---|---|---|---|---|---|---|---|---|---|---|

Asp Tyr Asn Ile Glu Asn Trp Asn Trp Ala Lys Thr Gln Gly Val Tyr
210 215 220

Asn Met Val Arg Asp Phe Lys Gln Arg Gly Val Pro Ile Asp Cys Val
225 230 235 240

Gly Phe Gln Ser His Phe Asn Ser Gly Ser Pro Tyr Asn Ser Asn Phe
245 250 255

Arg Thr Thr Leu Gln Asn Phe Ala Ala Leu Gly Val Asp Val Ala Ile
260 265 270

Thr Glu Leu Asp Ile Gln Gly Ala Ser Pro Thr Thr Tyr Ala Asn Val
275 280 285

Val Asn Asp Cys Leu Ala Val Ser Arg Cys Leu Gly Ile Thr Val Trp
290 295 300

Gly Val Arg Asp Thr Asp Ser Trp Arg Ser Asp Gln Thr Pro Leu Leu
305 310 315 320

Phe Asp Gly Asn Gly Asn Lys Lys Ala Ala Tyr Ser Ala Val Leu Asn
325 330 335

Ala Leu Asn Gly Gly Gly Thr Ser Glu Pro Pro Pro Ala Ser Asp Ala
340 345 350

Gly Thr Ile Lys Gly Val Gly Ser Gly Arg Cys Leu Asp Val Pro Asn
355 360 365

Ala Ser Thr Ser Asp Gly Val Gln Leu Gln Leu Trp Asp Cys His Gly
370 375 380

Gly Thr Asn Gln Gln Trp Thr Tyr Thr Asp Ser Gln Glu Leu Arg Val
385 390 395 400

Tyr Gly Asn Lys Cys
405

(2) INFORMATION FOR SEQ ID NO:52:

(i) SEQUENCE CHARACTERISTICS:
  (A) LENGTH: 406 amino acids
  (B) TYPE: amino acid
  (D) TOPOLOGY: both (xi) SEQUENCE DESCRIPTION: SEQ ID NO:52:

Met Gly Ser Tyr Ala Leu Pro Arg Ser Gly Val Arg Arg Ser Ile Arg
1 5 10 15

Val Leu Leu Ala Ala Leu Val Val Gly Val Leu Gly Thr Ala Thr Ala
20 25 30

Leu Ile Ala Pro Pro Gly Ala His Ala Ala Glu Ser Thr Leu Gly Ala
35 40 45

Ala Ala Ala Gln Ser Gly Arg Tyr Phe Gly Thr Ala Ile Ala Ser Gly
50 55 60

Arg Leu Ser Asp Ser Thr Tyr Thr Ser Ile Ala Gly Arg Glu Phe Asn
65 70 75 80

Met Val Thr Ala Glu Asn Glu Met Lys Ile Asp Ala Thr Glu Pro Gln
85 90 95

Arg Gly Gln Phe Asn Phe Ser Ser Ala Asp Arg Val Tyr Asn Trp Ala
100 105 110

Val Gln Asn Gly Lys Gln Val Arg Gly His Thr Leu Ala Trp His Ser
115 120 125

Gln Gln Pro Gly Trp Met Gln Ser Leu Ser Gly Arg Pro Leu Arg Gln
130 135 140

Ala Met Ile Asp His Ile Asn Gly Val Met Ala His Tyr Lys Gly Lys
145 150 155 160

| | | | | | | | | | | | | | | |
|---|---|---|---|---|---|---|---|---|---|---|---|---|---|---|
| Ile | Val | Gln | Trp | Asp | Val | Val | Asn | Glu | Ala | Phe | Ala | Asp | Gly | Ser | Ser |
| | | | | 165 | | | | | 170 | | | | | 175 |
| Gly | Ala | Arg | Arg | Asp | Ser | Asn | Leu | Gln | Arg | Ser | Gly | Asn | Asp | Trp | Ile |
| | | | 180 | | | | | 185 | | | | | 190 | | |
| Glu | Val | Ala | Phe | Arg | Thr | Ala | Arg | Ala | Ala | Asp | Pro | Ser | Ala | Lys | Leu |
| | | 195 | | | | 200 | | | | | 205 | | | | |
| Cys | Tyr | Asn | Asp | Tyr | Asn | Val | Glu | Asn | Trp | Thr | Trp | Ala | Lys | Thr | Gln |
| | 210 | | | | | 215 | | | | | 220 | | | | |
| Ala | Met | Tyr | Asn | Met | Val | Arg | Asp | Phe | Lys | Gln | Arg | Gly | Val | Pro | Ile |
| 225 | | | | | 230 | | | | | 235 | | | | | 240 |
| Asp | Cys | Val | Gly | Phe | Gln | Ser | His | Phe | Asn | Ser | Gly | Ser | Pro | Tyr | Asn |
| | | | | 245 | | | | | 250 | | | | | 255 | |
| Ser | Asn | Phe | Arg | Thr | Thr | Leu | Gln | Asn | Phe | Ala | Ala | Leu | Gly | Val | Asp |
| | | | 260 | | | | | 265 | | | | | 270 | | |
| Val | Ala | Ile | Thr | Glu | Leu | Asp | Ile | Gln | Gly | Ala | Pro | Ala | Ser | Thr | Tyr |
| | | | 275 | | | | | 280 | | | | | 285 | | |
| Ala | Asn | Val | Thr | Asn | Asp | Cys | Leu | Ala | Val | Ser | Arg | Cys | Leu | Gly | Ile |
| | | 290 | | | | | 295 | | | | | 300 | | | |
| Thr | Val | Trp | Gly | Val | Arg | Asp | Ser | Asp | Ser | Trp | Arg | Ser | Glu | Gln | Thr |
| 305 | | | | | 310 | | | | | 315 | | | | | 320 |
| Pro | Leu | Leu | Phe | Asn | Asp | Gly | Ser | Lys | Lys | Ala | Ala | Tyr | Thr | Ala |
| | | | | 325 | | | | | 330 | | | | | 335 |
| Val | Leu | Asp | Ala | Leu | Asn | Gly | Gly | Asp | Ser | Ser | Glu | Pro | Pro | Ala | Asp |
| | | | 340 | | | | | 345 | | | | | 350 | | |
| Gly | Gly | Gln | Ile | Lys | Gly | Val | Gly | Ser | Gly | Arg | Cys | Leu | Asp | Val | Pro |
| | | 355 | | | | | 360 | | | | | 365 | | | |
| Asp | Ala | Ser | Thr | Ser | Asp | Gly | Thr | Gln | Leu | Gln | Leu | Trp | Asp | Cys | His |
| | 370 | | | | | 375 | | | | | 380 | | | | |
| Ser | Gly | Thr | Asn | Gln | Gln | Trp | Ala | Ala | Thr | Asp | Ala | Gly | Glu | Leu | Arg |
| 385 | | | | | 390 | | | | | 395 | | | | | 400 |
| Val | Tyr | Gly | Asp | Lys | Cys |
| | | | | 405 | |

(2) INFORMATION FOR SEQ ID NO:53:

(i) SEQUENCE CHARACTERISTICS:
        (A) LENGTH: 427 amino acids
        (B) TYPE: amino acid
        (C) STRANDEDNESS: both
        (D) TOPOLOGY: both (xi) SEQUENCE DESCRIPTION: SEQ ID NO:53:

| | | | | | | | | | | | | | | | |
|---|---|---|---|---|---|---|---|---|---|---|---|---|---|---|---|
| Met | Pro | Arg | Thr | Thr | Pro | Ala | Pro | Gly | His | Pro | Ala | Arg | Gly | Ala | Arg |
| 1 | | | | 5 | | | | | 10 | | | | | 15 | |
| Thr | Ala | Leu | Arg | Thr | Thr | Arg | Arg | Arg | Ala | Ala | Thr | Leu | Val | Val | Gly |
| | | | 20 | | | | | 25 | | | | | 30 | | |
| Ala | Thr | Val | Val | Leu | Pro | Ala | Gln | Ala | Ala | Thr | Thr | Leu | Lys | Glu | Ala |
| | | 35 | | | | | 40 | | | | | 45 | | | |
| Ala | Asp | Gly | Ala | Gly | Arg | Asp | Phe | Gly | Phe | Ala | Leu | Asp | Pro | Asn | Arg |
| | | 50 | | | | | 55 | | | | | 60 | | | |
| Leu | Ser | Glu | Ala | Gln | Tyr | Lys | Ala | Ile | Ala | Asp | Ser | Glu | Phe | Asn | Leu |
| 65 | | | | | 70 | | | | | 75 | | | | | 80 |
| Val | Val | Ala | Glu | Asn | Ala | Met | Lys | Trp | Asp | Ala | Thr | Glu | Pro | Ser | Gln |
| | | | | 85 | | | | | 90 | | | | | 95 | |
| Asn | Ser | Phe | Ser | Phe | Gly | Ala | Gly | Asp | Arg | Val | Ala | Ser | Tyr | Ala | Ala |
| | | | | 100 | | | | | 105 | | | | | 110 | |

```
Asp Thr Gly Lys Glu Leu Tyr Gly His Thr Leu Val Trp His Ser Gln
        115                 120                 125

Leu Pro Asp Trp Ala Lys Asn Leu Asn Gly Ser Ala Phe Glu Ser Ala
    130                 135                 140

Met Val Asn His Val Thr Lys Val Ala Asp His Phe Glu Gly Lys Val
145                 150                 155                 160

Ala Ser Trp Asp Val Val Asn Glu Ala Phe Ala Asp Gly Asp Gly Pro
                165                 170                 175

Pro Gln Asp Ser Ala Phe Gln Gln Lys Leu Gly Asn Gly Tyr Ile Glu
            180                 185                 190

Thr Ala Phe Arg Ala Ala Arg Ala Ala Asp Pro Thr Ala Lys Leu Cys
        195                 200                 205

Ile Asn Asp Tyr Asn Val Glu Gly Ile Asn Ala Lys Ser Asn Ser Leu
    210                 215                 220

Tyr Asp Leu Val Lys Asp Phe Lys Ala Arg Gly Val Pro Leu Asp Cys
225                 230                 235                 240

Val Gly Phe Gln Ser His Leu Ile Val Gly Gln Val Pro Gly Asp Phe
                245                 250                 255

Arg Gln Asn Leu Gln Arg Phe Ala Asp Leu Gly Val Asp Val Arg Ile
            260                 265                 270

Thr Glu Leu Asp Ile Arg Met Arg Thr Pro Ser Asp Thr Lys Leu
        275                 280                 285

Ala Thr Gln Ala Ala Asp Tyr Lys Lys Val Val Gln Ala Cys Met Gln
    290                 295                 300

Val Thr Arg Cys Gln Gly Val Thr Val Trp Gly Ile Thr Asp Lys Tyr
305                 310                 315                 320

Ser Trp Val Pro Asp Val Phe Pro Gly Glu Gly Ala Ala Leu Val Trp
                325                 330                 335

Asp Ala Ser Tyr Ala Lys Lys Pro Ala Tyr Ala Ala Val Met Glu Ala
            340                 345                 350

Phe Gly Ala Ser Pro Thr Pro Thr Pro Thr Thr Pro Thr Pro Thr Pro
        355                 360                 365

Thr Thr Pro Thr Pro Thr Pro Thr Ser Gly Pro Ala Gly Cys Gln Val
370                 375                 380

Leu Trp Gly Val Asn Gln Trp Asn Thr Gly Phe Thr Ala Asn Val Thr
385                 390                 395                 400

Val Lys Asn Thr Ser Ser Ala Pro Val Asp Gly Trp Thr Leu Thr Phe
                405                 410                 415

Ser Phe Pro Ser Gly Gln Gln Val Thr Gln Ala
            420                 425
```

( 2 ) INFORMATION FOR SEQ ID NO:54:

( i ) SEQUENCE CHARACTERISTICS:
        ( A ) LENGTH: 399 amino acids
        ( B ) TYPE: amino acid
        ( D ) TOPOLOGY: both ( x i ) SEQUENCE DESCRIPTION: SEQ ID NO:54:

```
Ser Asp Leu Gln Ala Leu Lys Arg His Leu Leu Gly Ile Ser Pro Leu
1               5                   10                  15

Thr Gly Glu Ala Leu Leu Arg Ala Asp Val Asn Arg Ser Gly Lys Val
            20                  25                  30

Asp Ser Thr Asp Tyr Ser Val Leu Lys Arg Tyr Ile Leu Arg Ile Ile
        35                  40                  45
```

|   |   |   |   |   |   |   |   |   |   |   |   |   |   |   |
|---|---|---|---|---|---|---|---|---|---|---|---|---|---|---|
| Thr | Glu | Phe | Pro | Gly | Gln | Gly | Asp | Val | Gln | Thr | Pro | Asn | Pro | Ser | Val |
|   | 50 |   |   |   | 55 |   |   |   |   | 60 |   |   |   |   |
| Thr | Pro | Thr | Gln | Thr | Pro | Ile | Pro | Thr | Ile | Ser | Gly | Asn | Ala | Leu | Arg |
| 65 |   |   |   |   | 70 |   |   |   | 75 |   |   |   |   | 80 |
| Asp | Tyr | Ala | Glu | Ala | Arg | Gly | Ile | Lys | Ile | Gly | Thr | Cys | Val | Asn | Tyr |
|   |   |   |   | 85 |   |   |   |   | 90 |   |   |   |   | 95 |
| Pro | Phe | Tyr | Asn | Asn | Ser | Asp | Pro | Thr | Tyr | Asn | Ser | Ile | Leu | Gln | Arg |
|   |   |   | 100 |   |   |   |   | 105 |   |   |   |   | 110 |   |
| Glu | Phe | Ser | Met | Val | Val | Cys | Glu | Asn | Glu | Met | Lys | Phe | Asp | Ala | Leu |
|   |   | 115 |   |   |   |   | 120 |   |   |   |   | 125 |   |   |
| Gln | Pro | Arg | Gln | Asn | Val | Phe | Asp | Phe | Ser | Lys | Gly | Asp | Gln | Leu | Leu |
|   | 130 |   |   |   |   | 135 |   |   |   |   | 140 |   |   |   |
| Ala | Phe | Ala | Glu | Arg | Asn | Gly | Met | Gln | Met | Arg | Gly | His | Thr | Leu | Ile |
| 145 |   |   |   |   | 150 |   |   |   |   | 155 |   |   |   |   | 160 |
| Trp | His | Asn | Gln | Asn | Pro | Ser | Trp | Leu | Thr | Asn | Gly | Asn | Trp | Asn | Arg |
|   |   |   |   | 165 |   |   |   |   | 170 |   |   |   |   | 175 |
| Asp | Ser | Leu | Leu | Ala | Val | Met | Lys | Asn | His | Ile | Thr | Thr | Val | Met | Thr |
|   |   |   | 180 |   |   |   |   | 185 |   |   |   |   | 190 |   |
| His | Tyr | Lys | Gly | Lys | Ile | Val | Glu | Trp | Asp | Val | Ala | Asn | Glu | Cys | Met |
|   |   | 195 |   |   |   |   | 200 |   |   |   |   | 205 |   |   |
| Asp | Asp | Ser | Gly | Asn | Gly | Leu | Arg | Ser | Ser | Ile | Trp | Arg | Asn | Val | Ile |
|   | 210 |   |   |   |   | 215 |   |   |   |   | 220 |   |   |   |
| Gly | Gln | Asp | Tyr | Leu | Asp | Tyr | Ala | Phe | Arg | Tyr | Ala | Arg | Glu | Ala | Asp |
| 225 |   |   |   |   | 230 |   |   |   |   | 235 |   |   |   |   | 240 |
| Pro | Asp | Ala | Leu | Leu | Phe | Tyr | Asn | Asp | Tyr | Asn | Ile | Glu | Asp | Leu | Gly |
|   |   |   |   | 245 |   |   |   |   | 250 |   |   |   |   | 255 |
| Pro | Lys | Ser | Asn | Ala | Val | Phe | Asn | Met | Ile | Lys | Ser | Met | Lys | Glu | Arg |
|   |   |   | 260 |   |   |   |   | 265 |   |   |   |   | 270 |   |
| Gly | Val | Pro | Ile | Asp | Gly | Val | Gly | Phe | Gln | Cys | His | Phe | Ile | Asn | Gly |
|   |   | 275 |   |   |   |   | 280 |   |   |   |   | 285 |   |   |
| Met | Ser | Pro | Glu | Tyr | Leu | Ala | Ser | Ile | Asp | Gln | Asn | Ile | Lys | Arg | Tyr |
| 290 |   |   |   |   | 295 |   |   |   |   | 300 |   |   |   |   |
| Ala | Glu | Ile | Gly | Val | Ile | Val | Ser | Phe | Thr | Glu | Ile | Asp | Ile | Arg | Ile |
| 305 |   |   |   |   | 310 |   |   |   |   | 315 |   |   |   |   | 320 |
| Pro | Gln | Ser | Glu | Asn | Pro | Ala | Thr | Ala | Phe | Gln | Val | Gln | Ala | Asn | Asn |
|   |   |   |   | 325 |   |   |   |   | 330 |   |   |   |   | 335 |
| Tyr | Lys | Glu | Leu | Met | Lys | Ile | Cys | Leu | Ala | Asn | Pro | Asn | Cys | Asn | Thr |
|   |   |   | 340 |   |   |   |   | 345 |   |   |   |   | 350 |   |
| Phe | Val | Met | Trp | Gly | Phe | Thr | Asp | Lys | Tyr | Thr | Trp | Ile | Pro | Gly | Thr |
|   |   | 355 |   |   |   |   | 360 |   |   |   |   | 365 |   |   |
| Phe | Pro | Gly | Tyr | Gly | Asn | Pro | Leu | Ile | Tyr | Asp | Ser | Asn | Tyr | Asn | Pro |
|   | 370 |   |   |   |   | 375 |   |   |   |   | 380 |   |   |   |
| Lys | Pro | Ala | Tyr | Asn | Ala | Ile | Lys | Glu | Ala | Leu | Met | Gly | Tyr | Xaa |   |
| 385 |   |   |   |   | 390 |   |   |   |   | 395 |   |   |   |   |

( 2 ) INFORMATION FOR SEQ ID NO:55:

( i ) SEQUENCE CHARACTERISTICS:
        ( A ) LENGTH: 397 amino acids
        ( B ) TYPE: amino acid
        ( D ) TOPOLOGY: both ( x i ) SEQUENCE DESCRIPTION: SEQ ID NO:55:

|   |   |   |   |   |   |   |   |   |   |   |   |   |   |   |   |
|---|---|---|---|---|---|---|---|---|---|---|---|---|---|---|---|
| Met | Ile | Thr | Leu | Phe | Arg | Lys | Pro | Phe | Val | Ala | Gly | Leu | Ala | Ile | Ser |
| 1 |   |   |   | 5 |   |   |   |   | 10 |   |   |   |   | 15 |   |
| Leu | Leu | Val | Gly | Gly | Gly | Ile | Gly | Asn | Val | Ala | Ala | Ala | Gln | Gly | Gly |

|   |   |   |   |   | 20 |   |   |   |   | 25 |   |   |   |   | 30 |
|---|---|---|---|---|---|---|---|---|---|---|---|---|---|---|---|
| Pro | Pro | Lys<br>35 | Ser | Gly | Val | Phe | Gly<br>40 | Glu | Asn | Glu | Lys | Arg<br>45 | Asn | Asp | Gln |
| Pro | Phe<br>50 | Ala | Trp | Gln | Val | Ala<br>55 | Ser | Leu | Ser | Glu | Arg<br>60 | Tyr | Gln | Glu | Gln |
| Phe<br>65 | Asp | Ile | Gly | Ala | Ala<br>70 | Val | Glu | Pro | Tyr | Gln<br>75 | Leu | Glu | Gly | Arg | Gln<br>80 |
| Ala | Gln | Ile | Leu | Lys<br>85 | His | His | Tyr | Asn | Ser<br>90 | Leu | Val | Ala | Glu | Asn<br>95 | Ala |
| Met | Lys | Pro | Glu<br>100 | Ser | Leu | Gln | Pro | Arg<br>105 | Glu | Gly | Glu | Trp | Asn<br>110 | Trp | Glu |
| Gly | Ala | Asp<br>115 | Lys | Ile | Val | Glu | Phe<br>120 | Ala | Arg | Lys | His | Asn<br>125 | Met | Glu | Leu |
| Arg | Phe<br>130 | His | Thr | Leu | Val | Trp<br>135 | His | Ser | Gln | Val | Pro<br>140 | Glu | Trp | Phe | Phe |
| Ile<br>145 | Asp | Glu | Asp | Gly | Asn<br>150 | Arg | Met | Val | Asp | Glu<br>155 | Thr | Asp | Pro | Asp | Lys<br>160 |
| Arg | Glu | Ala | Asn | Lys<br>165 | Gln | Leu | Leu | Leu | Glu<br>170 | Arg | Met | Glu | Asn | His<br>175 | Ile |
| Lys | Thr | Val | Val<br>180 | Glu | Arg | Tyr | Lys | Asp<br>185 | Asp | Val | Thr | Ser | Trp<br>190 | Asp | Val |
| Val | Asn | Glu<br>195 | Val | Ile | Asp | Asp | Gly<br>200 | Gly | Leu | Arg | Glu<br>205 | Ser | Glu | Trp |
| Tyr | Gln | Ile<br>210 | Thr | Gly | Thr | Asp<br>215 | Tyr | Ile | Lys | Val | Ala<br>220 | Phe | Glu | Thr | Ala |
| Arg<br>225 | Lys | Tyr | Gly | Gly | Glu<br>230 | Glu | Ala | Lys | Leu | Tyr<br>235 | Ile | Asn | Asp | Tyr | Asn<br>240 |
| Thr | Glu | Val | Pro | Ser<br>245 | Lys | Arg | Asp | Asp | Leu<br>250 | Tyr | Asn | Leu | Val | Lys<br>255 | Asp |
| Leu | Leu | Glu | Gln<br>260 | Gly | Val | Pro | Ile | Asp<br>265 | Gly | Val | Gly | His<br>270 | Gln | Ser | His |
| Ile | Gln | Ile<br>275 | Gly | Trp | Pro | Ser | Ile<br>280 | Glu | Asp | Thr | Arg | Ala<br>285 | Ser | Phe | Glu |
| Lys | Phe<br>290 | Thr | Ser | Leu | Gly | Leu<br>295 | Asp | Asn | Gln | Val | Thr<br>300 | Glu | Leu | Asp | Met |
| Ser<br>305 | Leu | Tyr | Gly | Trp | Pro<br>310 | Pro | Thr | Gly | Ala | Tyr<br>315 | Thr | Ser | Tyr | Asp | Asp<br>320 |
| Ile | Pro | Ala | Glu | Leu<br>325 | Leu | Gln | Ala | Gln | Ala<br>330 | Asp | Arg | Tyr | Asp | Gln<br>335 | Leu |
| Phe | Glu | Leu | Tyr<br>340 | Glu | Glu | Leu | Ala | Ala<br>345 | Asp | Ile | Ser | Ser | Val<br>350 | Thr | Phe |
| Trp | Gly | Ile<br>355 | Ala | Asp | Asn | His | Thr<br>360 | Trp | Leu | Asp | Gly | Arg<br>365 | Ala | Arg | Glu |
| Tyr | Asn<br>370 | Asn | Gly | Val | Gly | Ile<br>375 | Asp | Ala | Pro | Phe | Val<br>380 | Phe | Asp | His | Asn |
| Tyr<br>385 | Arg | Val | Lys | Pro | Ala<br>390 | Tyr | Trp | Arg | Ile | Ile<br>395 | Asp | Xaa |   |   |   |

( 2 ) INFORMATION FOR SEQ ID NO:56:

( i ) SEQUENCE CHARACTERISTICS:
        ( A ) LENGTH: 388 amino acids
        ( B ) TYPE: amino acid
        ( C ) STRANDEDNESS: both
        ( D ) TOPOLOGY: both ( x i ) SEQUENCE DESCRIPTION: SEQ ID NO:56:

| Met | Asn | Lys | Phe | Leu | Asn | Lys | Lys | Trp | Ser | Leu | Ile | Leu | Thr | Met | Gly |
|---|---|---|---|---|---|---|---|---|---|---|---|---|---|---|---|
| 1 | | | | 5 | | | | | 10 | | | | | 15 | |
| Gly | Ile | Phe | Leu | Met | Ala | Thr | Leu | Ser | Leu | Ile | Phe | Ala | Thr | Gly | Lys |
| | | | 20 | | | | | 25 | | | | | 30 | | |
| Lys | Ala | Phe | Asn | Asp | Gln | Thr | Ser | Ala | Glu | Asp | Ile | Pro | Ser | Leu | Ala |
| | | 35 | | | | | 40 | | | | | 45 | | | |
| Glu | Ala | Phe | Arg | Asp | Tyr | Phe | Pro | Ile | Gly | Ala | Ala | Ile | Glu | Pro | Gly |
| | 50 | | | | | 55 | | | | | 60 | | | | |
| Tyr | Thr | Thr | Gly | Gln | Ile | Ala | Glu | Leu | Tyr | Lys | Lys | His | Val | Asn | Met |
| 65 | | | | | 70 | | | | | 75 | | | | | 80 |
| Leu | Val | Ala | Glu | Asn | Ala | Met | Lys | Pro | Ala | Ser | Leu | Gln | Pro | Thr | Glu |
| | | | | 85 | | | | | 90 | | | | | 95 | |
| Gly | Asn | Phe | Gln | Trp | Ala | Asp | Ala | Asp | Arg | Ile | Val | Gln | Phe | Ala | Lys |
| | | | 100 | | | | | 105 | | | | | 110 | | |
| Glu | Asn | Gly | Met | Glu | Leu | Arg | Phe | His | Thr | Leu | Val | Trp | His | Asn | Gln |
| | | 115 | | | | | 120 | | | | | 125 | | | |
| Thr | Pro | Thr | Gly | Phe | Ser | Leu | Asp | Lys | Glu | Gly | Lys | Pro | Met | Val | Glu |
| | 130 | | | | | 135 | | | | | 140 | | | | |
| Glu | Thr | Asp | Pro | Gln | Lys | Arg | Glu | Glu | Asn | Arg | Lys | Leu | Leu | Leu | Gln |
| 145 | | | | | 150 | | | | | 155 | | | | | 160 |
| Arg | Leu | Glu | Asn | Tyr | Ile | Arg | Ala | Val | Val | Leu | Arg | Tyr | Lys | Asp | Asp |
| | | | | 165 | | | | | 170 | | | | | 175 | |
| Ile | Lys | Ser | Trp | Asp | Val | Val | Asn | Glu | Val | Ile | Glu | Pro | Asn | Asp | Pro |
| | | | 180 | | | | | 185 | | | | | 190 | | |
| Gly | Gly | Met | Arg | Asn | Ser | Pro | Trp | Tyr | Gln | Ile | Thr | Gly | Thr | Glu | Tyr |
| | | 195 | | | | | 200 | | | | | 205 | | | |
| Ile | Glu | Val | Ala | Phe | Arg | Ala | Thr | Arg | Glu | Ala | Gly | Gly | Ser | Asp | Ile |
| | 210 | | | | | 215 | | | | | 220 | | | | |
| Lys | Leu | Tyr | Ile | Asn | Asp | Tyr | Asn | Thr | Asp | Asp | Pro | Val | Lys | Arg | Asp |
| 225 | | | | | 230 | | | | | 235 | | | | | 240 |
| Ile | Leu | Tyr | Glu | Leu | Val | Lys | Asn | Leu | Leu | Glu | Lys | Gly | Val | Pro | Ile |
| | | | | 245 | | | | | 250 | | | | | 255 | |
| Asp | Gly | Val | Gly | His | Gln | Thr | His | Ile | Asp | Ile | Tyr | Asn | Pro | Pro | Val |
| | | | 260 | | | | | 265 | | | | | 270 | | |
| Glu | Arg | Ile | Ile | Glu | Ser | Ile | Lys | Lys | Phe | Ala | Gly | Leu | Gly | Leu | Asp |
| | | 275 | | | | | 280 | | | | | 285 | | | |
| Asn | Ile | Ile | Thr | Glu | Leu | Asp | Met | Ser | Ile | Tyr | Ser | Trp | Asn | Asp | Arg |
| | 290 | | | | | 295 | | | | | 300 | | | | |
| Ser | Asp | Tyr | Gly | Asp | Ser | Ile | Pro | Asp | Tyr | Ile | Leu | Thr | Leu | Gln | Ala |
| 305 | | | | | 310 | | | | | 315 | | | | | 320 |
| Lys | Arg | Tyr | Gln | Glu | Leu | Phe | Asp | Ala | Leu | Lys | Glu | Asn | Lys | Asp | Ile |
| | | | | 325 | | | | | 330 | | | | | 335 | |
| Val | Ser | Ala | Val | Val | Phe | Trp | Gly | Ile | Ser | Asp | Lys | Tyr | Ser | Trp | Leu |
| | | | 340 | | | | | 345 | | | | | 350 | | |
| Asn | Gly | Phe | Pro | Val | Lys | Arg | Thr | Asn | Ala | Pro | Leu | Leu | Phe | Asp | Arg |
| | | 355 | | | | | 360 | | | | | 365 | | | |
| Asn | Phe | Met | Pro | Lys | Pro | Ala | Phe | Trp | Ala | Ile | Val | Asp | Pro | Ser | Arg |
| | 370 | | | | | 375 | | | | | 380 | | | | |
| Leu | Arg | Glu | Xaa | | | | | | | | | | | | |
| 385 | | | | | | | | | | | | | | | |

( 2 ) INFORMATION FOR SEQ ID NO:57:

( i ) SEQUENCE CHARACTERISTICS:
   ( A ) LENGTH: 343 amino acids
   ( B ) TYPE: amino acid
   ( C ) STRANDEDNESS: both
   ( D ) TOPOLOGY: both ( x i ) SEQUENCE DESCRIPTION: SEQ ID NO:57:

Met Arg Cys Leu Ile Val Cys Glu Asn Leu Glu Met Leu Asn Leu Ser
1               5                   10                  15

Leu Ala Lys Thr Tyr Lys Asp Tyr Phe Lys Ile Gly Ala Ala Val Thr
            20                  25                  30

Ala Lys Asp Leu Glu Gly Val His Arg Asp Ile Leu Leu Lys His Phe
        35                  40                  45

Asn Ser Leu Thr Pro Glu Asn Ala Met Lys Phe Glu Asn Ile His Pro
    50                  55                  60

Glu Glu Gln Arg Tyr Asn Phe Glu Glu Val Ala Arg Ile Lys Glu Phe
65                  70                  75                  80

Ala Ile Lys Asn Asp Met Lys Leu Arg Gly His Thr Phe Val Trp His
                85                  90                  95

Asn Gln Thr Pro Gly Trp Val Phe Leu Asp Lys Asn Gly Glu Glu Ala
            100                 105                 110

Ser Lys Glu Leu Val Ile Glu Arg Leu Arg Glu His Ile Lys Thr Leu
        115                 120                 125

Cys Glu Arg Tyr Lys Asp Val Val Tyr Ala Trp Asp Val Val Asn Glu
    130                 135                 140

Ala Val Glu Asp Lys Thr Glu Lys Leu Leu Arg Glu Ser Asn Trp Arg
145                 150                 155                 160

Lys Ile Ile Gly Asp Asp Tyr Ile Lys Ile Ala Phe Glu Ile Ala Arg
                165                 170                 175

Glu Tyr Ala Gly Asp Ala Lys Leu Phe Tyr Asn Asp Tyr Asn Asn Glu
            180                 185                 190

Met Pro Tyr Lys Leu Glu Lys Thr Tyr Lys Val Leu Lys Glu Leu Leu
        195                 200                 205

Glu Arg Gly Thr Pro Ile Asp Gly Ile Gly Ile Gln Ala His Trp Asn
    210                 215                 220

Ile Trp Asp Lys Asn Leu Val Ser Asn Leu Lys Lys Ala Ile Glu Val
225                 230                 235                 240

Tyr Ala Ser Leu Gly Leu Glu Ile His Ile Thr Glu Leu Asp Ile Ser
                245                 250                 255

Val Phe Glu Phe Glu Asp Lys Arg Thr Asp Leu Phe Glu Pro Thr Pro
            260                 265                 270

Glu Met Leu Glu Leu Gln Ala Lys Val Tyr Glu Asp Val Phe Ala Val
        275                 280                 285

Phe Arg Glu Tyr Lys Asp Val Ile Thr Ser Val Thr Leu Trp Gly Ile
    290                 295                 300

Ser Asp Arg His Thr Trp Lys Asp Asn Phe Pro Val Lys Gly Arg Lys
305                 310                 315                 320

Asp Trp Pro Leu Leu Phe Asp Val Asn Gly Lys Pro Lys Glu Ala Leu
                325                 330                 335

Tyr Arg Ile Leu Arg Phe Xaa
            340

( 2 ) INFORMATION FOR SEQ ID NO:58:

( i ) SEQUENCE CHARACTERISTICS:
      ( A ) LENGTH: 474 amino acids
      ( B ) TYPE: amino acid (C) STRANDEDNESS: both
(D) TOPOLOGY: both (xi) SEQUENCE DESCRIPTION: SEQ ID NO:58:

```
Lys Ala Thr Val Lys Ala Thr Ser Asp Lys Asp Asn Tyr Ile Gln Val
 1               5                  10                  15
Asn Asp Phe Ala Asn Val Asn Lys Gly Glu Trp Thr Glu Ile Lys Gly
                 20                  25                  30
Ser Phe Thr Leu Pro Val Ala Asp Tyr Ser Gly Ile Ser Ile Tyr Val
             35                  40                  45
Glu Ser Gln Asn Pro Thr Leu Glu Phe Tyr Ile Asp Asp Phe Ser Val
         50                  55                  60
Ile Gly Glu Ile Ser Asn Asn Gln Ile Thr Ile Gln Asn Asp Ile Pro
 65                  70                  75                  80
Asp Leu Tyr Ser Val Phe Lys Asp Tyr Phe Pro Ile Gly Val Ala Val
                 85                  90                  95
Asp Pro Ser Arg Leu Asn Asp Ala Asp Pro His Ala Gln Leu Thr Ala
             100                 105                 110
Lys His Phe Asn Met Leu Val Ala Glu Asn Ala Met Lys Pro Glu Ser
         115                 120                 125
Leu Gln Pro Thr Glu Gly Asn Phe Thr Phe Asp Asn Ala Asp Lys Ile
         130                 135                 140
Val Asp Tyr Ala Ile Ala His Asn Met Lys Met Arg Gly His Thr Leu
145                 150                 155                 160
Leu Trp His Asn Gln Val Pro Asp Trp Phe Phe Gln Asp Pro Ser Asp
                 165                 170                 175
Pro Ser Lys Ser Ala Ser Arg Asp Leu Leu Leu Gln Arg Leu Lys Thr
             180                 185                 190
His Ile Thr Thr Val Leu Asp His Phe Lys Thr Lys Tyr Gly Ser Gln
         195                 200                 205
Asn Pro Ile Ile Gly Trp Asp Val Val Asn Glu Val Leu Asp Asp Asn
     210                 215                 220
Gly Asn Leu Arg Asn Ser Lys Trp Leu Gln Ile Ile Gly Pro Asp Tyr
225                 230                 235                 240
Ile Glu Lys Ala Phe Glu Tyr Ala His Glu Ala Asp Pro Ser Met Lys
                 245                 250                 255
Leu Phe Ile Asn Asp Tyr Asn Ile Glu Asn Asn Gly Val Lys Thr Gln
             260                 265                 270
Ala Met Tyr Asp Leu Val Lys Lys Leu Lys Ser Glu Gly Val Pro Ile
         275                 280                 285
Asp Gly Ile Gly Met Gln Met His Ile Asn Ile Asn Ser Asn Ile Asp
     290                 295                 300
Asn Ile Lys Ala Ser Ile Glu Lys Leu Ala Ser Leu Gly Val Glu Ile
305                 310                 315                 320
Gln Val Thr Glu Leu Asp Met Asn Met Asn Gly Asn Ile Ser Asn Glu
                 325                 330                 335
Ala Leu Leu Lys Gln Ala Arg Leu Tyr Lys Gln Leu Phe Asp Leu Phe
             340                 345                 350
Lys Ala Glu Lys Gln Tyr Ile Thr Ala Val Val Phe Trp Gly Val Ser
         355                 360                 365
Asp Asp Val Thr Trp Leu Ser Lys Pro Asn Ala Pro Leu Leu Phe Asp
     370                 375                 380
Ser Lys Leu Gln Ala Lys Pro Ala Phe Trp Ala Val Val Asp Pro Ser
385                 390                 395                 400
```

| Lys | Ala | Ile | Pro | Asp 405 | Ile | Gln | Ser | Ala | Lys 410 | Ala | Leu | Glu | Gly | Ser 415 | Pro |
|---|---|---|---|---|---|---|---|---|---|---|---|---|---|---|---|
| Thr | Ile | Gly | Ala 420 | Asn | Val | Asp | Ser | Ser 425 | Trp | Lys | Leu | Val | Lys 430 | Pro | Leu |
| Tyr | Val | Asn 435 | Thr | Tyr | Val | Glu | Gly 440 | Thr | Val | Gly | Ala | Thr 445 | Ala | Thr | Val |
| Lys | Ser 450 | Met | Trp | Asp | Thr | Lys 455 | Asn | Leu | Tyr | Leu | Leu 460 | Val | Gln | Val | Ser |
| Asp 465 | Asn | Thr | Pro | Ser | Asn 470 | Asn | Asp | Gly | Ile | | | | | | |

(2) INFORMATION FOR SEQ ID NO:59:

(i) SEQUENCE CHARACTERISTICS:
    (A) LENGTH: 438 amino acids
    (B) TYPE: amino acid
    (D) TOPOLOGY: both (xi) SEQUENCE DESCRIPTION: SEQ ID NO:59:

| Met 1 | Lys | Arg | Asn | Leu 5 | Phe | Arg | Ile | Val | Ser 10 | Arg | Val | Val | Leu | Ile 15 | Ala |
|---|---|---|---|---|---|---|---|---|---|---|---|---|---|---|---|
| Phe | Ile | Ala | Ser 20 | Ile | Ser | Leu | Val | Gly 25 | Ala | Met | Ser | Tyr | Phe 30 | Pro | Val |
| Glu | Thr | Gln 35 | Ala | Ala | Pro | Asp | Trp 40 | Ser | Ile | Pro | Ser | Leu 45 | Cys | Glu | Ser |
| Tyr | Lys 50 | Asp | Asp | Phe | Met | Ile 55 | Gly | Val | Ala | Ile | Pro 60 | Ala | Arg | Cys | Leu |
| Ser 65 | Asn | Asp | Thr | Asp | Lys 70 | Arg | Met | Val | Leu | Lys 75 | His | Phe | Asn | Ser | Ile 80 |
| Thr | Ala | Glu | Asn | Glu 85 | Met | Lys | Pro | Glu | Ser 90 | Leu | Leu | Ala | Gly | Gln 95 | Thr |
| Ser | Thr | Gly | Leu 100 | Ser | Tyr | Arg | Phe | Ser 105 | Thr | Ala | Asp | Ala | Phe 110 | Val | Asp |
| Phe | Ala | Ser 115 | Thr | Asn | Lys | Ile | Gly 120 | Ile | Arg | Gly | His | Thr 125 | Leu | Val | Trp |
| His | Asn 130 | Gln | Thr | Pro | Asp | Trp 135 | Phe | Phe | Lys | Asp | Ser 140 | Asn | Gly | Gln | Arg |
| Leu 145 | Ser | Lys | Asp | Ala | Leu 150 | Leu | Ala | Arg | Leu | Lys 155 | Gln | Tyr | Ile | Tyr | Asp 160 |
| Val | Val | Gly | Arg | Tyr 165 | Lys | Gly | Lys | Val | Tyr 170 | Ala | Trp | Asp | Val | Val 175 | Asn |
| Glu | Ala | Ile | Asp 180 | Glu | Asn | Gln | Pro | Asp 185 | Ser | Tyr | Arg | Arg | Ser 190 | Thr | Trp |
| Tyr | Glu | Ile 195 | Cys | Gly | Pro | Glu | Tyr 200 | Ile | Glu | Lys | Ala | Phe 205 | Ile | Trp | Ala |
| His | Glu 210 | Ala | Asp | Pro | Asn | Ala 215 | Lys | Leu | Phe | Tyr | Asn 220 | Asp | Tyr | Asn | Thr |
| Glu 225 | Ile | Ser | Lys | Lys | Arg 230 | Asp | Phe | Ile | Tyr | Asn 235 | Met | Val | Lys | Asn | Leu 240 |
| Lys | Ser | Lys | Gly | Ile 245 | Pro | Ile | His | Gly | Ile 250 | Gly | Met | Gln | Cys | His 255 | Ile |
| Asn | Val | Asn | Trp 260 | Pro | Ser | Val | Ser | Glu 265 | Ile | Glu | Asn | Ser | Ile 270 | Lys | Leu |
| Phe | Ser | Ser 275 | Ile | Pro | Gly | Ile | Glu 280 | Ile | His | Ile | Thr | Glu 285 | Leu | Asp | Met |
| Ser | Leu | Tyr | Asn | Tyr | Gly | Ser | Ser | Glu | Asn | Tyr | Ser | Thr | Pro | Pro | Gln |

|   |   |   | 290 |   |   |   | 295 |   |   |   | 300 |   |   |   |
|---|---|---|---|---|---|---|---|---|---|---|---|---|---|---|
| Asp | Leu | Leu | Gln | Lys | Gln | Ser | Gln | Lys | Tyr | Lys | Glu | Ile | Phe | Thr | Met |
| 305 |   |   |   |   | 310 |   |   |   |   | 315 |   |   |   |   | 320 |
| Leu | Lys | Lys | Tyr | Lys | Asn | Val | Val | Lys | Ser | Val | Thr | Phe | Trp | Gly | Leu |
|   |   |   |   | 325 |   |   |   |   | 330 |   |   |   |   | 335 |   |
| Lys | Asp | Asp | Tyr | Ser | Trp | Leu | Arg | Ser | Phe | Tyr | Gly | Lys | Asn | Asp | Trp |
|   |   |   |   | 340 |   |   |   |   | 345 |   |   |   |   | 350 |   |
| Pro | Leu | Leu | Phe | Phe | Glu | Asp | Tyr | Ser | Ala | Lys | Pro | Ala | Tyr | Trp | Ala |
|   |   |   | 355 |   |   |   |   | 360 |   |   |   |   | 365 |   |   |
| Val | Ile | Glu | Ala | Ser | Gly | Val | Thr | Thr | Ser | Ser | Pro | Thr | Pro | Thr | Pro |
|   |   |   | 370 |   |   |   |   | 375 |   |   |   |   | 380 |   |   |
| Thr | Pro | Thr | Val | Thr | Val | Thr | Pro | Thr | Pro | Thr | Pro | Thr | Pro | Thr | Pro |
| 385 |   |   |   |   | 390 |   |   |   |   | 395 |   |   |   |   | 400 |
| Thr | Val | Thr | Ala | Thr | Pro | Thr | Pro | Thr | Pro | Thr | Pro | Val | Ser | Thr | Pro |
|   |   |   |   | 405 |   |   |   |   | 410 |   |   |   |   | 415 |   |
| Ala | Thr | Gly | Gly | Gln | Ile | Lys | Val | Leu | Tyr | Ala | Asn | Lys | Glu | Thr | Asn |
|   |   |   | 420 |   |   |   |   | 425 |   |   |   |   | 430 |   |   |
| Ser | Thr | Thr | Asn | Thr | Ile |
|   |   |   | 435 |   |   |

( 2 ) INFORMATION FOR SEQ ID NO:60:

( i ) SEQUENCE CHARACTERISTICS:
     ( A ) LENGTH: 392 amino acids
     ( B ) TYPE: amino acid
     ( D ) TOPOLOGY: both ( x i ) SEQUENCE DESCRIPTION: SEQ ID NO:60:

| Met | Asn | Leu | Lys | Thr | Ala | Tyr | Glu | Pro | Tyr | Phe | Lys | Ile | Gly | Ala | Ala |
|---|---|---|---|---|---|---|---|---|---|---|---|---|---|---|---|
| 1 |   |   |   | 5 |   |   |   |   | 10 |   |   |   |   | 15 |   |
| Ile | Ser | Arg | Trp | Asn | Leu | His | Thr | Pro | Ala | His | Thr | Lys | Leu | Leu | Ala |
|   |   |   | 20 |   |   |   |   | 25 |   |   |   |   | 30 |   |   |
| Glu | Gln | Phe | Asn | Ser | Phe | Thr | Cys | Glu | Asn | Asp | Met | Lys | Pro | Met | Tyr |
|   |   |   | 35 |   |   |   |   | 40 |   |   |   |   | 45 |   |   |
| Tyr | Leu | Asp | Arg | Glu | Ala | Asn | Lys | Lys | Asp | Pro | Glu | Lys | Tyr | Asn | Leu |
|   | 50 |   |   |   |   | 55 |   |   |   |   | 60 |   |   |   |   |
| Ser | Pro | Ala | Leu | Thr | Phe | Glu | Asn | Ala | Ile | Pro | Tyr | Leu | Glu | Phe | Ala |
| 65 |   |   |   |   | 70 |   |   |   |   | 75 |   |   |   |   | 80 |
| Lys | Asp | Asn | Lys | Ile | Ala | Met | Arg | Gly | His | Thr | Leu | Val | Trp | His | Asn |
|   |   |   |   | 85 |   |   |   |   | 90 |   |   |   |   | 95 |   |
| Gln | Thr | Pro | Lys | Trp | Phe | Phe | Cys | Glu | Arg | Tyr | Asn | Glu | Asn | Phe | Pro |
|   |   |   | 100 |   |   |   |   | 105 |   |   |   |   | 110 |   |   |
| Met | Ala | Asp | Arg | Glu | Thr | Ile | Leu | Ala | Arg | Leu | Glu | Ser | Tyr | Ile | His |
|   |   |   | 115 |   |   |   |   | 120 |   |   |   |   | 125 |   |   |
| Gly | Val | Leu | Asp | Phe | Val | Gln | Thr | Asn | Tyr | Pro | Gly | Ile | Ile | Tyr | Ala |
|   |   |   | 130 |   |   |   |   | 135 |   |   |   |   | 140 |   |   |
| Trp | Asp | Val | Val | Asn | Glu | Ile | Val | Asp | Glu | Gly | Ala | Phe | Arg | Lys | Ser |
| 145 |   |   |   |   | 150 |   |   |   |   | 155 |   |   |   |   | 160 |
| Ile | Trp | Thr | Glu | Thr | Val | Gly | Glu | Asp | Phe | Phe | Ile | Lys | Ala | Phe | Glu |
|   |   |   |   | 165 |   |   |   |   | 170 |   |   |   |   | 175 |   |
| Phe | Ala | Arg | Lys | Tyr | Ala | Ala | Pro | Glu | Val | Ser | Leu | Phe | Tyr | Asn | Asp |
|   |   |   | 180 |   |   |   |   | 185 |   |   |   |   | 190 |   |   |
| Tyr | Glu | Thr | Ala | Gln | Pro | Trp | Lys | Arg | Asp | Phe | Ile | Leu | Glu | Lys | Val |
|   |   |   | 195 |   |   |   |   | 200 |   |   |   |   | 205 |   |   |
| Leu | Gly | Pro | Leu | Ile | Asp | Lys | Lys | Leu | Ile | Asp | Gly | Met | Gly | Met | Gln |
|   | 210 |   |   |   |   | 215 |   |   |   |   | 220 |   |   |   |   |

| | | | | | | | | | | | | | | |
|---|---|---|---|---|---|---|---|---|---|---|---|---|---|---|
| Ser 225 | His | Leu | Leu | Met | Asp 230 | His | Pro | Asp | Ile | Ser 235 | Glu | Tyr | Arg | Thr | Ala 240 |
| Leu | Glu | Met | Tyr | Gly 245 | Ser | Thr | Gly | Leu | Gln 250 | Ile | His | Ile | Thr | Glu 255 | Leu |
| Asp | Met | His | Asn 260 | Ala | Asp | Pro | Ser | Glu 265 | Ser | Met | His | Ala 270 | Leu | Ala |
| Thr | Arg | Tyr 275 | Gln | Glu | Phe | Phe | Gln 280 | Thr | Tyr | Leu | Asp | Ala 285 | Lys | Lys | Ser |
| Gly | Lys 290 | Ala | Asn | Ile | Thr | Ser 295 | Val | Thr | Phe | Trp | Asn 300 | Leu | Leu | Asp | Glu |
| Asn 305 | Ser | Trp | Leu | Ser | Gly 310 | Phe | Arg | Arg | Glu | Thr 315 | Ser | Tyr | Pro | Leu | Val 320 |
| Phe | Lys | Gly | Lys | Cys 325 | Glu | Ala | Lys | Glu | Ala 330 | Tyr | Tyr | Ala | Val | Leu 335 | Lys |
| Ala | Ala | Val | Ser 340 | Asp | Asp | Ser | Ile | Asp 345 | Lys | Trp | Val | Pro | Asp 350 | Tyr | Ser |
| Glu | Glu | Asp 355 | Tyr | Lys | Leu | Gln | Gly 360 | Met | Pro | Thr | Pro | Asp 365 | Ile | Lys | Arg |
| Phe | Arg 370 | Glu | Asn | Ile | Trp | Gln 375 | Glu | Asn | Glu | Tyr | Asn 380 | Tyr | Glu | Ala | Ser |
| Tyr 385 | Gly | Phe | Ile | Pro | Asn 390 | Leu | Phe |

(2) INFORMATION FOR SEQ ID NO:61:

(i) SEQUENCE CHARACTERISTICS:
        (A) LENGTH: 405 amino acids
        (B) TYPE: amino acid
        (D) TOPOLOGY: both (xi) SEQUENCE DESCRIPTION: SEQ ID NO:61:

| | | | | | | | | | | | | | | |
|---|---|---|---|---|---|---|---|---|---|---|---|---|---|---|
| Asn 1 | Gln | Asn | Asn | Trp 5 | Asn | Gln | Asn | Asn | Gln 10 | Gln | Asn | Ala | Trp | Asn 15 |
| Gly | Trp | Asp | Asn 20 | Asn | Asn | Trp | Asn | Gln 25 | Trp | Gly | Gly | Gln | Asn 30 | Asn |
| Asp | Trp | Asn | Asn 35 | Gln | Gln | Gln | Asn | Asn 40 | Asp | Trp | Asn | Gln 45 | Trp | Asn | Asn |
| Gln | Gly 50 | Gln | Gln | Gln | Asn | Asn 55 | Asp | Trp | Asn | Asn | Gln 60 | Asn | Asn | Trp | Asn |
| Gln 65 | Gly | Gln | Gln | Asn | Asn 70 | Asn | Ser | Ala | Gly 75 | Ser | Ser | Asp | Ser | Leu 80 |
| Lys | Gly | Ala | Phe | Ser 85 | Lys | Tyr | Phe | Lys | Ile 90 | Gly | Thr | Ser | Val | Ser 95 | Pro |
| His | Glu | Leu | Asn 100 | Ser | Gly | Ala | Asp | Phe 105 | Leu | Lys | Lys | His | Tyr 110 | Asn | Ser |
| Ile | Thr | Pro 115 | Glu | Asn | Glu | Leu | Lys 120 | Pro | Glu | Ser | Ile | Leu 125 | Asp | Gln | Gly |
| Ala | Cys 130 | Gln | Gln | Lys | Gly | Asn 135 | Asn | Val | Asn | Thr | Gln 140 | Ile | Ser | Leu | Ser |
| Arg 145 | Ala | Ala | Gln | Thr | Leu 150 | Lys | Phe | Cys | Glu | Gln 155 | Asn | Gly | Ile | Ala | Leu 160 |
| Arg | Gly | His | Thr | Phe 165 | Val | Trp | Tyr | Ser | Gln 170 | Thr | Pro | Asp | Trp | Phe 175 | Phe |
| Arg | Glu | Asn | Phe 180 | Ser | Gln | Asn | Gly | Ala 185 | Tyr | Val | Ser | Lys | Asp 190 | Ile | Met |

|     |     |     |     |     |     |     |     |     |     |     |     |     |     |     |
| --- | --- | --- | --- | --- | --- | --- | --- | --- | --- | --- | --- | --- | --- | --- |
| Asn | Gln | Arg<br>195 | Leu | Glu | Ser | Met | Ile | Lys<br>200 | Asn | Thr | Phe | Ala<br>205 | Ala | Leu | Lys |
| Ser | Gln<br>210 | Tyr | Pro | Asn | Leu<br>215 | Asp | Val | Tyr | Ser | Tyr<br>220 | Asp | Val | Cys | Asn | Glu |
| Leu<br>225 | Phe | Leu | Asn | Asn | Gly<br>230 | Gly | Gly | Met | Arg | Gly<br>235 | Ala | Asp | Asn | Ser | Asn<br>240 |
| Trp | Val | Lys | Ile | Tyr<br>245 | Gly | Asp | Asp | Ser | Phe<br>250 | Val | Ile | Asn | Ala | Phe<br>255 | Lys |
| Tyr | Ala | Arg | Gln<br>260 | Tyr | Ala | Pro | Ala | Gly<br>265 | Cys | Lys | Leu | Tyr | Leu<br>270 | Asn | Asp |
| Tyr | Asn | Glu<br>275 | Tyr | Ile | Pro | Ala | Lys<br>280 | Thr | Asn | Asp | Ile | Tyr<br>285 | Asn | Met | Ala |
| Met | Lys | Leu<br>290 | Lys | Gln | Leu | Gly | Tyr<br>295 | Ile | Asp | Gly | Ile | Gly<br>300 | Met | Gln | Ser |
| His<br>305 | Leu | Ala | Thr | Asn | Tyr<br>310 | Pro | Asp | Ala | Asn | Thr<br>315 | Tyr | Glu | Thr | Ala | Leu<br>320 |
| Lys | Lys | Phe | Leu | Ser<br>325 | Thr | Gly | Leu | Glu | Val<br>330 | Gln | Ile | Thr | Glu | Leu<br>335 | Asp |
| Ile | Thr | Cys | Thr<br>340 | Asn | Ser | Ala | Glu | Gln<br>345 | Ala | Asp | Leu | Tyr | Glu<br>350 | Lys | Ile |
| Phe | Lys | Leu<br>355 | Ala | Met | Gln | Asn | Ser<br>360 | Ala | Gln | Ile | Pro | Ala<br>365 | Val | Thr | Ile |
| Trp | Gly<br>370 | Thr | Gln | Asp | Thr | Val<br>375 | Ser | Trp | Arg | Ser | Ser<br>380 | Gln | Asn | Pro | Leu |
| Leu<br>385 | Phe | Ser | Ala | Gly | Tyr<br>390 | Gln | Pro | Lys | Pro | Ala<br>395 | Tyr | Asp | Arg | Val | Met<br>400 |
| Ala | Leu | Ala | Lys | Xaa<br>405 |     |     |     |     |     |     |     |     |     |     |     |

( 2 ) INFORMATION FOR SEQ ID NO:62:

( i ) SEQUENCE CHARACTERISTICS:
        ( A ) LENGTH: 404 amino acids
        ( B ) TYPE: amino acid
        ( D ) TOPOLOGY: both ( x i ) SEQUENCE DESCRIPTION: SEQ ID NO:62:

|     |     |     |     |     |     |     |     |     |     |     |     |     |     |     |
| --- | --- | --- | --- | --- | --- | --- | --- | --- | --- | --- | --- | --- | --- | --- |
| Asn<br>1 | Ala | Trp | Gln | Trp<br>5 | Val | Gly | Asn | Met | Arg<br>10 | Trp | Val | Leu | Pro | Phe<br>15 |
| Gly | Ala | Ser | Arg<br>20 | Gly | Gly | Ile | Arg | Ala<br>25 | Gly | Gln | Gly | Asp | Ser<br>30 | Leu | Ile |
| Ala | Phe | Ala<br>35 | Gly | Ala | Glu | Ser | Thr<br>40 | Asn | Ala | Ala | Ala | Asn<br>45 | Ile | Arg | Ser |
| Leu | Ala<br>50 | Glu | Ala | Lys | Asp | Tyr<br>55 | Phe | Lys | Ile | Gly | Ala<br>60 | Ala | Val | Glu | Pro |
| Tyr<br>65 | Arg | Leu | Ser | Asp | Ser<br>70 | Gly | Thr | Tyr | Ile | Leu<br>75 | Lys | Lys | His | Phe | Asn<br>80 |
| Met | Thr | Ala | Glu | Asn<br>85 | Glu | Met | Lys | Pro | Leu<br>90 | Asp | Ala | Leu | Gln | Pro<br>95 | Glu |
| Gly | Thr | Ser | Asn<br>100 | Gln | Phe | Asn | Phe | Ser<br>105 | Asn | Ala | Asp | Arg | Ile<br>110 | Val | Glu |
| Phe | Ala | Gln<br>115 | Asn | Gly | Met | Leu | Arg<br>120 | Gly | His | Thr | Leu | Val<br>125 | Trp | His | Asn |
| Gln | Thr<br>130 | Pro | Asp | Trp | Phe | Phe<br>135 | Leu | Asp | Gly | Met | Val<br>140 | Glu | Thr | Asp | Pro |
| Lys | Arg | Glu | Ser | Asp | Leu | Leu | Leu | Gln | Arg | Leu | Glu | Asn | His | Ile | Thr |

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Val | Met | His | Tyr | Lys | Thr | Tyr | Pro | Gly | Lys | Ser | Trp | Asp | Val | Val | Asn |
|     |     |     |     | 165 |     |     |     |     | 170 |     |     |     |     | 175 |     |
| Glu | Ala | Phe | Gly | Asp | Asp | Gly | Asp | Asn | Gly | Gly | Leu | Arg | Arg | Ser | Trp |
|     |     |     | 180 |     |     |     |     | 185 |     |     |     |     | 190 |     |     |
| Gln | Ile | Ile | Gly | Asn | Asp | Tyr | Ile | Glu | Val | Ala | Phe | Arg | Tyr | Ala | Arg |
|     |     | 195 |     |     |     |     | 200 |     |     |     |     | 205 |     |     |     |
| Glu | Tyr | Ala | Asp | Pro | Asp | Ala | Lys | Leu | Phe | Tyr | Asn | Asp | Tyr | Asn | Glu |
|     | 210 |     |     |     |     | 215 |     |     |     |     | 220 |     |     |     |     |
| Trp | Pro | Trp | Ala | Lys | Thr | Asp | Ala | Leu | Tyr | Asn | Val | Lys | Asp | Leu | Lys |
| 225 |     |     |     |     | 230 |     |     |     |     | 235 |     |     |     |     | 240 |
| Glu | Arg | Gly | Val | Pro | Ile | Asp | Gly | Val | Gly | Phe | Gln | Ser | His | Phe | Asn |
|     |     |     |     | 245 |     |     |     |     | 250 |     |     |     |     | 255 |     |
| Ile | Gly | Trp | Pro | Pro | Tyr | Ile | Ser | Asn | Arg | Thr | Leu | Lys | Phe | Ala | Ser |
|     |     |     | 260 |     |     |     |     | 265 |     |     |     |     | 270 |     |     |
| Leu | Ser | Gly | Asp | Ile | Ile | Thr | Glu | Leu | Asp | Ile | Ser | Leu | Tyr | Asn | Trp |
|     |     | 275 |     |     |     |     | 280 |     |     |     |     | 285 |     |     |     |
| Asp | Tyr | Tyr | Asp | Asp | Ile | Pro | Glu | Leu | Leu | Gln | Ala | Gln | Ala | Ala | Arg |
|     | 290 |     |     |     |     | 295 |     |     |     |     | 300 |     |     |     |     |
| Tyr | Lys | Glu | Phe | Ala | Cys | Leu | Ala | Val | Ser | Glu | Lys | Ala | Val | Ile | Thr |
| 305 |     |     |     |     | 310 |     |     |     |     | 315 |     |     |     |     | 320 |
| Val | Thr | Phe | Trp | Gly | Ile | Ser | Asp | Tyr | Ser | Trp | Leu | Ser | Gly | Phe | Arg |
|     |     |     |     | 325 |     |     |     |     | 330 |     |     |     |     | 335 |     |
| Lys | Glu | Asp | Trp | Ala | Pro | Leu | Leu | Phe | Asp | Asn | Tyr | Gln | Pro | Lys | Pro |
|     |     |     | 340 |     |     |     |     | 345 |     |     |     |     | 350 |     |     |
| Ala | Tyr | Trp | Ala | Val | Asp | Ala | Leu | Gly | Thr | Ser | Glu | Pro | Pro | Pro | Thr |
|     |     | 355 |     |     |     |     | 360 |     |     |     |     | 365 |     |     |     |
| Pro | Ala | Pro | Gly | Val | Gly | Ser | Gly | Arg | Leu | Tyr | Asp | Val | Pro | Asp | Ser |
|     | 370 |     |     |     |     | 375 |     |     |     |     | 380 |     |     |     |     |
| Thr | Asp | Gly | Thr | Thr | Val | Lys | Thr | Asn | Gln | Gln | Trp | Thr | Thr | Ser | Glu |
| 385 |     |     |     |     | 390 |     |     |     |     | 395 |     |     |     |     | 400 |
| Tyr | Gly | Asn | Lys |

(2) INFORMATION FOR SEQ ID NO:63:

(i) SEQUENCE CHARACTERISTICS:
        (A) LENGTH: 420 amino acids
        (B) TYPE: amino acid
        (D) TOPOLOGY: both (xi) SEQUENCE DESCRIPTION: SEQ ID NO:63:

| Met | Gly | Ser | Tyr | Ala | Leu | Pro | Arg | Ser | Gly | Val | Arg | Arg | Ser | Ile | Arg |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Val | Leu | Leu | Ala | Ala | Leu | Val | Val | Gly | Val | Leu | Gly | Thr | Ala | Thr | Ala |
|     |     |     |     | 20 |     |     |     |     | 25 |     |     |     |     | 30 |     |
| Leu | Ile | Ala | Pro | Pro | Gly | Ala | His | Ala | Ala | Glu | Ser | Thr | Leu | Gly | Ala |
|     |     |     | 35 |     |     |     |     | 40 |     |     |     |     | 45 |     |     |
| Ala | Ala | Ala | Gln | Ser | Gly | Arg | Tyr | Phe | Gly | Thr | Ala | Ile | Ala | Ser | Gly |
|     |     | 50 |     |     |     |     | 55 |     |     |     |     | 60 |     |     |     |
| Arg | Leu | Ser | Asp | Ser | Thr | Tyr | Thr | Ser | Ile | Ala | Gly | Arg | Glu | Phe | Asn |
| 65 |     |     |     |     | 70 |     |     |     |     | 75 |     |     |     |     | 80 |
| Met | Val | Thr | Ala | Glu | Asn | Glu | Met | Lys | Ile | Asp | Ala | Thr | Glu | Pro | Gln |
|     |     |     |     | 85 |     |     |     |     | 90 |     |     |     |     | 95 |     |
| Arg | Gly | Gln | Phe | Asn | Phe | Ser | Ser | Ala | Asp | Arg | Val | Tyr | Asn | Trp | Ala |
|     |     |     | 100 |     |     |     |     | 105 |     |     |     |     | 110 |     |     |

```
Val  Gln  Asn  Gly  Lys  Gln  Val  Arg  Gly  His  Thr  Leu  Ala  Trp  His  Ser
          115                 120                      125

Gln  Gln  Pro  Gly  Trp  Met  Gln  Ser  Leu  Ser  Gly  Arg  Pro  Leu  Arg  Gln
     130                      135                      140

Ala  Met  Ile  Asp  His  Ile  Asn  Gly  Val  Met  Ala  His  Tyr  Lys  Gly  Lys
145                           150                     155                      160

Ile  Val  Gln  Trp  Asp  Val  Val  Asn  Glu  Ala  Phe  Ala  Asp  Gly  Ser  Ser
               165                      170                          175

Gly  Ala  Arg  Arg  Asp  Ser  Asn  Leu  Gln  Arg  Ser  Gly  Asn  Asp  Trp  Ile
               180                 185                           190

Glu  Val  Ala  Phe  Arg  Thr  Ala  Arg  Ala  Ala  Asp  Pro  Ser  Ala  Lys  Leu
          195                      200                     205

Cys  Tyr  Asn  Asp  Tyr  Asn  Val  Glu  Asn  Trp  Thr  Trp  Ala  Lys  Thr  Gln
          210                 215                      220

Ala  Met  Tyr  Asn  Met  Val  Arg  Asp  Phe  Lys  Gln  Arg  Gly  Val  Pro  Ile
225                      230                 235                           240

Asp  Cys  Val  Gly  Phe  Gln  Ser  His  Phe  Asn  Ser  Gly  Ser  Pro  Tyr  Asn
               245                      250                           255

Ser  Asn  Phe  Arg  Thr  Thr  Leu  Gln  Asn  Phe  Ala  Ala  Leu  Gly  Val  Asp
               260                 265                     270

Val  Ala  Ile  Thr  Glu  Leu  Asp  Ile  Gln  Gly  Ala  Pro  Ala  Ser  Thr  Tyr
          275                      280                     285

Ala  Asn  Val  Thr  Asn  Asp  Cys  Leu  Ala  Val  Ser  Arg  Cys  Leu  Gly  Ile
          290                 295                     300

Thr  Val  Trp  Gly  Val  Arg  Asp  Ser  Asp  Ser  Trp  Arg  Ser  Glu  Gln  Thr
305                      310                     315                           320

Pro  Leu  Leu  Phe  Asn  Asn  Asp  Gly  Ser  Lys  Lys  Ala  Ala  Tyr  Thr  Ala
               325                      330                           335

Val  Leu  Asp  Ala  Leu  Asn  Gly  Gly  Asp  Ser  Ser  Glu  Pro  Pro  Ala  Asp
          340                      345                           350

Gly  Gly  Gln  Ile  Lys  Gly  Val  Gly  Ser  Gly  Arg  Cys  Leu  Asp  Val  Pro
          355                      360                     365

Asp  Ala  Ser  Thr  Ser  Asp  Gly  Thr  Gln  Leu  Gln  Leu  Trp  Asp  Cys  His
          370                      375                     380

Ser  Gly  Thr  Asn  Gln  Gln  Trp  Ala  Ala  Thr  Asp  Ala  Gly  Glu  Leu  Arg
385                      390                     395                           400

Val  Tyr  Gly  Asp  Lys  Cys  Leu  Asp  Ala  Ala  Gly  Thr  Ser  Asn  Gly  Ser
               405                      410                           415

Lys  Val  Gln  Ile
               420
```

( 2 ) INFORMATION FOR SEQ ID NO:64:

( i ) SEQUENCE CHARACTERISTICS:
        ( A ) LENGTH: 419 amino acids
        ( B ) TYPE: amino acid
        ( D ) TOPOLOGY: both ( x i ) SEQUENCE DESCRIPTION: SEQ ID NO:64:

```
Met  Pro  Ile  Asn  Val  Met  Pro  Arg  Pro  Gly  Ala  Arg  Lys  Arg  Ala  Leu
1                   5                   10                          15

Leu  Ala  Gly  Ala  Val  Gly  Leu  Leu  Thr  Ala  Ala  Ala  Leu  Val  Ala
               20                  25                      30

Pro  Ser  Pro  Ala  Val  Ala  Ala  Glu  Ser  Thr  Leu  Gly  Ala  Ala  Ala  Ala
          35                      40                      45

Gln  Ser  Gly  Arg  Tyr  Phe  Gly  Thr  Ala  Ile  Ala  Ser  Gly  Arg  Leu  Asn
```

| | | | | 50 | | | | | 55 | | | | | 60 | |
|---|---|---|---|---|---|---|---|---|---|---|---|---|---|---|---|
| Asp 65 | Ser | Thr | Tyr | Thr | Thr 70 | Ile | Ala | Asn | Arg | Glu 75 | Phe | Asn | Met | Val | Thr 80 |
| Ala | Glu | Asn | Glu | Met 85 | Lys | Ile | Asp | Ala | Thr 90 | Glu | Pro | Asn | Arg | Gly 95 | Gln |
| Phe | Asn | Phe | Ser 100 | Ser | Ala | Asp | Arg | Ile 105 | Tyr | Asn | Trp | Ala | Val 110 | Gln | Asn |
| Gly | Lys | Gln 115 | Val | Arg | Gly | His | Thr 120 | Leu | Ala | Trp | His | Ser 125 | Gln | Gln | Pro |
| Gly | Trp 130 | Met | Gln | Ser | Leu | Ser 135 | Gly | Ser | Ser | Leu | Arg 140 | Gln | Ala | Met | Ile |
| Asp 145 | His | Ile | Asn | Gly | Val 150 | Met | Ala | His | Tyr | Lys 155 | Gly | Lys | Ile | Val | Gln 160 |
| Trp | Asp | Val | Val | Asn 165 | Glu | Ala | Phe | Ala | Asp 170 | Gly | Asn | Ser | Gly | Gly 175 | Arg |
| Arg | Asp | Ser | Asn 180 | Leu | Gln | Arg | Thr | Gly 185 | Asn | Asp | Trp | Ile | Glu 190 | Val | Ala |
| Phe | Arg | Thr 195 | Ala | Arg | Asn | Ala | Asp 200 | Pro | Asn | Ala | Lys | Leu 205 | Cys | Tyr | Asn |
| Asp | Tyr 210 | Asn | Ile | Glu | Asn | Trp 215 | Asn | Trp | Ala | Lys | Thr 220 | Gln | Gly | Val | Tyr |
| Asn 225 | Met | Val | Arg | Asp | Phe 230 | Lys | Gln | Arg | Gly | Val 235 | Pro | Ile | Asp | Cys | Val 240 |
| Gly | Phe | Gln | Ser | His 245 | Phe | Asn | Ser | Gly | Ser 250 | Pro | Tyr | Asn | Ser | Asn 255 | Phe |
| Arg | Thr | Thr | Leu 260 | Gln | Asn | Phe | Ala | Ala 265 | Leu | Gly | Val | Asp | Val 270 | Ala | Ile |
| Thr | Glu | Leu 275 | Asp | Ile | Gln | Gly | Ala 280 | Ser | Pro | Thr | Thr | Tyr 285 | Ala | Asn | Val |
| Val | Asn 290 | Asp | Cys | Leu | Ala | Val 295 | Ser | Arg | Cys | Leu | Gly 300 | Ile | Thr | Val | Trp |
| Gly 305 | Val | Arg | Asp | Thr | Asp 310 | Ser | Trp | Arg | Ser | Asp 315 | Gln | Thr | Pro | Leu | Leu 320 |
| Phe | Asp | Gly | Asn | Gly 325 | Asn | Lys | Lys | Ala | Ala 330 | Tyr | Ser | Ala | Val | Leu 335 | Asn |
| Ala | Leu | Asn | Gly 340 | Gly | Gly | Thr | Ser | Glu 345 | Pro | Pro | Pro | Ala | Ser 350 | Asp | Ala |
| Gly | Thr | Ile 355 | Lys | Gly | Val | Gly | Ser 360 | Gly | Arg | Cys | Leu | Asp 365 | Val | Pro | Asn |
| Ala | Ser | Thr 370 | Ser | Asp | Gly | Val 375 | Gln | Leu | Gln | Leu | Trp 380 | Asp | Cys | His | Gly |
| Gly 385 | Thr | Asn | Gln | Gln | Trp 390 | Thr | Tyr | Thr | Asp | Ser 395 | Gln | Glu | Leu | Arg | Val 400 |
| Tyr | Gly | Asn | Lys | Cys 405 | Leu | Asp | Ala | Ala | Gly 410 | Thr | Gly | Asn | Gly | Thr 415 | Lys |
| Val | Gln | Ile | | | | | | | | | | | | | |

( 2 ) INFORMATION FOR SEQ ID NO:65:

( i ) SEQUENCE CHARACTERISTICS:
  ( A ) LENGTH: 134 base pairs
  ( B ) TYPE: nucleic acid
  ( C ) STRANDEDNESS: both
  ( D ) TOPOLOGY: both ( x i ) SEQUENCE DESCRIPTION: SEQ ID NO:65:

```
GGCGGCGGCA CCTCCGAGCC GCCGCCCGCC TCCGACGCCG GGACGATCAA GGGCGTCGGC        60

TCGGCCGCTG CCTGGACGTG CCCAACGCCA GCACCAGCGA CGGCGTCCAG CTCCAGCTGT       120

GGGACTGCCA CGGC                                                         134
```

( 2 ) INFORMATION FOR SEQ ID NO:66:

( i ) SEQUENCE CHARACTERISTICS:
        ( A ) LENGTH: 420 amino acids
        ( B ) TYPE: amino acid
        ( D ) TOPOLOGY: both ( x i ) SEQUENCE DESCRIPTION: SEQ ID NO:66:

```
Met Gly Ser Tyr Ala Leu Pro Arg Ser Gly Val Arg Arg Ser Ile Arg
 1               5                  10                  15

Val Leu Leu Ala Ala Leu Val Val Gly Val Leu Gly Thr Ala Thr Ala
            20                  25                  30

Leu Ile Ala Pro Pro Gly Ala His Ala Ala Glu Ser Thr Leu Gly Ala
        35                  40                  45

Ala Ala Ala Gln Ser Gly Arg Tyr Phe Gly Thr Ala Ile Ala Ser Gly
    50                  55                  60

Arg Leu Ser Asp Ser Thr Tyr Thr Ser Ile Ala Gly Arg Glu Phe Asn
65                  70                  75                  80

Met Val Thr Ala Glu Asn Glu Met Lys Ile Asp Ala Thr Glu Pro Gln
                85                  90                  95

Arg Gly Gln Phe Asn Phe Ser Ser Ala Asp Arg Val Tyr Asn Trp Ala
               100                 105                 110

Val Gln Asn Gly Lys Gln Val Arg Gly His Thr Leu Ala Trp His Ser
            115                 120                 125

Gln Gln Pro Gly Trp Met Gln Ser Leu Ser Gly Arg Pro Leu Arg Gln
    130                 135                 140

Ala Met Ile Asp His Ile Asn Gly Val Met Ala His Tyr Lys Gly Lys
145                 150                 155                 160

Ile Val Gln Trp Asp Val Val Asn Glu Ala Phe Ala Asp Gly Ser Ser
                165                 170                 175

Gly Ala Arg Arg Asp Ser Asn Leu Gln Arg Ser Gly Asn Asp Trp Ile
            180                 185                 190

Glu Val Ala Phe Arg Thr Ala Arg Ala Ala Asp Pro Ser Ala Lys Leu
        195                 200                 205

Cys Tyr Asn Asp Tyr Asn Val Glu Asn Trp Thr Trp Ala Lys Thr Gln
    210                 215                 220

Ala Met Tyr Asn Met Val Arg Asp Phe Lys Gln Arg Gly Val Pro Ile
225                 230                 235                 240

Asp Cys Val Gly Phe Gln Ser His Phe Asn Ser Gly Ser Pro Tyr Asn
                245                 250                 255

Ser Asn Phe Arg Thr Thr Leu Gln Asn Phe Ala Ala Leu Gly Val Asp
            260                 265                 270

Val Ala Ile Thr Glu Leu Asp Ile Gln Gly Ala Pro Ala Ser Thr Tyr
        275                 280                 285

Ala Asn Val Thr Asn Asp Cys Leu Ala Val Ser Arg Cys Leu Gly Ile
    290                 295                 300

Thr Val Trp Gly Val Arg Asp Ser Asp Ser Trp Arg Ser Glu Gln Thr
305                 310                 315                 320

Pro Leu Leu Phe Asn Asn Asp Gly Ser Lys Lys Ala Ala Tyr Thr Ala
                325                 330                 335
```

| | | | | | | | | | | | | | | |
|---|---|---|---|---|---|---|---|---|---|---|---|---|---|---|
| Val | Leu | Asp | Ala | Leu | Asn | Gly | Gly | Asp | Ser | Ser | Glu | Pro | Pro | Ala | Asp |
| | | | 340 | | | | | 345 | | | | | 350 | | |
| Gly | Gly | Gln | Ile | Lys | Gly | Val | Gly | Ser | Gly | Arg | Cys | Leu | Asp | Val | Pro |
| | | | 355 | | | | 360 | | | | | 365 | | | |
| Asp | Ala | Ser | Thr | Ser | Asp | Gly | Thr | Gln | Leu | Gln | Leu | Trp | Asp | Cys | His |
| | | 370 | | | | | 375 | | | | | 380 | | | |
| Ser | Gly | Thr | Asn | Gln | Gln | Trp | Ala | Ala | Thr | Asp | Ala | Gly | Glu | Leu | Arg |
| 385 | | | | | 390 | | | | | 395 | | | | | 400 |
| Val | Tyr | Gly | Asp | Lys | Cys | Leu | Asp | Ala | Ala | Gly | Thr | Ser | Asn | Gly | Ser |
| | | | | 405 | | | | | 410 | | | | | 415 | |
| Lys | Val | Gln | Ile | | | | | | | | | | | | |
| | | | 420 | | | | | | | | | | | | |

(2) INFORMATION FOR SEQ ID NO:67:

(i) SEQUENCE CHARACTERISTICS:
     (A) LENGTH: 419 amino acids
     (B) TYPE: amino acid
     (D) TOPOLOGY: both (xi) SEQUENCE DESCRIPTION: SEQ ID NO:67:

| | | | | | | | | | | | | | | |
|---|---|---|---|---|---|---|---|---|---|---|---|---|---|---|---|
| Met | Pro | Ile | Asn | Val | Met | Pro | Arg | Pro | Gly | Ala | Arg | Lys | Arg | Ala | Leu |
| 1 | | | | 5 | | | | | 10 | | | | | 15 | |
| Leu | Ala | Gly | Ala | Val | Gly | Leu | Leu | Thr | Ala | Ala | Ala | Ala | Leu | Val | Ala |
| | | | 20 | | | | | 25 | | | | | 30 | | |
| Pro | Ser | Pro | Ala | Val | Ala | Ala | Glu | Ser | Thr | Leu | Gly | Ala | Ala | Ala | Ala |
| | | 35 | | | | | 40 | | | | | 45 | | | |
| Gln | Ser | Gly | Arg | Tyr | Phe | Gly | Thr | Ala | Ile | Ala | Ser | Gly | Arg | Leu | Asn |
| | 50 | | | | | 55 | | | | | 60 | | | | |
| Asp | Ser | Thr | Tyr | Thr | Thr | Ile | Ala | Asn | Arg | Glu | Phe | Asn | Met | Val | Thr |
| 65 | | | | | 70 | | | | | 75 | | | | | 80 |
| Ala | Glu | Asn | Glu | Met | Lys | Ile | Asp | Ala | Thr | Glu | Pro | Asn | Arg | Gly | Gln |
| | | | | 85 | | | | | 90 | | | | | 95 | |
| Phe | Asn | Phe | Ser | Ser | Ala | Asp | Arg | Ile | Tyr | Asn | Trp | Ala | Val | Gln | Asn |
| | | | | 100 | | | | | 105 | | | | | 110 | |
| Gly | Lys | Gln | Val | Arg | Gly | His | Thr | Leu | Ala | Trp | His | Ser | Gln | Gln | Pro |
| | | | 115 | | | | | 120 | | | | | 125 | | |
| Gly | Trp | Met | Gln | Ser | Leu | Ser | Gly | Ser | Ser | Leu | Arg | Gln | Ala | Met | Ile |
| | | 130 | | | | | 135 | | | | | 140 | | | |
| Asp | His | Ile | Asn | Gly | Val | Met | Ala | His | Tyr | Lys | Gly | Lys | Ile | Val | Gln |
| 145 | | | | | 150 | | | | | 155 | | | | | 160 |
| Trp | Asp | Val | Val | Asn | Glu | Ala | Phe | Ala | Asp | Gly | Asn | Ser | Gly | Gly | Arg |
| | | | | 165 | | | | | 170 | | | | | 175 | |
| Arg | Asp | Ser | Asn | Leu | Gln | Arg | Thr | Gly | Asn | Asp | Trp | Ile | Glu | Val | Ala |
| | | | 180 | | | | | 185 | | | | | 190 | | |
| Phe | Arg | Thr | Ala | Arg | Asn | Ala | Asp | Pro | Asn | Ala | Lys | Leu | Cys | Tyr | Asn |
| | | 195 | | | | | 200 | | | | | 205 | | | |
| Asp | Tyr | Asn | Ile | Glu | Asn | Trp | Asn | Trp | Ala | Lys | Thr | Gln | Gly | Val | Tyr |
| | 210 | | | | | 215 | | | | | 220 | | | | |
| Asn | Met | Val | Arg | Asp | Phe | Lys | Gln | Arg | Gly | Val | Pro | Ile | Asp | Cys | Val |
| 225 | | | | | 230 | | | | | 235 | | | | | 240 |
| Gly | Phe | Gln | Ser | His | Phe | Asn | Ser | Gly | Ser | Pro | Tyr | Asn | Ser | Asn | Phe |
| | | | | 245 | | | | | 250 | | | | | 255 | |
| Arg | Thr | Thr | Leu | Gln | Asn | Phe | Ala | Ala | Leu | Gly | Val | Asp | Val | Ala | Ile |
| | | | 260 | | | | | 265 | | | | | 270 | | |
| Thr | Glu | Leu | Asp | Ile | Gln | Gly | Ala | Ser | Pro | Thr | Thr | Tyr | Ala | Asn | Val |

-continued

```
                         275                          280                          285
    Val Asn Asp Cys Leu Ala Val Ser Arg Cys Leu Gly Ile Thr Val Trp
        290                     295                 300
    Gly Val Arg Asp Thr Asp Ser Trp Arg Ser Asp Gln Thr Pro Leu Leu
    305                     310                 315                         320
    Phe Asp Gly Asn Gly Asn Lys Lys Ala Ala Tyr Ser Ala Val Leu Asn
                        325                 330                         335
    Ala Leu Asn Gly Gly Gly Thr Ser Glu Pro Pro Pro Ala Ser Asp Ala
                    340                 345                     350
    Gly Thr Ile Lys Gly Val Gly Ser Gly Arg Cys Leu Asp Val Pro Asn
                355                 360                 365
    Ala Ser Thr Ser Asp Gly Val Gln Leu Gln Leu Trp Asp Cys His Gly
        370                 375                 380
    Gly Thr Asn Gln Gln Trp Thr Tyr Thr Asp Ser Gln Glu Leu Arg Val
    385                 390                 395                         400
    Tyr Gly Asn Lys Cys Leu Asp Ala Ala Gly Thr Gly Asn Gly Thr Lys
                    405                 410                     415
    Val Gln Ile
            419
```

THERMOSTABLE XYLANASE DNA, PROTEIN AND METHODS OF USE

FIELD OF THE INVENTION

The present invention is in the area of thermostabile enzymes, and the use of same. Especially, the invention is in the area of xylanases that are active at a low pH and high temperature. The compositions of the invention are useful to modify plant biomass properties, especially to reduce the lignin content. The invention is also directed to a method for biobleaching using the enzyme compositions of the invention.

BACKGROUND OF THE INVENTION

Xylan, a major component of hemicellulose, is a polymer consisting of a backbone of β(1,4)-linked D-xylose residues (often acetylated) with α-L-arabinofuranose and glucuronic acid side chains (Timell, T. E., et al., *Wood Sci. Technol.* 1:45–70 (1967)). After cellulose, xylan is the second most abundant carbohydrate fraction of plant biomass. Xylan has recently received increased attention as a renewable bioresource.

Being complex, more than one enzyme is required to completely degrade xylan to soluble monomers. Xylan can be hydrolyzed by many hemicellulases, such as, for example, β-1,4-xylanases (EC 3.2.1.8), β-xylosidases and several debranching enzymes (Biely, P., *Trends Biotechnol* 3:286–290 (1985); Dekker, R. F. H., in Hignehi, T., ed., *Biosynthesis and biodegradation of wood components* (Academic Press Inc., Orlando), pp. 505–533 (1985); Woodward, J., *Top Enzyme Ferment. Biotechnol.* 8:9–30 (1984)). The activities of these enzymes play an important role in the decomposition of soil plant litter and have been extensively studied both in bacteria and fungi (Wong, K. K. Y. et al., *Microbiol. Rev.* 52:305–317 (1988); Poutanen, K. et al., in *Enzymes in biomass conversion* (ACS Symposium series 460), Leatham & Himmel, eds., American Chemical Society, Washington, D.C. (1991), pp.426–436; Gilbert & Hazlewood, *J. Gen. Microbiol.* 139:187–194 (1993)).

Various microorganisms secrete enzymes that are capable of degrading xylans, and xylanases have been found in both prokaryotes and eukaryotes (Dekker, R. F. H., Richards, G. N., *Adv. Carbohydrate Chem. Biochem.* 32:277–352 (1976)). Xylanolytic micro-organisms often produce multiple xylanases to attack the different bonds in these molecules. All the xylanases so far characterized fall into two classes: the high $M_r$/low pI class and the low $M_r$/high pI class which coincide, respectively, with the families 10 and 11 of glycosyl hydrolases (Henrissat & Bairoch, *Biochem. J.* 293:781–788 (1993)).

The cloning of xylanases has been reported from Actinomadura sp. FC7 (Ethier, J. -F. et al., in: *Industrial Microorganisms: Basic and Applied Molecular Genetics,* R. Baltz et al., eds, (Proc. 5th ASM Conf. Gen. Mol. Biol. Indust. Microorg., Oct. 11–15, 1992, Bloomington, Ind., poster C25); bacteria (e.g. Ghangas, G. S. et al., *J. Bacteriol.* 171:2963–2969 (1989); Lin, L. -L., Thomson, J. A., *Mol. Gen. Genet.* 228:55–61 (1991); Shareck, F. et al., *Gene* 107:75–82 (1991); Scheirlinck, T. et al., *Appl Microbiol Biotechnol.* 33:534–541 (1990); Whitehead, T. R., Lee, D. A., *Curr. Microbiol.* 23:15–19 (1991)); and fungi (Boucher, F. et al., *Nucleic Acids Res.* 16:9874 (1988); Ito, K. et al., *Biosci. Biotec. Biochem.* 56:906–912 (1992); Maat, J. et al., in Visser, J. et al., eds., *Xylans and Xylanases* (Elsevier Science, Amsterdam), pp. 349–360 (1992); van den Broeck, H. et al., EP 463,706 A1 (1992), WO 93/25671 and WO 93/25693).

The xylan-containing hemicelluloses in plant biomass are tightly bound to cellulose and lignin. In the pulp and paper industry, in chemical pulping (cooking) of the wood, the major part of the lignin is extracted to get acceptable cellulose pulp product. However, the resulting pulp is brown, mainly because of the small portion of the lignin still remaining in the pulp after cooking. This residual lignin is traditionally removed in a multi-stage bleaching procedure using typically a combination of chlorine chemicals and extraction stages. Peroxide, oxygen and ozone are also used when the use of the chlorine chemicals is wanted to be reduced or avoided totally.

Hemicellulases can be used in enzyme-aided bleaching of pulps to decrease chemical dosage in subsequent bleaching or to increase brightness of the pulp (Kantelinen et al., International Pulp Bleaching Conference, Tappi Proceedings, 1–5 (1988); Viikari et al., *Paper and Timber* 7:384–389 (1991); and Kantelinen et al., "Enzymes in bleaching of kraft pulp," Dissertation for the degree of Doctor of Technology, Technical Research Centre of Finland, VTT Publications 114, Espoo, 1992). Naturally, in this use, the hemicellulose should be free of cellulases, which would harm the cellulose fibers.

The use of hemicellulose hydrolyzing enzymes in different bleaching sequences is discussed in WO 89/08738, EP 383,999, WO 91/02791, EP 395,792, EP 386,888, EP 473, 545, EP 489,104 and WO 91/05908.

Other industrial applications for hemicellulolytic enzymes are in the production of thermo-mechanical pulps, where the aim of the use of hemicellulolytic enzymes is decreased energy consumption. Hemicellulolytic enzymes can be used to improve drainage of recycled pulp or hemicellulolytic enzymes can be used in the production of dissolving pulps (Viikari et al., "Hemicellulases for Industrial Applications, " In: *Bioconversion of Forest and Agricultural Wastes,* Saddler, J., ed., CAB International, USA (1993)).

The use of hemicellulolytic enzymes for improved water removal from mechanical pulp is discussed in EP 262,040, EP 334,739 and EP 351,655 and DE 4,000,558). When the hydrolysis of biomass to liquid fuels or chemicals is considered, the conversion of both cellulose and hemicellulose is essential to obtain a high yield (Viikari et al., "Hemicellulases for Industrial Applications," In: *Bioconversion of Forest and Agricultural Wastes,* Saddler, J., ed., CAB International, USA (1993)). Also, in the feed industry, there is a need to use a suitable combination of enzyme activities to degrade the high β-glucan and hemicellulose containing substrate.

To be amenable to enzymatic hydrolysis in vitro, the cellulose-hemicellulose-lignin matrix must be chemically pretreated. One of such procedures involves a thermo-mechanical steam treatment followed by extraction with hot water (Chahal, D. S. et al., *J. Indust. Microbiol.* 1:355–361 (1987)). A mildly acidic liquor is obtained, which contains water-soluble hemicellulose chains and some lignin derivatives.

However, to ensure further enzymatic hydrolysis of the xylan chains into oligomers or monomers, enzyme systems that are efficient at conditions combining high temperature (such as 70° C.) and moderately acidic pH (around 4.0) are needed. The combination of these two parameters seems however to be harmful for the majority of known xylanases. For instance, at pH 4, xylanase II from the mesophilic actinomycete *Streptomyces roseiscleroticus* (a low $M_r$/high pI enzyme) retains less than 5% of the activity it had at pH 6.0–6.5 (Grabski & Jeffries, *Appl. Environ. Microbiol.* 57:987–992 (1991)). The crude xylanase from *Aureobasidium pullulans* (Myburgh, J. et al., *Proc. Biochem.* 26:343–348 (1991)) is acidophilic, having a pH optimum between 3.5 and 4.0 but its activity sharply decreases at temperatures higher than 35° C. The thermostable xylanase from the fungus *Thermoascus aurantiacus* retains at pH 3.5, only 12% of its maximal activity (Tan L. U. L. et al., *Can. J. Microbiol.* 33:689–692 (1987)). Another xylanase, a high $M_r$/low pI enzyme from the extremophile bacterium "*Caldocellum saccharolyticum*" was shown to be very stable at 60° C. but retained little activity below pH 5 (Lüthi, E. et al., *Appl. Environ. Microbiol.* 56:2677–2683 (1990); Lüthi, E. et al., *Appl. Environ. Microbiol.* 56:1017–1024 (1990). Crude xylanases from various Actinomadura isolates were stable for many hours when incubated at 70°–75° C., but retained less than 15% of their activity at pH 4.0–4.5 and 70° C. (Holtz, C. et al., *Antonie van Leeuwenhoek* 59:1–7 (1991)).

Thus, there is a need for enzyme preparations that contain xylanases which retain activity under industrial ambient conditions. Especially in the paper manufacturing industry, there is a need for xylanase preparations that are functional in the high temperature, acidic liquor produced by thermomechanical steam treatment and hot water extraction.

SUMMARY OF THE INVENTION

Recognizing the importance of developing an environmentally safe and economical method of chemically modifying plant biomass so that it may be enzymatically treated under harsh conditions of high temperature and low pH, processes such as those employed by the paper manufacturing industry, the inventors have searched for a new microbe that might be a source of such enzymes.

These studies have resulted in the isolation and identification of a novel strain of thermophilic actinomycete, Actinomadura sp. FC7. Actinomadura sp. FC7 expresses two unique xylanases, XYL I and XYL II that retain a large amount of their enzymatic activity at high temperatures and low pH.

The invention is further directed to DNA encoding XYL I and XYL II, and to recombinant hosts transformed with such DNA.

The invention is further directed to purified XYL I and XYL II, and to enzyme preparations containing XYL I, XYL II, or mixtures of XYL I and XYL II.

The invention is further directed to a method of treating plant biomass with the enzyme preparations of the invention, especially a method of biobleaching.

BRIEF DESCRIPTION OF THE DRAWINGS

FIG. 6 shows the partial nucleotide sequence of the pJF6 insert (xln2) beginning at the NruI site shown in FIG. 5. The amino acid sequence of Xyl II begins at nucleotide 521. The -35 (TTGACG) and -10 (CACAAT) promoter regions, the ribosome binding site (RBS: GGAGGA), and the initiation codon (CIT: GTG) are shown in bold.

FIG. 7 is a comparison of the RBS of 40 streptomycetes genes versus that for xlnII as encoded by the pJF6 xylanase gene. The nucleotides corresponding to the RBSs are underligned, while those in bold identify the translation initiation codon.

FIG. 8 shows a partial amino acid sequence of XYL II on which the signal peptide is located. The long sequence of hydrophobic amino acids is shown in bold. The characteristic arginines (R) usually found in the hydrophilic region are underlined. The arrow indicates the possible cleavage site of the peptidase signal, bordered by a proline (P).

FIG. 9 shows a comparison of nucleotide sequence homology between the streptomycetes promoters having a spacing of 16 nucleotides between regions -35 and -10, and the promoter of the xlnII gene encoded by the pJF6 xylanase. The -35 and the -10 regions are in bold.

FIGS. 10–10C show the optimal alignment of the amino acid sequence of XYL II as encoded by pJF6 with other enzymes. The list of enzymes is as follows: 2 xylanases of *Pseudomonas fluorescens* (Psexyna, Psexynbc), pJF6 xylanase (xlnpjf6), xylanase A of *Streptomyces lividans* (Stmxlna), exogluconase of *Cellulomonas fimi* (Cficex), xylanase of *Clostridium thermocellum* (Cloxylz), xylanase of Bacillus sp. (Bacxynaa), celloxylanase of *Clostridium stercorarium* (Pclocxl), xylanase of *Caldocellum saccharolyticum* (Cdcxynab), xylanase of Thermoanaerobacter sp. (Teoendxyla), endocellulose of *Caldocellum saccharolyticum* (Cdccelb), xylanase of *Butyrivibrio fibrisolvens* (Butxynb) and a xylanase of *Rumiococcus flavefaciens* (Rumlxyna). Amino acid consensus is indicated in bold, and those amino acids retained in all examined enzymes are represented by an asterisk (*). Hypothetically retained regions are shown by an underline bracket.

FIG. 11 shows the homology among the amino acid derived sequences of xylanase A of *Streptomyces lividans* and that of XYL II as encoded by pJF6. The symbols between sequences indicate that the comparison value is the same (|), >0.5 (:), >0.1 (.). An indication of ≧0.5 means that the two different amino acids represent conservative changes (ie., there is some structural and/or functional similarity between them). An indication of ≧0.1 represents amino acids that have no or weak structural and/or functional similarity.

FIG. 12 shows the sequence of nucleotides 1538 to 1672 inclusive, of the xlnII sequence on pJF6. Arrows indicate repeated and inverted sequences.

FIG. 13 and 13A show the MAP program prediction of the proteolytic cleavage sites along the amino acid derived sequence of XYL II as encoded by pJF6 and the xylanase A of *Steptomyces lividans*. The letters represent the following proteases: S (*Staphylococcus aureus* protease), T (Trypsin) and C (Chymotrypsin). The differences encountered are shown in bold.

Deposits

Figure 1:
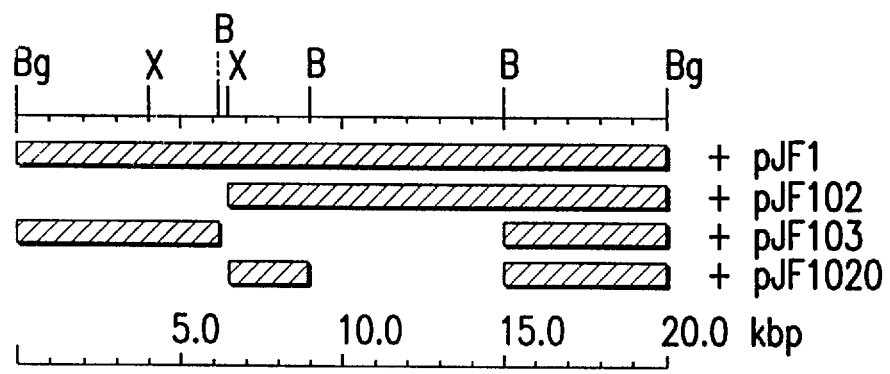
FIG. 1 shows the restriction map of the inserts cloned in plasmid pJF1. The shaded boxes shows the approximate locations of the xylanase genes after deletions of their respective inserts. Top line, restriction sites in the full-length insert. Top shaded line: pJF1 (20.0 kb; full length insert); Second shaded line: pJF102 (13.5 kb); third shaded line: pJF103 (11.5 kb); and fourth shaded line: pJF1020 (7.5 kb). Bg, BglII; B, BamHl; X, XhoI. +, xylanase positive; –, xylanase negative.

Plasmid pJF1 was deposited in *E. coli* at the American Type Culture Collection (ATCC), 12301 Parklawn Drive, Rockville, Md. 20852 on Aug. 2, 1994 and assigned accession no. 69670.

Plasmid pJF6 was deposited in *E. coli* at the ATCC on Aug. 2, 1994 and assigned accession no. 69671.

Actinomadura sp. FC7 was deposited at the ATCC on Jul. 24, 1995 and assigned accession no. 55698.

DETAILED DESCRIPTION OF THE INVENTION

I. Definitions

In the description that follows, a number of terms used in recombinant DNA technology are extensively utilized. In order to provide a clearer and consistent understanding of the specification and claims, including the scope to be given such terms, the following definitions are provided.

Xylanase. As used herein, a xylanase is a hemicellulase that cuts the β-1,4 bonds within the xylosic chain of xylan, (xylan is a polymer of D-xylose residues that are joined through β-1,4 linkages. Xylanase activity is synonymous with xylanolytic activity.

By a host that is "substantially incapable" of synthesizing one or more cellulase enzymes is meant a host in which the activity of one or more of the cellulase enzymes is depressed, deficient, or absent when compared to the wild-type.

Enzyme preparation. By "enzyme preparation" is meant a composition containing enzymes that have been extracted from (either partially or completely purified from) a microbe or the medium used to grow such microbe. "Extracted from" means any method by which the desired enzymes are separated from the cellular mass and includes breaking cells and also simply removing the culture medium from spent cells. Therefore, the term "enzyme preparation" includes compositions comprising medium previously used to culture a desired microbe(s) and any enzymes which the microbe(s) has secreted into such medium during the culture.

Biobleaching. By "biobleaching" is meant the extraction of lignin from cellulose pulp after the action of hemicellulose degrading enzymes with or without lignin degrading enzymes. Removal of the lignin may be restricted by hemicelluloses either physically (through reprecipitation onto the fiber surface during cooking) or chemically (through lignin-carbohydrate complexes). The hemicellulase activity partially degrades the hemicellulose, which enhances the extractability of lignins by conventional bleaching chemicals (like chlorine, chlorine dioxide, peroxide, etc.) (Viikari et al., "Bleaching with Enzymes" in *Biotechnology in the Pulp and Paper Industry,* Proc. 3rd Int. Conf., Stockholm, pp. 67–69 (1986); Viikari et al., "Applications of Enzymes in Bleaching" in *Proc. 4th Int. Symp. Wood and Pulping Chemistry,* Paris, Vol. 1, pp. 151–154 (1987); Kantelinen et al., "Hemicellulases and their Potential Role in Bleaching" in *International Pulp Bleaching Conference, Tappi Proceedings,* pp. 1–9 (1988)). The advantage of this improved bleachability is a lower consumption of bleaching chemicals and lower environmental loads or higher final brightness values.

By an enzyme "homologous" to a host of the invention is meant that an untransformed strain of the same species as the host species naturally produces some amount of the native protein; by a gene "homologous" to a host of the invention is meant a gene found in the genome of an untransformed strain of the same species as the host species. By an enzyme "heterologous" to a host of the invention is meant that an untransformed strain of the same species as the host species does not naturally produce some amount of the native protein; by a gene "heterologous" to a host of the invention is meant a gene not found in the genome of an untransformed strain of the same species as the host species.

Cloning vehicle. A plasmid or phage DNA or other DNA sequence (such as a linear DNA) which provides an appropriate nucleic acid environment for the transfer of a gene of interest into a host cell. The cloning vehicles of the invention may be designed to replicate autonomously in prokaryotic and eukaryotic hosts. In fungal hosts such as Trichoderma, the cloning vehicles generally do not autonomously replicate and instead, merely provide a vehicle for the transport of the gene of interest into the Trichoderma host for subsequent insertion into the Trichoderma genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are antibiotic resistance. Alternatively, such markers may be provided on a cloning vehicle which is separate from that supplying the gene of interest. The word "vector" is sometimes used for "cloning vehicle."

Expression vehicle. A vehicle or vector similar to a cloning vehicle but which is capable of expressing a gene of interest, after transformation into a desired host.

When a fungal host is used, the gene of interest is preferably provided to a fungal host as part of a cloning or expression vehicle that integrates into the fungal chromosome. Sequences which derive from the cloning vehicle or expression vehicle may also be integrated with the gene of interest during the integration process. For example, in *T. reesei,* the gene of interest can be directed to the cbh1 locus.

The gene of interest may preferably be placed under the control of (i.e., operably linked to) certain control sequences such as promoter sequences provided by the vector (which integrate with the gene of interest). If desired, such control sequences may be provided by the host's chromosome as a result of the locus of insertion.

Expression control sequences on an expression vector will vary depending on whether the vector is designed to express a certain gene in a prokaryotic or eukaryotic host (for example, a shuttle vector may provide a gene for selection in bacterial hosts) and may additionally contain transcriptional elements such as, enhancer elements, termination sequences, and/or translational initiation and termination sites.

I. Isolation of *Actinomycetes actinomadura* sp. FC7

The project had the objective of isolating a microorganism, an actinomycete under the circumstances, which would have an acidophilic and thermostable xylanolytic activity. The actinomycetes are aerobic gram-positive bacteria found mainly in the soil. The actinomycetes display a mycelial morphology interestingly resembling microscopic fungi. Furthermore, they are recognized as excellent enzyme secretors, thereby playing a very important role during biomass degradation.

A screening program was established in order to find actinomycetes that produce xylanases able to hydrolyse xylan chains in a hemicellulose liquor (a by-product of steam treatment of the lignocellulosic biomass) at moderately acid pH (4.0) and high temperature (70° C). The hunt for such an organism was made based upon places in which an important periodic heating-up could be produced, such as in hay, compost and manure.

The first step involved a selection for xylanolytic actinomycetes having optimal growth at 50°–60° C. and that demonstrated a strong degradation capability of RBB-xylan on solid medium. A series of thermostable and acidophilic actinomycetes with these characteristics were isolated from compost, manure and straw and further examined for their ability to produce xylanolytic enzymes that were relatively active at pH4, and 70° C. In this second step of the screening, the xylan hydrolysis rates at pH 5/60° C. of crude enzyme preparations secreted from the selected actinomycetes were compared to those at pH 4/70° C. for the same microbe. This was done to determine the level of acid- and thermo-resistence of the xylanase enzymes being secreted by each microbe.

The selection procedure identified one microbe from manure that was especially desirable in that it produced xylanolytic enzymes that were relatively active at pH4, and 70° C. This microbe was identified as a member of the genus Actinomadura by chemotaxonomic procedures, and was named Actinomadura sp. FC7. Pure preparations of Actinomadura sp. FC7, produced at least four xylanolytic activities as demonstrated by zymogram. The crude enzymes produced by the strain FC7 retained 65% of their activity in the more stringent of the two conditions (pH 4/70° C.).

II. Xylanase Biobleaching at High Temperature and Acidic pH

The present invention comprehends a method for chemically treating plant biomass under conditions of high temperature and low pH. In a preferred embodiment, plant biomass is bio-bleached with xylanases that are able to hydrolyze xylan chains in a hemicellulose liquor (a by-product of steam treatment of the lignocellulose biomass) at moderately acid pH (4.0) and high temperature (70° C.).

Plant biomass is a composite material consisting primarily of a matrix of cellulose, hemicellulose, and lignin. Removal of the lignin component is desirable during the manufacturer of paper because of its brown color and tendency to reduce the strength of the paper product. Many processes have been developed for the removal of lignin. Typically, the wood pulp is treated with chorine or other toxic chemicals in order to remove the lignin component and provide for a brightened pulp. However, the toxic by-products of this chemical treatment negatively impact upon the health and stability of the environment into which they are released. Consequently there is a great need for developing alternative, more environmentally protective techniques to achieve pulp bleaching.

A common treatment of plant biomass for paper production involves a thermo-mechanical steam treatment followed by extraction with hot water. This process dissociates xylan containing hemicelluloses and some lignin derivatives which are otherwise tightly bound to the cellulose. Under the method of the present invention, a biobleaching technique is developed whereby thermostable xylanases which are active at low pH may be used in vitro to modify or decrease the lignin in wood pulps. These stringent processing conditions may additionally act to reduce cellulase activity in the enzyme preparation or culture medium.

In a preferred embodiment, the process of the invention is carried out in vitro in the acidic hemicellulose liquor. The process involves placing the enzyme preparation, culture medium, or concentrated mixture containing xylanase into contact with the wood pulp. Routine calculations enable those in the art to determine the optimum treatment time depending upon the result desired, the concentration and specific activity of the xylanase enzyme used, the type and concentration of pulp used, pH and temperature of the acidic liquor, and other parameter variables.

It is preferred that the process occurs at the ambient temperature and pH of the liquor with temperatures from 45°–90° being preferred and temperatures of 70° being most preferred. It is also preferred that the pH of the liquor be less than 6.0 with a pH of 4.0 being most preferred.

The method of the present invention may be applied alone or as a supplement to other treatments that reduce the lignin content of wood pulp, increase its drainability and/or decrease its water retention. In a preferred embodiment, the present invention is used to enhance brightness properties of the wood pulp by treatment of chemical pulps, i.e., those pulps containing lignin that has been chemically modified through chemical treatment.

In a preferred embodiment, The xylanases used in the methods of the invention are preferably those of Actinomadura sp. FC7, and especially XYL I and XYL II. XYL I and XYL II can be provided by the native Actinomadura sp. FC7 host (and especially the culture medium from the growth of FC7 cells) or can be provided by a recombinant host, for example, as encoded by expression of the inserts on pJF1 and pJF6.

III. Genetic Engineering of the Hosts of the Invention

The process for genetically engineering the hosts of the invention is facilitated through the cloning of genetic sequences that encode the desired xylanase activity and through the expression of such genetic sequences. As used herein the term "genetic sequences" is intended to refer to a nucleic acid molecule (preferably DNA). Genetic sequences that encode the desired xylanase are derived from a variety of sources. These sources include Actinomadura sp. FC7 genomic DNA, cDNA, synthetic DNA and combinations thereof. Vector systems may be used to produce hosts for the production of the enzyme preparations of the invention. Such vector construction (a) may further provide a separate vector construction (b) which encodes at least one desired gene to be integrated to the genome of the host and (c) a selectable marker coupled to (a) or (b). Alternatively, a separate vector may be used for the marker.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation, (2) interfere with the ability of the expression regulatory sequences to direct the expression of the mRNA, antisense RNA, or protein, or (3) interfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively.

Expression of the protein in the transformed hosts requires the use of regulatory regions functional in such hosts. A wide variety of transcriptional and translational regulatory sequences can be employed. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

In a preferred embodiment, a desired protein is secreted into the surrounding medium due to the presence of a secretion signal sequence. If a desired protein does not possess its own signal sequence, or if such signal sequence does not function well in the host, then the protein's coding sequence may be operably linked to a signal sequence homologous or heterologous to the host. The desired coding sequence may be linked to any signal sequence which will allow secretion of the protein from the host. Such signal sequences may be designed with or without specific protease sites such that the signal peptide sequence is amenable to subsequent removal. Alternatively, a host that leaks the protein into the medium may be used, for example a host with a mutation in its membrane.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells.

The vectors of the invention may further comprise other operably linked regulatory elements such as enhancer sequences.

In a preferred embodiment, genetically stable transformants are constructed whereby a desired protein's DNA is integrated into the host chromosome. The coding sequence for the desired protein may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

Cells that have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transformation.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct (s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

Accordingly, the XYL I and XYL II encoding sequences may be operably linked to any desired vector and transformed into a selected host, so as to provide for expression of such proteins in that host.

IV. The Enzyme Preparations of the Invention

According to the invention, there is provided enzyme compositions useful in a method for biobleaching and pulp and paper processing. There is also provided a method for producing an enzyme preparation partially or completely deficient in cellulolytic activity (that is, in the ability to completely degrade cellulose to glucose) and enriched in xylanases desirable for pulp and paper processing. By "deficient in cellulolytic activity" is meant a reduced, lowered, depressed, or repressed capacity to degrade cellulose to glucose. Such cellulolytic activity deficient preparations, and the making of same by recombinant DNA methods, are described in U.S. Pat. No. 5,298,405, incorporated herein by reference. As described herein, xylanases may be provided directly by the hosts of the invention (the hosts themselves are placed in the wood processing medium). Alternatively, used medium from the growth of the hosts, or purified enzymes therefrom, can be used. Further, if desired activities are present in more than one recombinant host, such preparations may be isolated from the appropriate hosts and combined prior to use in the method of the invention.

The enzyme preparations of the invention satisfy the requirements of specific needs in various applications in the pulp and paper industry. For example, if the intended application is improvement of the strength of the mechanical mass of the pulp, then the enzyme preparations of the invention may provide enzymes that enhance or facilitate the ability of cellulose fibers to bind together. In a similar manner, in the application of pulp milling, the enzyme preparations of the invention may provide enzymes that enhance or facilitate such swelling.

To obtain the enzyme preparations of the invention, the native or recombinant hosts described above having the desired properties (that is, hosts capable of expressing large quantities of the desired xylanase enzymes and optionally, those which are substantially incapable of expressing one or more cellulase enzymes) are cultivated under suitable conditions, the desired enzymes are secreted from the hosts into the culture medium, and the enzyme preparation is recovered from said culture medium by methods known in the art.

The enzyme preparation can be produced by cultivating the recombinant host or native strain in a fermentor. For example, the enzyme preparation of the present invention can be produced in a liquid cultivation medium that contains oat spelt xylans as the main carbon source as described by Morosoli et al., *Biochem J.* 239:587–592 (1986)).

The enzyme preparation is the culture medium with or without the native or transformed host cells, or is recovered from the same by the application of methods well known in the art. However, because the xylanase enzymes are secreted into the culture media and display activity in the ambient conditions of the hemicellulose liquor, it is an advantage of the invention that the enzyme preparations of the invention may be utilized directly from the culture medium with no further purification. If desired, such preparations may be lyophilized or the enzymatic activity otherwise concentrated and/or stabilized for storage. The enzyme preparations of the invention are very economical to provide and use because (1) the enzymes may be used in a crude form; isolation of a specific enzyme from the culture fluid is unnecessary and (2) because the enzymes are secreted into the culture medium, only the culture medium need be recovered to obtain the desired enzyme preparation; there is no need to extract an enzyme from the hosts.

If desired, an expressed protein may be further purified in accordance with conventional conditions, such as extraction, precipitation, chromatography, affinity chromatography, electrophoresis, or the like.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLE I

Materials and Methods

Bacterial strains and vector

The *Escherichia coli* strain DH5α (F⁻ φ80dlacZΔM15 Δ(lacZYA-argF) U169 deoR recA1 endA1 hsdR17 supE44 λ⁻ thi-1 gyrA96 relA1; Gibco BRL), was used in routine manipulations. The periplasmic-leaky strain *E. coli* 4924 N/14 (de Zwaig et al., *J. Bacteriol.* 94:1112–1123 (1967)) was used for the cloning and detection of xylanase genes. *Streptomyces lividans* strain 1326 was kindly provided by D. A. Hopwood (John Innes Institute, Norwich, U.K.). *S. lividans* strain 10-164, a mutant of *S. lividans* 1326 negative for xylanase and cellulase activities (Mondou, F. et al., *Gene* 49:323–329 (1986)), was kindly provided by D. Kluepfel (Centre de Recherche en Microbiologie Appliquée, Laval (Québec), Canada). All the others strains used were wild-type isolates from various natural materials. The shuttle *E. coli*-Streptomyces vector pFD666 was described previously (Denis & Brzezinski, *Gene* 111:115–118 (1992)).

Growth of bacterial strains

*E. coli* strains were grown in Luria Bertani (LB) medium (Sambrook, J. et al., *Molecular cloning*, a laboratory manual (2nd edition), Cold Spring Harbor Laboratory Press, Cold Spring Harbor, N.Y. (1989)).

Actinomycete strains were routinely propagated on Tryptic Soy Broth (Difco). The media for *S. lividans* protoplast preparation and regeneration were as described by Hopwood et al. (*Genetic manipulation of Streptomyces*, The John Innes Foundation, Norwich (1985)). Long-term storage and handling was as described previously (Fink, D. et al., *Biotech. Lett.* 13:845–850 (1991)).

Chemotaxonomical procedures

The diaminopimelic acid form in the cell wall and the predominant sugars in whole-cell hydrolysates were analyzed by thin-layer chromatography according to Staneck & Roberts (*Appl. Microbiol.* 28:226–231 (1974)). The G+C content of total DNA was estimated by the method of Ulitzur (*Biochim. Biophys. Acta* 272:1–11 (1972)). Fatty acids were analyzed by the procedure of Sasser (Sasser, M., in *Methods in Phytobacteriology*, Klement & Sands, eds., Akademiai Kiado, Budapest (1990), pp. 199–204).

Biochemical assays

Xylanase activity was assayed using the Nelson-Somogyi method (Spiro, R. G., *Meth. Enzymol.* 8:3–26 (1966)) which measures the release of reducing sugar from 0.5% (w/v) soluble oat spelts xylan in citrate-phosphate-borate buffer (Teorell buffer). In standard conditions, the pH was 5.0 and incubation was for 10 min. at 60° C. The reaction was terminated by the addition of the first reagent of the reducing sugar assay. One unit of enzyme activity was defined as the amount of enzyme releasing 1 μmole of D-xylose equivalent per minute in standard assay conditions.

The β-xylosidase activity was measured with 2 mM p-nitrophenyl-β-D-xyloside as substrate. Incubation was for 10 min. at 60° C. in Teorell buffer pH 5.0. The release of p-nitrophenol was monitored at 410 nm.

Total protein was measured by the method of Bradford, M. M. *Anal. Biochem.* 72:248–254 (1976) using the alkaline reagent described by Stoscheck (Stoscheck, C. M., *Anal. Biochem.* 184:111–116 (1990)). The molecular weights of the purified enzymes were estimated by SDS-PAGE (Laemmli, U.K. *Nature* 227:680–685 (1970)). Coloration for glycoproteins with the Schiff reagent was as described in Glossman & Neville (1971). Thin-layer chromatography of hydrolysis products was performed as described by Biely, P. et al., *Biochim. Biophys. Acta* 1162:246–254 (1993).

The procedure of Bertheau, Y. et al., *Anal. Biochem.* 139:383–389 (1984) was used to analyze crude or purified xylanases by electrofocusing in an ultrathin polyacrylamide gel (pH gradient 5 to 8). Ten μl of 20 times concentrated supernatant were applied. Standard proteins (Bio-Rad) were applied on these gels alongside the culture filtrates to estimate the pI of xylanases. An agarose-RBB xylan overlay was used to detect xylanase activities. The overlay gel was prepared from a mixture of 0.8% agarose and 0.2% RBB-xylan. The agarose-RBB xylan gel was overlaid onto the electrofocusing gel. Incubation was carried out at 50° C. for 1 hr. Clear zones in the overlay gel indicated xylanase activity.

In liquid culture, xylanase-positive actinomycetes were inoculated into Tryptic Soy Broth and cultivated with shaking at 50° C. Once an appropriate cell density was reached, the mycelium was recovered by centrifugation and inoculated into xylanase production medium (Morosoli, R. et al., Biochem. J. 239:587–592 (1986)) containing oat spelts xylan as the main carbon source. Xylanase activity was measured daily using a standard assay (measuring the release of reducing sugars from oat spelts xylan incubated with culture supernatants samples for 10 min. at 60° C., pH 5.0).

Bacterial, bacteriophage and plasmid preparations

The bacteriophage M13K07 (Vieira and Messing, *Methods Enzymol.* 153: 3–11 (1987)) was used in the production of single strand DNA. The vectors pFD666 (Denis and Brzezinski, *Gene* 11: 115–118 (1992)), pUC118, pUC119 (Vieira and Messing, *Methods Enzymol.* 153: 3–11 (1987)), and pUC21 (Vieira and Messing, *Gene* 100: 189–194 (1991)) were used for cloning and sequencing purposes.

Culture media

LB medium was used during the preparation of competent cells and their transformation (Sambrook et al., *Molecular cloning. A laboratory manual*, Second edition. Cold Spring Harbor Laboratory Press. New York. (1989)). LB-RBB-xylan (LB+0.2% RBB-xylan+1.5% agar) was used to detect xylanolytic clones. RBB-xylan is a complex deriving from the joining of a coloring agent, Remazol Brilliant Blue (RBB) to xylan. This was synthesized by following the protocol published by Biely et al. *Anal. Biochem.* 144: 142–146 (1985)).

The medium M13 was used for the production of xylanase (Morosoli et al., *Biochem. J.* 239: 587–592(1986)). The composition of the medium is as follows: 10 g xylan, 1.4 g $(NH_4)_2SO_4$, 2.5 g $K_2HPO_4$, 1.0 g $KH_2PO_4$, 2.0 g of extract of yeast, 1.0 g peptone, 0.3 g $MgSO_4.7H_2O$ per liter of water. The pH is adjusted to 7.0 after sterilization, then 1.0 ml of a solution of micro-elements is added (0.2 g $CoCl_2.7H_2O$, 0.5 g $FeSO_4.7H_2O$, 0.16 g $MnSO_4.H_2O$, 0.14 g$ZnSO_4.H_2O$, in 100 ml of distilled water with the pH adjusted to 3 with HCl). Olive oil (2 ml/liter) was added to increase the enzyme secretion (Bertrand et al., *Biotechnol. Bioeng.* 33: 791–794 (1989)).

The minimal RBB-xylan medium was used to detect xylanolytic activity. The method was adapted in accordance with Kluepfel's protocol (*Methods Enzymol.* 160:180–186 (1988)). Part A is autoclaved separately, containing 0.5 g $K_2HPO_4$, 0.2 g $MgSO_4.7H_2O$, 1.0 g $(NH_4)_2SO_4$, 15 g agar in a volume adjusted to 700 ml of water, then part B containing 2 g RBB-xylan in 300 ml of water is autoclaved. After cooling and mixing parts A and B, 1 ml of the micro-element solution is added.

R2YE medium was used for the transformation and regeneration of the *S. lividans* 10-164 protoplasts (Hopwood et al., *Genetic manipulation of Streptomyces, a laboratory manual*, the John Innes Foundation, Norwich, 1985, 338 pages). TB medium was used for the for the amplification of *E. coli* (Sambrook et al., , *Molecular cloning. A laboratory manual*, Second edition. Cold Spring Harbor Laboratory Press, New York, (1989)). TSB medium was used for the growth of *S. lividans* 10-164 and Actinomadura sp. FC7 preparations. 2xYT medium was used for the production of single strand DNA with the *E. coli* TG1 preparation. This medium is composed of 16 g tryptone, 10 g extract of yeast and 5 g of NaCl for a final volume of 1 liter at pH 4.

Restriction endonuclease, ligase and phosphatase

Restriction endonucleases and ligases were purchased from Boehringer Mannheim and from Pharmacia. Calf Intestine Phosphatase (CIP) comes from Pharmacia. These enzymes were used in accordance with the manufacturer's instructions.

Preparation of cells, protoplasts, and their transformation

*E. coli* DH5αF', TG1 and 4924 N/14 competent cells were prepared and transformed in accordance with a protocol from the Imperial Cancer Research Foundation, and described by Desmarais, D., Mémoire de maîtrise. Département de biologie. Faculté des sciences. Université de Sherbrooke. 75 p. (1990). Briefly, the following procedure was used.

A) Preparation of competent cells

1. Starting with the frozen cells of the *E. coli* DH5α preparation preserved in 20% glycerol, smear the Petri dish with SOB or LB (Maniatis et al., *Molecular cloning: a laboratory manual*, Cold Spring Harbor Laboratory, N.Y., 1982, 545 pages (1982)) and incubate overnight at 37° C.
2. Inoculate 5 ml of SOB culture using a single colony.
3. Incubate the culture at 37° C. under agitation for about 2 hours, or to the point of $A_{550}$ is about 0.3 or till it begins to become cloudy.
4. Make a 1:20 dilution of the culture in 100 ml of SOB (preincubated to 37° C.) and incubate at 37° C. to the point of $A_{550}$ is 0.48 (about 2 hours). This optical density is optimal for DH5α and may be slightly different for other preparations.
5. Leave on ice for 5 minutes.
6. Centrifuge for 15 minutes to pellet cells.
7. Remove the floating matter and once again suspend the cells in 40 ml of TFB I (defined below).
8. Leave on ice for 5 minutes.
9. Centrifuge per item number 6.
10. Remove the floating matter and once again suspend the cells in 4 ml of TFB I.
11. Leave on ice for 15 minutes.
12. Distribute 200 μl via 1.5 microfuge tube (refrigerating the microfuge tubes, pipette tips and pipettes to 4° C. is preferred.
13. Freeze in dry ice.
14. Maintain the aliquotes at between −60° or −70° C.

B. Transformation

1. Defrost the cells to room temperature just enough to liquefy the suspension.
2. Leave for 10 minutes in ice.
3. Add DNA (up to ⅕ volume of the cells; use no more than 100 ng of DNA for 200 μl of cells). Using freshly prepared cells, begin the protocol at this stage.
4. Leave on ice for 30 minutes.
5. Incubate the cells at 42° C. for 90 seconds. This stage may be optimized in accordance with the preparation.
6. Put it on ice for 1–2 minutes.
7. Add 4 volumes of SOB or LB (800 μl per 200 μl of cells).
8. Incubate at 37° C. for 1 hour (agitation is preferred but unnecessary).
9. Centrifuge for 1–2 minutes in a microcentrifuge and resuspend the residue in 200 μl of SOB or LB.
10. Spread on a SOB or LB Petri dish with antibiotic.

N.B.—All centrifugings and solutions must be carried out and conserved at 4° C. respectively. It is preferable to delicately handle the cells during the stages of resuspension.

TFB I contains 30 mM potassium acetate, 100 mM RbCl$_2$, 10 mM CaCl$_2$.2CH$_2$O, 50 mM MnCl$_2$.4H$_2$O, and 15% glycerol. Adjust the pH to 5.8 using 0.2M of acetic acid. Use a 1/100 acid dilution of glacial acetic acid: this corresponds to about 50 drops for 200 ml of solution. Use of distilled water is preferred in a glass system. Sterilize through filtration.

TFB II contains 10 mM MOPS, 75 mM CaCl$_2$.2H$_2$O, 10 mM RbCl$_2$, and 15% glycerol. Adjust the pH to 6.5 with 1M KOH (about 35 drops). Sterilize through filtration.

The *S. lividans* 10-164 protoplasts were prepared and transformed according to the protocol of Hopwood et al. *Genetic manipulation of Streptomyces, a laboratory manual,* the John Innes Foundation, Norwich, 1985, 338 pages.

Purification of a DNA fragment on agar gel

Following DNA band migration on TAE agar gel (Maniatis et al., *Molecular cloning: a laboratory manual,* Cold Spring Harbor Laboratory, N.Y., 1982, 545 pages), the purification of DNA fragments was performed by the method suggested by "Gene Clean" Bio/Can Scientific, Inc.

Zymogram

The procedure is the same as for a polyacrylamide gel (SDS-PAGE) except that the sample has not been boiled, and, further, 2% RBB-xylan is added into the acrylamide mixture. The protein sample is prepared with the following (3X) swab: 3.0 ml of glycerol, 0.6 g of SDS, 0.228 g of Tris-Base, and 0.1 mg of bromphenol blue.

The development of the xylanolytic activity is achieved by soaking the gel in 100 ml of Tris-HCl 50 mM (pH 7.5)—methanol 20% at room temperature for 60 minutes. Then the gel is washed in 500 ml of Tris-HCl 50 mM (pH 7.5)—EDTA (1 mM) at 4° C. overnight. The visualization of enzymatic activity is achieved by incubating the gel at 50° C. in a McIlvaine buffer (pH6) until the bands appear.

Extraction of genomic and plasmid DNA

The plasmid DNA extraction protocol used was the one described by Maniatis et al., *Molecular cloning: a laboratory manual,* Cold Spring Harbor Laboratory. N.Y., 1982, 545 pages.

The genomic DNA extraction protocol used to extract Actinomadura sp. FC7 DNA was that of Rao et al. *Methods enzymol.* 153: 166–198 (1987)), except that the mycelium of the Actinomadura sp. FC7 (20 ml) was broken by passing French's press at a pressure of 2,000 lb/po$^2$.

EXAMPLE 2

Screening Program for the Isolation of *Xylanolytic actinomycetes*

In order to find new variants of xylanases, efficient at pH 4 and 70° C., a screening procedure was developed to identify organisms showing such activities. The screening was oriented towards actinomycetes as they are efficient producers of many extracellular enzymes and are amenable to genetic and molecular analysis.

Samples of compost, manure, straw as well as samples of biofilm developed on the inside surfaces of pipelines used by the paper industry were enriched for thermophilic actinomycetes by several treatments: dry heat treatment (120° C.; 60 min.) (Nonomura & Hayakawa, in *Biology of actinomycetes '88*, Okami, Y. et al., eds., Japan Scientific Societies Press, Tokyo (1988), pp. 288–293); selection with phenol (30 min. treatment in 1.5% w/v phenol solution, pH 6.0 at 30° C.) followed by centrifugation and washing with water (Nonomura & Hayakawa, in *Biology of actinomycetes '88*, Okami, Y. et al., eds., Japan Scientific Societies Press, Tokyo (1988), pp. 288–293); selection on humic acid-vitamin agar (Hayakawa & Nonomura, *J. Ferment. Tech.* 65:501–509 (1987)) or cultivation on semidry xylan powder, as described by Waldron et al. (*Appl. Microbio. Biotech.* 24:477–486 (1986)) except that xylan was substituted for cellulose.

If desired, novobiocin (50 mg/l) may be used to eliminate mobile bacteria in the first selection of actinomycete colonies. Some thermophilic actinomycete strains may be killed when novobiocin is used in this manner. However, the strain of the invention, Actinomadura sp. FC7 seems to be relatively resistant to novobiocin.

After these treatments, surviving bacteria were plated on Tryptic Soy Agar and cultivated at 50° C. or 60° C. Individual colonies were picked and inoculated on minimal agar containing 0.2% xylan covalently bound to Remazol Brilliant Blue (RBB-xylan; Biely, P. et al., *Anal. Biochem.* 144:142–146 (1985)) and incubated at 50° C. or 60° C. Each day, the colonies were examined for medium clearing and morphology. *Xylanolytic actinomycetes* were retained for further studies.

A total of 12 strains growing at temperatures between 50° and 60° C. and showing marked degradation capability of RBB-xylan on solid medium were isolated from compost, manure or straw (Table 1). All these strains were classified in the actinomycete group on the basis of their morphology and the high (>65 mol %) G+C content in their total DNA.

All the strains were examined for their ability to produce xylanolytic enzymes that were relatively active at pH 4, 70° C. For this purpose, all the strains were cultivated in tryptic soy broth at 50° C. (except the control strain, *S. lividans* 1326 which was grown at 30° C.), then inoculated in xylanase production medium. Extracellular xylanase activity was measured by the release of reducing sugars from xylan in two different conditions: at 60° C., pH 5.0 (the xylanase activity measured in these conditions was taken as 100%), and at 70° C., pH 4.0 (stringent conditions) (Table 1). Six strains (as well as *S. lividans* 1326) kept 5% or less of their activity in the stringent conditions; three strains retained between 5% and 20% and three strains retained more than 40%. The strain FC7 (originating from manure and isolated on humic acid-vitamin agar) retained 65% of its activity at 70° C. pH 4. This strain was chosen for further studies since its crude xylanase was also efficient at hydrolyzing the xylan contained in the hemicellulose liquor.

TABLE 1

Summary of the isolation of xylanolytic thermophilic actinomycetes

| Isolate | Origin | Enrichment method | Xylanolytic activity kept at pH 4/70° C.[1] |
|---|---|---|---|
| F1 | manure | dry heat[2] | 14% |
| F2 | manure | dry heat + phenol[3] | 2% |
| FAA3 | manure | solid enrichment[4] | 12% |
| FC7 | manure | HV-agar[5] | 65% |
| FP604 | manure | phenol | 3% |
| FP605 | manure | phenol | 2% |
| PA1 | straw | solid enrichment | 5% |
| CA1 | compost | solid enrichment | 57% |
| CCA3 | compost | solid enrichment | 50% |
| CCA5 | compost | solid enrichment | 20% |
| CCA601 | compost | solid enrichment | 2% |
| C604 | compost | — | 2% |
| *S. lividans* 1326 | control strain | | 2% |

[1]Activity at pH 5/60° C. was taken as 100%.
[2]Dry heat treatment (120° C., 60 min.) (Nonomura & Hayakawa, in Biology of actinomycetes '88, Okami, Y. et al., eds., Japan Scientific Societies Press, Tokyo (1988), pp. 288–293).
[3]Treatment in 1.5% phenol (30° C., 30 min.) (Nonomura & Hayakawa, op. cit.).
[4]Modified after Waldron Jr., C. R. et al., Appl. Microbio. Biotech. 24:477–486 (1986).
[5]Humic-acid - vitamin agar selection (Hayakawa & Nonomura, J. Ferment. Tech. 65:501–509 (1987)).

The FC7 strain demonstrated a typical actinomycete morphology with white-yellow basal mycelium when grown on tryptic soy agar. In liquid cultures in Tryptic Soy Broth medium, the growth of FC7 (estimated as wet weight of mycelium per ml of culture broth) was maximal at 37°–50° C., moderate at 30° C. and 60° C. and very slow at 22° C. Sporulation was observed only once: the FC7 was monosporic, with spores produced on very short sporophores in a poorly developed aerial mycelium. mesodiaminopimelic acid was found in the cell wall peptidoglycan. No mycolic acids were found. Whole-cell sugars had no diagnostic value as they varied widely with the temperature at which the organism was cultivated. The relative abundance of hexadecanoic (26.45% of total fatty acids content), 14-methylpentadecanoic (11.28%) and 10-methyloctadecanoic (10.75%) acids in the fatty acid composition (pattern "3a" according to Kroppenstedt, R. M., in *Chemical methods in bacterial systematics,* Goodfellow & Minnekin, eds., Academic Press, London (1985), pp. 173–199), in conjunction with the other taxonomic data, permitted the classification of FC7 in the "*Actinomadura-Thermomonospora curvata*" group of the family Thermomonosporaceae (Kroppenstedt & Goodfellow, in *The Prokaryotes,* Balows et al., eds., Springer-Verlag, New York (1992), pp.1085–1114). The strain will thus be referred to as Actinomadura sp. FC7. No attempts were made to classify this strain at the species level. This bacteria synthesizes xylanases which maintain most of their xylanolytic activity at a temperature of 70° C. and at pH 4. By means of a zymogram it was determined that this preparation would produce up to 4 xylanases.

EXAMPLE 3

Cloning of *Actino madura* sp. FC7 Xylanase Genes into *E. coli* DH5α

Preparations of *Escherichia coli* DH5αF' (Bethesda Research Laboratory) were used for cloning manipulations. For gene bank construction, total DNA was isolated from Actinomadura sp. FC7 by the method of Rao, R. N. et al., *Meth. Enzymol.* 153:166–198 (1987). Genomic DNA of the Actinomadura sp. FC7 preparation was completely digested with the restriction endonuclease BGlII. The genome of the Actinomadura sp. FC7 preparation, following a complete digestion by BglII, generated fragments with an average size of 12 kb.

The BGlII fragments were spliced into the pFD666 vector that had first been cut with BamHI and dephosphorylated in accordance with the protocol proposed by Maniatis, T., et al. (In: *Molecular Cloning, A Laboratory Manual,* Cold Spring Harbor Laboratories, Cold Spring Harbor, N.Y. (1982)). *E. coli* DH5αF' (200 μl of qualified cells) was transformed with 100 ng of binding mixture. The cells were spread out on solid LB-RBB-xylan plus kanamycin (50 μg/ml) then incubated at 37° C. for 5 to 6 days.

The effectiveness of resultant recombination was 86% (about 9,000 recombinants out of 10,500 examined). The number of recombinant preparations was assessed in accordance with the mini-preparation method Maniatis, T., et al. (In: *Molecular Cloning, A Laboratory Manual,* Cold Spring Harbor Laboratories, Cold Spring Harbor, N.Y. (1982)). The gene bank represented more than 99% of the genome of Actinomadura sp. FC7. This percentage was derived from the formula described by Clarke and Carbon, *Cell* 9: 91 (1976).

Six potentially positive xylanolytic clones were obtained after 5 to 6 days of incubation following the appearance of degradation zones. Following a respreading on LB-RBB-xylan medium, five positive clones, or pJF1, pJF3, pJF6, pJF8 and pJF10 were identified and selected, while the other clones (pJF2, pJF4, pJF5, pJF7 and pJF9) were eliminated as false-positives. Restriction endonuclease analysis confirmed that clones pJF1 and pJF3 had an insert of an approximate size of 20 kb, while clones pJF6 and pJF8 would have the same 2.7 kb insert, but in an opposite orientation. Clone pJF10 had multiple BglII inserts, of which one 2.7 kb insert was identical to the one found in pJF6 and pJF8.

*E. coli* is a Gram-negative bacteria, and it is not known to be effective for the secretion of enzymes. Nonetheless, positive clones were isolated thanks to the natural lysis of bacteria. In other words, as a result of the release of the contents of the *E. coli* host into the medium containing RBB-xylan; since the recombinant host expressed the xylanase gene, it produces a degradation zone around it, occurring after 5 to 6 days of incubation.

EXAMPLE 4

Cloning of Actinomadura sp. FC7 Xylanase Genes into *E. coli* 4924 N/14

The plasmids from the gene bank described in example 3 were isolated by a total plasmid preparation as proposed by Maniatis, T., et al. (In: *Molecular Cloning, A Laboratory Manual,* Cold Spring Harbor Laboratories, Cold Spring Harbor, N.Y. (1982)) and transformed into *E. coli* 4924 N/14. After ligation, the DNA mixture was used to transform competent cells of a periplasmic-leaky strain *E. coli* 4924. The transformation mixture was plated on LB agar containing 50 μg/ml of kanamycin and 0.2 mg/ml of RBB-xylan. A total of 8850 recombinants was obtained. After 2–3 days of incubation at 37° C., colonies surrounded by clear areas were picked, grown in LB liquid medium and replated at low density on RBB-xylan medium. Six of these recombinants showed clearing of RBB-xylan after 2 days of incubation.

In order to speed up the operations involving the visualization of degradation zones, we used the *E. coli* 4924 N/14 preparation. *E. coli* 4924 N/14 has a periplasmic deficiency which has not been genetically defined (de Zwaig and Luria, *J. Bacteriol.* 94: 1112–1123 (1967)). So this allows the very swift passage of its periplasmic contents to the external medium. The main reasons for its use are a better visualization of degradation, and an economy of time. Clone pJF11, for example, was isolated thanks to this preparation, because the sensitivty of the method with *E. coli* 4924 N/14 was probably stronger than with *E. coli* DH5α. The appearance of a degradation zone needs only 16 hours instead of 120.

The ability to hydrolyze RBB-xylan was conserved after plasmid purification from all of these recombinants and retransformation into a new host. Since xylanolytic activities were detected in recombinant *E. coli* strains and since *E. coli* is not known to produce xylanolytic activities, the cloned genes should encode xylanases and not a regulatory protein involved in xylanase production.

The clones that appeared to be able to hydrolyze RBB-xylan after this second round of plating were retained for further studies. Their plasmid DNAs were extracted and mapped with restriction enzymes using standard methods (Sambrook, J. et al., *Molecular cloning, a laboratory manual* (2nd edition), Cold Spring Harbor Laboratory Press, Cold Spring Harbor, N.Y. (1989)).

Figure 2:
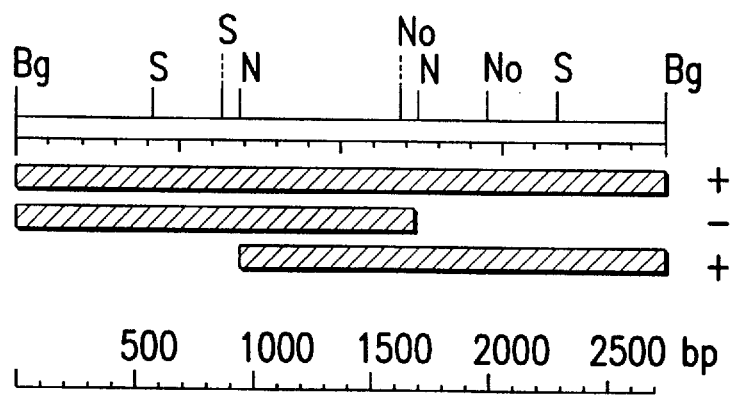
FIG. 2 shows the restriction map of the inserts cloned in plasmid pJF6. The shaded boxes shows the approximate locations of the xylanase genes after deletion of the respective insert. Bg, BglII; N, NruI; No, NotI, S, SalI. +, xylanase positive; –, xylanase negative. Top shaded line: pJF6; second shaded line: pJF61; third shaded line: pJF62.

Plasmids pJF1, pJF3, pJF6, pJF8 and pJF10 were analyzed by restriction mapping. pJF1 and pJF3 carried the same cloned insert (about 20 kb) but in opposite orientations. The other three plasmids also had a common cloned segment (2.7 kb), either in two opposite orientations (pJF6 and pJF8) or fused to another segment (pJF10). This segment was different from the insert present in pJF1 and pJF3. Thus, the transformants fell into two distinct groups. One transformant from each group (pJF1 and pJF6) was chosen for further studies. The xylanase-encoding segments were mapped by deletion subcloning, transformation and plating on RBB-xylan agar. The shortest DNA segments still allowing for xylanase expression are shown on FIGS. 1 and 2. The differences between the restrictions maps suggested that two different xylanase genes were cloned: xlnI carried by pJF1 (FIG. 1) and xlnII carried by pJF6 (FIG. 2). The corresponding xylanases were named Xyl I and Xyl II, respectively. Clone pJF6 was chosen for sequencing as it presents the interesting characteristic of having a relatively short insert (2.7 kb), and required no extensive shortening of its insert by sub-cloning.

The BamHI site of pFD666, used for insertion of the xylanase genes, is localized inside of a multiple cloning site flanked by transcriptional terminators. However, it has been shown that some transcription occurs from one side, most likely driven by the neomycin resistance gene (Denis, F., "Construction d'un vecteur navette pour *Escherichia coli* et les actinomycètes et clonage d'un gène de chitosanase d'actinomycète," Ph.D. thesis, Université de Sherbrooke (1994), 120 pp.). Since the xylanase genes were cloned in both orientations in the BamHI site and xylanolytic were detected in *E. coli* recombinant strains, whatever their orientations, it seems likely that some Actinomadura promoters can be recognized in *E. coli*.

Zymogram analysis revealed that 2 xylanases are produced by the clone pJF1. These pJF1 xylanases would correspond to the the two highest molecular weight bands produced by Actinomadura sp. FC7. Zymogram analysis of Actinomadura sp. FC7 culture supernatants in xylan medium revealed two major (slower) and two minor (faster) bands of activity (not shown). The two major (slower) bands co-migrated with the two bands obtained with the crude preparation from 10-164(pJF1) culture supernatant and corresponded most probably to the 48 kDa and 37 kDa forms of Xyl I (see below). The activity of Xyl II could not be visualized with this particular zymogram system, probably because of the inability of this protein to renature during the post-incubation steps. Thus, besides Xyl I and Xyl II, FC7 produces at least one or two other xylan-degrading activities. The occurrence of multiple xylanase activities have been reported in numerous microorganisms (Wong, K. K. Y. et al., *Microbiol. Rev.* 52:305–317 (1988)).

The pJF1 clone insert was reduced, yielding the sub-clone pJF1020. The latter has an insert of about 7.5 kb, which is sufficient to contain within it 2 genes coding for xylanases. The gene(s) is located in a 5 kb portion of the inital fragment.

EXAMPLE 5

Xylanase Production by Recombinant Strains

The plasmids isolated from the *E. coli* clones that were able to hydrolyze RBB-xylan were used to transform protoplasts of *S. lividans* 10-164. After protoplast regeneration and colony selection for kanamycin resistance, the transformants were tested for their xylanase-positive phenotype on minimal medium (Hopwood, D. A. et al., *Genetic manipulation of Streptomyces,* The John Innes Foundation, Norwich (1985)) containing RBB-xylan.

Plasmids pJF1 and pJF6 were used to transform *S. lividans,* as *E. coli* is not an efficient host for extracellular enzyme production. The mutant strain *S. lividans* 10-164 was used because of its inability to produce endogenous xylanase and cellulase activities (Mondou, F. et al., *Gene* 49:323–329 (1986)). Both plasmids complemented the xylanase-negative phenotype when transferred into the 10-164 strain. This host allowed over-production of the xylanases encoded by the cloned genes with a low background of other proteins, thus facilitating the purification procedure.

One transformant of each type bearing the pJF1 and pJF6 plasmids were tested for xylanase production in liquid culture. Each transformant was inoculated into Tryptic Soy Broth (Difco) containing 50 $\mu$g/ml of kanamycin and cultivated for 48–72 hours at 30° C. on a rotary shaker at 250 rev./min. The mycelium was recovered by centrifugation of the cultures in a benchtop centrifuge (3,000 g; 15 min), suspended in 50 ml of 0.9% sterile saline and centrifuged again. 24 ml of mycelial pellet were then inoculated into 1.2 liters of xylanase production medium (Morosoli, R. et al., *Biochem. J.* 239:587–592 (1986)) without kanamycin (the vector pFD666 and its derivatives are generally stably maintained in *Streptomyces lividans* without antibiotic selection (Denis & Brzezinski, *Gene* 111:115–118 (1992)). After 72 hours of cultivation, the culture was centrifuged (11,000 g, 30 min, 4° C.) and the supernatant was recovered as the crude enzyme preparation.

EXAMPLE 6

Purification of Xylanases I and II

All the purification steps were carried out at 4° C. The chilled supernatant (0.6 liter) of a culture of *S. lividans* 10-164 (pJF1) (for xylanase I purification) or *S. lividans* 10-164 (pJF6) (for xylanase II purification) was mixed with three volumes of ice-cold 95% ethanol. After settling overnight, the precipitate was recovered by centrifugation (9,000 g, 30 min). The pellet was resuspended in 50 ml of 20 mM Tris-HCl buffer pH 8.0 and loaded on a 0.9 cm×30 cm DEAE-BioGel A anion-exchange column (Bio-Rad) equilibrated with the same buffer. The column was then washed with 50 ml of the same buffer and proteins were eluted with a linear gradient (0 to 0.6M) of KCl (total volume: 120 ml). Fractions were collected and the xylanase activity was detected by spotting 20 $\mu$l samples on RBB-xylan agar and incubating at 37° C. The active fractions were pooled, concentrated down to 4 ml by dialysis against Concentrator Resin (Bio-Rad) and loaded on a 1.6 cm×100 cm BioGel A-0.5 m size-exclusion chromatography column (Bio-Rad) equilibrated with 20 mM K-phosphate buffer pH 6.0 (prepared by mixing appropriate proportions of 100 mM monobasic potassium phosphate and 100 mM dibasic potassium phosphate, then diluting with four volumes of distilled water). Fractions were collected and xylanase activity was detected as before. After addition of glycerol (final concentration 50% v/v), enzymes were stored at −20° C.

Both xylanases were purified to homogeneity (as judged from Coomassie Blue-stained SDS-PAGE gels) by the above protocol involving ethanol precipitation, anion-exchange chromatography and size-exclusion chromatography. Table 2 summarizes the enzyme purification data. Yields of 27 and 14% were obtained and the specific activities in standard assay with oat spelts xylan were 178 and 1268 Units/mg for purified Xyl I and Xyl II, respectively.

During the purification of Xyl I, two peaks of xylanase activity were separated by the size-exclusion chromatography step. The major peak corresponded to a protein of 48 kDa (and this protein was more extensively studied) while the minor peak corresponded to a 37 kDa protein. When various deletion derivatives of pJF1 plasmid were analyzed for the pattern of their protein production, the disappearance of the minor band was always correlated with the disappearance of the major band. We conclude that the smaller protein is not encoded by a separate gene but is a derivative of the 48 kDa Xyl I protein.

The biochemical properties of Xyl I and Xyl II are summarized in Table 3. Xyl I resembles other high molecular mass/low pI xylanases (Wong, K. K. Y. et al., *Microbiol. Rev.* 52:305–317 (1988)), such as XlnA from *S. lividans* (Morosoli, R. et al., *Biochem. J.* 239:587–592 (1986); Shareck, F. et al., *Gene* 107:75–82 (1991)), or XynA from "Caldocellum saccharolyticum" (Lüthi, E. et al., *Appl. Environ. Microbiol.* 56:2677–2683 (1990); Lüthi, E. et al., *Appl. Environ. Microbiol.* 56:1017–1024 (1990): its molecular mass is higher than 40,000; it shows a low but significant aryl-β-D-xylosidase activity and it is able to hydrolyze efficiently xylooligosaccharides, as shown by the appearance of short oligomers (xylobiose, xylotriose) among the reaction products early in the hydrolysis (Table 3). In contrast, Xyl II has no detectable aryl-β-D-xylosidase activity and hydrolyzes xylooligosacharides much slower than Xyl I. In this situation, short oligomers appear in the reaction mixture only after very long incubation time.

The classification of Xyl II on the basis of the data presented in Table 4 is not straightforward. This protein has a neutral pI but its molecular mass is much lower than the $M_r$ of the majority of the "high $M_r$/low pI" xylanases. Also, its high specific activity against oat spelt xylan and its decreased ability to hydrolyze short xylooligomers classifies Xyl II nearer the low-molecular-mass enzymes with similar biochemical properties, such as XlNB and XlnC of *S. lividans* (Biely, P. et al., *Biochim. Biophys. Acta* 1162:246–254 (1993)). However, in Western blotting experiments (unpublished) Xyl II gave a positive reaction with a rabbit antibody against Xylanase A from *S. lividans* (a high $M_r$/low pI xylanase), which does not cross-react with the low $M_r$/high pI xylanases XlnB and XlnC from the same organism (Vats-Mehta, S. et al., *Gene*, 86:119–122 (1990)). Consequently, we assume that Xyl II is either a low $M_r$ xylanase with an unusual neutral pI or, more probably, a truncated protein, originating from a high $M_r$-xylanase gene or protein.

Figure 3:
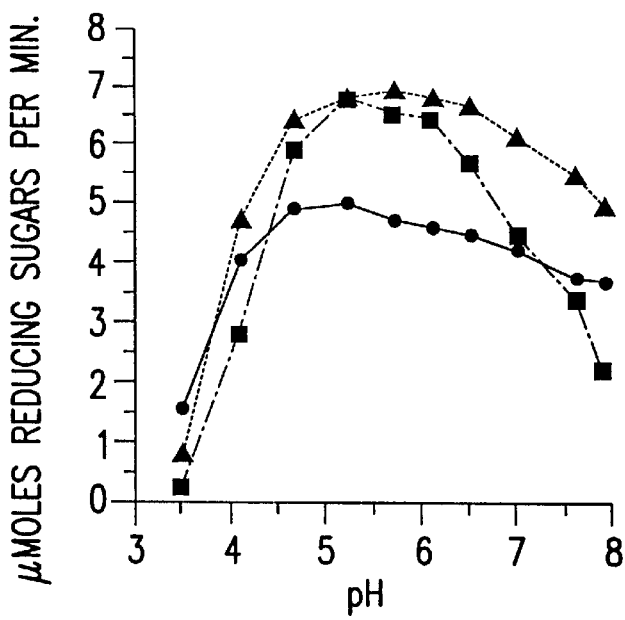
FIG. 3 shows the effect of pH and temperature on Xylanase I activity. Purified Xyl I (5 units) was incubated for 10 min at the temperature and pH values indicated and the release of reducing sugar was measured by the Nelson-Somogyi method. (●) 60° C.; (▼) 70° C.; (■) 80° C.
Figure 4:
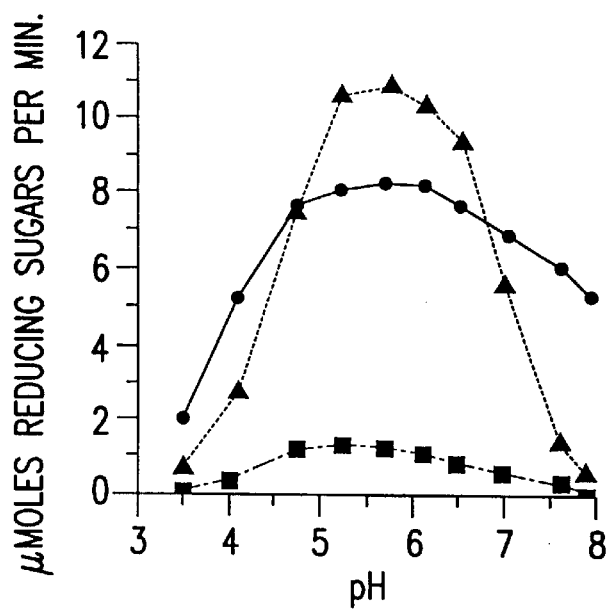
FIG. 4 shows the effect of pH and temperature on Xylanase II activity. Purified Xyl II (8 units) was incubated for 10 min at the temperature and pH values indicated and the release of reducing sugar was measured by the Nelson-Somogyi method. (●) 60° C.; (▼) 70° C.; (■) 80° C.

The effect of pH on both xylanases was studied at three different temperatures (FIGS. 3 and 4). The optimal pH lies between 5.2 and 5.7 for Xyl I as well as for Xyl II. At pH 4 and 70° C. (the temperature used in the screening procedure), Xyl I retained 67% of its maximal activity while Xyl II retained only 26% of its activity in these conditions. Clearly, the level of activity observed at 70° C./pH 4 with the crude culture supernatant of Actinomadura sp. FC7 was due to the predominance of Xyl I among the xylanase forms secreted by this wild-type strain.

Remarkably, at its optimum pH, Xyl I retained full activity even at 80° C. (FIG. 3). At this higher temperature, the decrease of activity in acidic pH was faster, but still less marked than for the majority of known xylanases: 41% of the maximal activity persisted at pH 4. In contrast, even at optimal pH, Xyl II was 8.1-times less active at 80° C. than at 70° C. (FIG. 4).

To estimate the thermal stability of Xyl I, the enzyme was incubated in Teorell buffer in the absence or presence of 100 μg/ml of bovine serum albumin at different temperatures. Periodically, samples were withdrawn and the residual activity was measured by standard assay. When preincubated at pH 6/50° C., Xyl I conserved full activity for at least 96 hours. At pH 6/70° C., the half-life was 6 hours in the absence of BSA and 18 hours in the presence of BSA. At pH 4/70° C., the half-life was 10 hours in the absence of BSA and 22 hours in the presence of BSA. These values are within the range of stabilities obtained for crude thermoresistant xylanases from other Actinomadura species (Holtz, C. et al., *Antonie van Leeuwenhoek* 59:1–7 (1991)); however, they are clearly shifted towards more acidic pHs.

In conclusion, the screening procedure developed for the invention, based on the simultaneous application of two stringent parameters (low pH and high temperature) resulted in the isolation of a xylanolytic actinomycete which produces at least one xylanase that remains almost fully active and is very stable in these conditions.

TABLE 2

Purification of xylanase I and II from culture supernatants of recombinant *Streptomyces lividans* 10-164 strains

| | Total activity (units) | Protein (mg) | Specific activity (units/mg) | Yield (%) | Purifuca- tion factor |
|---|---|---|---|---|---|
| A: Xylanase I produced by *Streptomyces lividans* 10-164 (pJF1) | | | | | |
| Culture broth | 3420 | 90 | 38 | 100 | 1.0 |
| Ethanol precip. | 3250 | 58 | 56 | 95 | 1.5 |
| DEAE-BioGel | 1265 | 9.3 | 135 | 37 | 3.6 |
| BioGel A-0.5 m | 910 | 5.1 | 178 | 27 | 4.7 |
| B: Xylanase II produced by *Streptomyces lividans* 10-164 (pJF6) | | | | | |
| Culture broth | 11460 | 86.8 | 132 | 100 | 1.0 |
| Ethanol precip. | 9412 | 37.5 | 251 | 82 | 1.9 |
| DEAE-BioGel | 4115 | 6.7 | 615 | 38 | 4.6 |
| BioGel A-0.5 m | 1581 | 1.25 | 1268 | 14 | 9.6 |

TABLE 3

Biochemical properties of Xyl I and Xyl II

| | Xyl I | Xyl II |
|---|---|---|
| Molecular weight (after SDS-PAGE) | 48 kDa | 34 kDa |
| Isoelectric point | 5.8 | 7.1 |
| Optimal temperature at pH 5[1,2] | 75° C. | 70° C. |
| Optimal pH at 60° C.[1,2] | 5.2 | 5.7 |
| Main hydrolysis products after 30 min. reaction[1] | xylobiose, xylotriose, higher oligoxylosides | higher oligoxylosides |
| Main hydrolysis products after 18 h. reaction[1] | traces of xylose, xylobiose, xylotriose | xylobiose, xylotriose |
| Aryl-β-D-xylosidase specific activity | 0.13 U/mg | undetectable |
| Staining with Schiff reagent | negative | negative |

[1]Determined with oat spelt xylan as substrate
[2]The reaction time was 10 min.

EXAMPLE 7

Sequence of the Insert in pJF6

Figure 5:
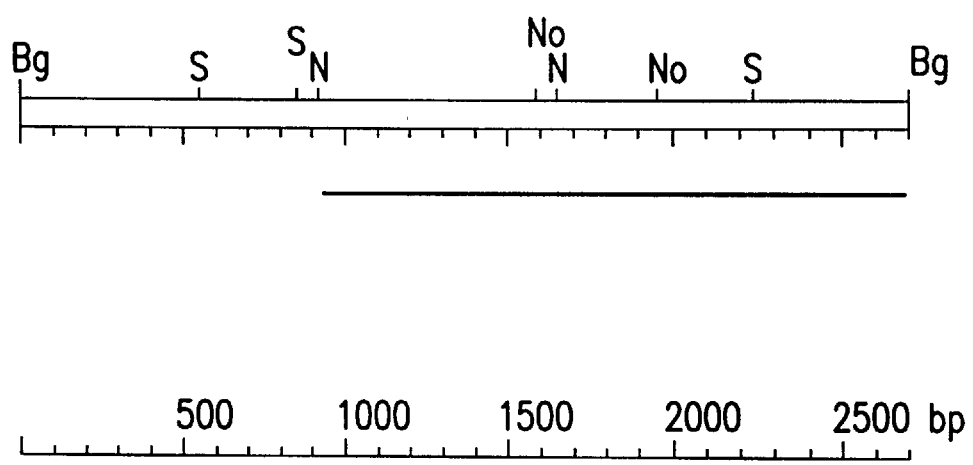
FIG. 5 shows a restriction map of the 2.7 kb insert of clone pJF6 (encoding Xyl II). The black line shows the sequenced portion of the insert, starting from the indicated NruI site. The letters represent the following restriction sites: Bg=BglII, S=SalI, N=NruI, No=NotI.

A restriction map was drawn up to allow sub-cloning of fragments thereby facilitating sequencing (FIG. 5). Several DNA fragments were sub-cloned and sequenced.

The plasmid DNA of the positive clones of the gene bank of the Actinomadura sp. FC7 preparation contained in vector pFD666 was digested by the chosen restriction endonucleases. The DNA fragments thus produced were purified by "Gene Clean" for subsequent ligation to vectors pUC118, pUC119 and pUC21. The unidirectional exonuclease III/ nuclease S1 deletion method described by Henikoff, *Methods enzymol.* 155: 156–165 (1987) was selected in obtaining additional sub-clones.

The Vieira and Messing protocol (*Gene* 100:189–194 (1987)) modified by Parent J-L., The JHJ-1 actinophage: sequencing and promotional study. Master's thesis. Department of Biology. Faculty of Sciences. University of Sherbrooke. 81 p, (1992) was chosen for preparation of single strand DNA. Double strand DNA preparation was completed in accordance with the "T7 Quick Prime Kit" of Pharmacia LKB Biotechnology. Single and double strand DNA sequencing was achieved according to the method of Sanger et al., *Proc. Natl. Acad. Sci. USA.* 74: 5463–5467 (1977) from the "Sequenase and 7-deaza-dGTP" set of United States Biochemical.

A preliminary computer analysis made it possible to prove a very strong sequencing homology to *Streptomyces lividans* xylanase A. This made it possible to localize the beginning of the ORF coding for a xylanase by clone pJF6. Thus, the xlnII gene is localized at, and sequencing was directed to, only a portion of the pJF6 insert, that is, from the NruI site to the BglII site to the right of the restriction map for pJF6 (FIG. 5).

The nucleotide sequence of the insert in pJF6 is presented in FIG. 6 and is Genback Accession No. U08894. An open reading frame (ORF) begins at nucleotide 521 by a codon GTG and ends probably through an end of translation codon located in phase next to the vector, since no terminal codon was found inside the cloned fragment. The gene would therefore be truncated and coded as active xylanase. A Shine-Dalgarno sequence (GGAGGA) specific to the attachment to ribosomes was found at nucleotide 509. According to Strohl, W. R., *Nucleic Acids Research.* 20: 961–974 (1992), this RBS is completely homologous to the consensus sequence produced from 40 streptomycete genes (FIG. 7). The coding region of this gene has a nucleotide content rich in G+C, on the order of 68%. Furthermore, the percentage of nucleotide type (G or C) found at position 3 of the codon is over 90%, which corresponds with the results reported by Bibb et al. (1984).

According to Wong et al., *Microbiol. Rev.* 52(3): 305–317 (1988), xylanases can be classified into two classes, either class A, which regroups the xylanases having a molecular weight over 35 kDa and an acid pI, while class B brings together xylanases with a molecular weight below 35 kDa and a basic pI. Thus this ORF of 1527 nucleotides codes for a xylanase of about 43 kDa, and would therefore belong to class A.

The signal peptide of the pre-protein of this xylanase has the characteristics normally found in such amino acid sequences (Perlman and Halvorson, *J. Mol. Biol.* 167: 391–409 (1983): that is, a positively charged N-terminal extremity containing arginines (R) followed by a long sequence of hydrophobic amino acids and a C-terminal segment including a proline (P) localized near the cleavage site (AXA) of the peptidase signal (FIG. 8).

The promoter region is typical; that is, a spacing of 16 nucleotides separates the -35 region (TTGACG) from the -10 region (CACAAT). This promoter is comparable to those illustrated by Strohl, *Nucleic Acids Research.* 20: 961–974 (1992) (FIG. 9). Furthermore, this promoter would be quite homologous to the promoter consensus sequence (TTGAC. . .TATAAT) found in *Escherichia coli* (Lewin, *Genes,* John Wiley & Sons, Inc. USA, 1983, 715 pages).

The restriction map studies suggested that the 2.5 kb fragment found in clones pJF6, pJF8, pJF10 and pJF11 were identical. The extremities of these fragments were sequenced and compared with one another in order to verify this. The results indicated that the 2.7 kb fragment present in clones pJF8 was identical to the one found in pJF6. Furthermore, the fragments adjoining the 2.7 kb fragment in pJF10 and pJF11 appear to be the result of a multiple ligation, since the sequences obtained represent no significant homology to xylanase A of *S. lividans* or each other.

No translation termination codon was found in the xlnII sequence of pJF6's insert. The implication is that the cloned gene is truncated in its 3' part. This is further suggested by comparing the coding sequence of the xylanase A of *S. lividans* with that encoded by pJF6. About 185 nucleotides appear to be truncated or missing for the sequence encoded by pJF6.

pJF6's coding sequence has the potential for coding a 44 kDa xylanase. However, the MW of the xylanase produced is on the order of 34 kDa. There are three possibilities to explain this. The first hypothesis is that the RNA polymerase is stopped during transcription. The second is that a terminator sequence is present and thereby stops the translational mechanism. The third possibility is that the protein is naturally cleaved proteolytically after synthesis.

According to Akino et al., *Appl. Environ Microbiol.* 55: 3178–3183 ((1989), it is possible for the transcription to be stopped by several inverse repeated sequences. These authors have described a gene coding for two β-mannanases having MWs of 54 kDa and 37 kDa. The production of the 37 kDa mannanase would be due to the stoppage of RNA polymerase as the result of the combined presence of repeated and inverse sequences and a rare codon. Here, such repeated and inverse sequences appear between nucleotides number 1538 and 1672.

These sequences also have the potential to form several secondary structures, which could be very stable in terms of energy, for example, between nucleotides 1538 and 1672 (FIG. 12). A hairpin loop between nucleotides 1538 and 1610 has a calculated internal energy (ΔG) of −55.2 Kcal (Tinoco et al., *Nature.* 246: 40–41 (1973). This might produce a protein of about 34 kDa, but no rare codon has been found near the latter.

The second hypothesis requires the presence of a sequence region in the mRNA, allowing the creation of a second stable structure. In the same area previously shown, there is the potential of forming such a secondary structure. This secondary structure might possibly have the ability to slow down the progression of ribosomes on the mRNA so as to finally stop the entire translation mechanism, in order to ultimately yield a protein on the order of 34 kDa. The third possibility is discussed below.

EXAMPLE 8

Comparison of the Sequence Derived from pJF6 Xylanase Amino Acids with Other Proteins DNA sequences were analyzed with programs of the UWGCG system: FASTA, TFASTA, BESFIT, PILEUP, PRETTY, STEMLOOP, REPEAT, MAP and PROTEIN-STRUCTURE upon sequences obtained from the "Genbank" and "EMBL" databases (Devereux et al., *Nucleic Acids Res.* 12: 387–395 1984).

The TFASTA program was used to study the degree of homology encountered in the amino acid derived sequence of xlnII as encoded by clone pJF6, as compared to the sequences derived from proteins present in databanks.

The PILEUP program then made it possible to align the protein sequences derived (FIGS. 10–10C). A significant homology was observed with the following genes: the xylanase genes of *Butyrivibrio fibrisolvens* (Lin et al., Genbank. Accession no.: X61495 (1991), *Ruminococcus flavefaciens* (Zhang et al., *Mol. Microbiol.* 6: 1013–1023 1992), *Thermoanaerobacter saccharolyticum* (Lee et al., Genbank. Accession No.: M97882, the C-125 alkalophile preparation of Bacillus sp. (Hamamoto et al., *Agric. Biol. Chem.* 51: 953–955 (1987), *Clostridium thermocellum* (Grépinet et al., *J. Bacteriol.* 170: 4582–4588 (1988) as well as two xylanases of *Pseudomonas fluorescens* (Hall et al., *Mol. Microbiol.* 3: 1211–1219 (1989); Kellette et al., *Biochem. J.* 272: 369–376 (1990). Furthermore, homologies have been found in protein sequences derived from proteins coding for exoglucanase genes of *Cellulomonas fimi* (O'Neill et al., *Gene.* 44: 325–330 (1986), for *Clostridium stercoirarium* celloxylanase (Fukumura et al., 1992), and lastly, with a cellulase and a xylanase of *Caldocellum saccharolyticum* (Saul et al., *Appl. Environ. Microbiol.* 56: 3117–3124 (1990); Lüthi et al., *Appl. Environ. Microbiol.* 56: 1017–1024 (1990).

A homology of over 80% has been observed in the xylanase A of *Streptomyces lividans* (Shareck et al., *Gene* 107: 75–82 (1991) (FIG. 11).

The alignment of sequences of proteins derived from the 13 genes mentioned above reveals a total of 66 amino acids which were maintained with a similarity of over 75%, 22 of which are identical at 100%, and therefore the possible presence of 7 regions of retained amino acids (FIGS. 10–10C).

EXAMPLE 9

Computer Prediction of Protease Sites

Figure 13A:
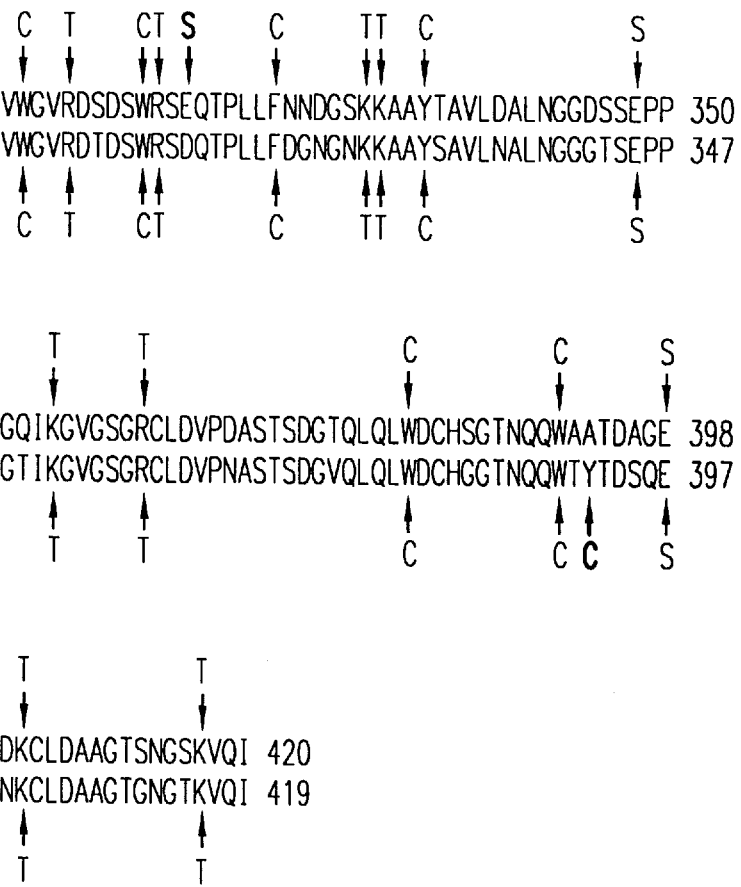

The MAP program was used to evaluate the potential cleavage sites of proteases in an amino acid sequence. FIG. 13 and 13A shows the analysis obtained for the sequences derived from the amino acids of *S. lividans* and pJF6 xylanase.

The significant difference that exists between the two analyzed amino acid derived sequences is as follows: in the vicinity of amino acid 318 encoded by the pJF6 sequence, no cleavage site by *Staphylococcus aureus* protease was found. In contrast, such a site is present in the analysis of the xylanase A sequence of *S. lividans*.

In order to approach the third hypothesis discussed above concerning a possible proteolytic mechanism for the post-translational shortening of the protein, it's necessary to illustrate this last point by comparing the xylanolytic proteins produced by the xylanase A of *Streptomyces lividans* to that of pJF6. It must be noted that the xylanase A gene codes for a 47 kDa protein, and moreover, a second protein on the order of 31 kDa is visible on a polyacrylamide gel (Moreau, A., Doctoral thesis, Department of Microbiology and Immunology, Faculty of Medicine, University of Montréal, 1992, 140 pages). A post-translational maturation process might explain the production of this second 31 kDa molecular form. Comparisons will be brought to bear on this last type of xylanase.

First off, the results show that the sequences derived from the amino acid sequence encoded by pJF6 xylanase and the xylanase A of *S. lividans* are quite homologous. It's normal to expect a practically identical computer analysis regarding the possible protease cleavage sites known from the two sequences derived from amino acids. And yet, a significant difference is revealed in the one proteolytic site. In comparing the analysis of the likely proteolytic cleavage sites of the xylanase A of *S. lividans*, the pJF6 xylanase would have one cleavage site less for a Staphylococcus protease. This protease would recognize glutamic acid (E), with 318 amino acids for xylanase A and 345 amino acids for pJF6 xylanase, to ultimately cleave in the C-terminal portion of the amino acid. This difference in proteolytic cleavage pattern might then explain the production of 31 kDa of xylanolytic protein in *S. lividans* and that of 34 kDa in pJF6. It is known that the portions of a protein exposed to proteolytic cleavage are proteases that tend to cleave the protein in a loop for example situated between two alpha helices, or one alpha helix and a beta sheet, or yet between two beta sheets.

Thanks to the PROTEINSTRUCTURE program, it was possible to prove the potentially cleavable areas using the proteases on the xylanase A of *S. lividans* and the xylanase of pJF6. These results interestingly coincide with the protease cleavage site of the Staphylococcus discussed earlier. Therefore the involvement of protease may explain the maturation mechanism of the xylanase of pJF6 as well as the xylanase A of *S. lividans*.

FIGS. 10–10C demonstrate that there is a significant homology between the xylanases and cellulases. Gilkes et al., *Microbiol. Rev.* 55: 303–315 (1991), after analyzing amino acid sequences for more than 70 cellulase and xylanases, proposed the creation of nine families of enzymes. According to these researchers, the observation of cellulase isoenzymes and the xylanases of several microorganisms would prove that these proteins would not have evolved from a single gene, but rather came from a large multigenic family. Furthermore, the enzymes with a predominant xylanolytic activity are classified into two distinct families. This brings up the following hypothesis: true cellulases and true xylanases would therefore have evolved from different genes.

Given that the xylanase A of *Streptomyces lividans* is so similar to the xylanase of pJF6, the thermostability and acid stability of the xylanase of pJF6 is surprising. According to Moreau, A., Doctoral thesis, Department of Microbiology and Immunology, Faculty of Medicine, University of Montréal, 1992, 140 pages, the xylanase A of *S. lividans* retains only 10% of its activity following incubation at a temperature of 60° C. for 8 hours in the absence of its substrate, while the pJF6 xylanase under the same conditions keeps almost 95% of its activity. The small differences found in amino acid sequences of these two xylanases seems to have imparted a much more stable consistency for the pJF6 xylanase at high temperature.

EXAMPLE 10

Biobleaching Using FC7

Approximately one liter of spent culture medium per ton of pulp is added to pine kraft pulp; the culture medium is taken from Actinomadura sp. FC7 cultivations and contains XYL I and XYL II activities as described in Table 3. The pulp is incubated at a relatively high temperature such as 70° C. and acidic pH such as pH 4 for a period of time sufficient to allow degradation of the XYL I and XYL II susceptible bonds in the xylan that is present. If necessary, the culture medium is filtered before use or concentrated using techniques known in the art. After incubation at the desired temperature and pH, the product is a pine kraft pulp preparation wherein the kappa number (the amount of lignin) in the pine kraft pulp is lower without affecting the mechanical properties of the pulp. Additionally, the preparation requires less chlorine comsumption in any subsequent chemical bleaching.

EXAMPLE 11

Biobleaching Using Recombinantly Produced XYL I and/or XYL II

Approximately one liter of spent culture medium per ton of pulp is added to pine kraft pulp; the culture medium is taken from cultivations of recombinant host cells that express recombinant XYL I and/or recombinant XYL II activities as described in Table 3. The pulp is incubated as described in Example 10, at a relatively high temperature such as 70° C. and acidic pH such as pH 4 for a period of time sufficient to allow degradation of the XYL I and XYL II susceptable bonds in the xylan that is present. If necessary, the culture medium is filtered before use or concentrated using techniques known in the art. After incubation at the desired temperature and pH, the product is a pine kraft pulp preparation wherein the kappa number (the amount of lignin) in the pine kraft pulp is lower without affecting the mechanical properties of the pulp. Additionally, the preparation requires less chlorine comsumption in any subsequent chemical bleaching.

What is claimed is:

1. Purified Actinomadura sp. FC7 XYL I.
2. Purified Actinomadura sp. FC7 XYL II.
3. Culture medium comprising XYLII secreted from a recombinant host that has been transformed with a vector that comprises a DNA sequence encoding said XYLII, said XYLII having the amino acid sequence of Actinomadura sp. FC7 XYLII (SEQ ID No. 64), or an enzymatically active fragment thereof.
4. A method for treating plant biomass, which comprises contacting said biomass with Actinomadura sp. FC7 XYL I, Actinomadura sp. FC7 XYL II, or both said XYL I and said XYL II.
5. The method of claim 4, wherein said method is biobleaching.
6. The method of claim 4, wherein the temperature is above 50° C.
7. The method of claim 6, wherein the temperature is 50°–80° C.
8. The method of claim 7, wherein the temperature is 70° C.
9. The method of claim 4, wherein the pH is below 6.0.
10. The method of claim 9, wherein the pH is between 4.0 and 6.0.
11. The method of claim 10, wherein said pH is 4.0.
12. The method of claim 4, wherein the temperature is above 50° C. and the pH is below 50° C. and the pH is below 6.0.
13. The method of claim 12, wherein said method is biobleaching.
14. The method of claim 12, wherein the said temperature is 50°–80° C.
15. The method of claim 14, wherein the said temperature is 70° C.
16. The method of claim 12, wherein the pH is between 4.0 and 6.0.
17. The method of claim 16, wherein said pH is 4.0.
18. The method of any one of claims 4–17, wherein said biomass is contacted with said XYL I.
19. The method of any one of claims 4–17, wherein said biomass is contacted with said XYL II.
20. The method of any one of claims 4–17, wherein said biomass is contacted with both said XYL I and said XYL II.
21. A method for hydrolyzing xylan, said method comprising contacting said xylan with Actinomadura sp. FC7 XYL I, Actinomadura sp. FC7 XYL II or both said XYL I and said XYL II.
22. A method for treating xylan-containing plant biomass byproducts to hydrolyze the xylan therein, said method comprising contacting said xylan in said xylan-containing plant biomass byproduct with Actinomadura sp. FC7 XYL I, Actinomadura sp. FC7 XYL II or both said XYL I and said XYL II.
23. The method of any one of claims 21 or 22, wherein the temperature is above 50° C.
24. The method of claim 23, wherein said temperature is 50°–80° C.
25. The method of claim 24, wherein said temperature is 70° C.
26. The method of any one of claims 21 or 22, wherein the pH is below 6.0.
27. The method of any one of claims 21 or 22, wherein said pH is between 4.0 and 6.0.
28. The method of any one of claim 27, wherein said pH is 4.0.
29. The method of any one of claims 21 or 22, wherein the temperature is above 50° C. and the pH is below 6.0.
30. The method of claim 29, wherein said temperature is 50°–80° C.
31. The method of claim 30, wherein said temperature is 70° C.
32. The method of claim 29, wherein said pH is between 4.0 and 6.0.
33. The method of claim 32, wherein said pH is 4.0.
34. The method of any one of claims 21 or 22, wherein said xylan is contacted with said XYL I.
35. The method of any one of claims 21 or 22, wherein said xylan is contacted with said XYL II.
36. The method of any one of claims 21 or 22, wherein said xylan is contacted with both said said XYL I and said XYL II.
37. The method of any one of claims 21 or 22, wherein said xylan is in a hemicellulose liquor.
38. Spent culture medium from the cultivation of Actinomadura sp. FC7 (ATCC 55698).

* * * * *

UNITED STATES PATENT AND TRADEMARK OFFICE
Certificate

Patent No. 5,871,730                           Patented: February 16, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: patent is: Ryszard Brzezinski, Sherbrooke, Canada; Claude V. Déry, Fleurimont, Canada; Carole Beaulieu, Sherbrooke, Canada; Jean F. Éthier, Hull Quebec, Canada; and Serge Harpin, Quebec, Canada.

Signed and Sealed this Sixth Day of April 2004.

PONNATHAPURA N. ACHUTAMURTHY
*Supervisory Patent Examiner*
Art Unit 1652